United States Patent
Hagiwara et al.

(10) Patent No.: US 9,745,323 B2
(45) Date of Patent: Aug. 29, 2017

(54) COMPOUND AND PHARMACEUTICAL COMPOSITION FOR NEUROPSYCHOLOGICAL DISORDER OR MALIGNANT TUMOR

(71) Applicants: KYOTO UNIVERSITY, Kyoto-shi, Kyoto (JP); NATIONAL UNIVERSITY CORPORATION TOKYO MEDICAL AND DENTAL UNIVERSITY, Tokyo (JP); KINOPHARMA, INC., Tokyo (JP)

(72) Inventors: Masatoshi Hagiwara, Kyoto (JP); Hiroshi Onogi, Tokyo (JP); Isao Kii, Kyoto (JP); Takamitsu Hosoya, Tokyo (JP); Yuto Sumida, Tokyo (JP)

(73) Assignees: KYOTO UNIVERSITY, Kyoto-Shi (JP); NATIONAL UNIVERSITY CORPORATION TOKYO MEDICAL AND DENTAL UNIVERSITY, Tokyo (JP); KINOPHARMA, INC., Tokyo (JP)

( * ) Notice: Subject to any disclaimer, the term of this patent is extended or adjusted under 35 U.S.C. 154(b) by 0 days.

(21) Appl. No.: 14/418,342

(22) PCT Filed: Jul. 30, 2013

(86) PCT No.: PCT/JP2013/070636
§ 371 (c)(1),
(2) Date: Jan. 29, 2015

(87) PCT Pub. No.: WO2014/021337
PCT Pub. Date: Feb. 6, 2014

(65) Prior Publication Data
US 2015/0225421 A1    Aug. 13, 2015

(30) Foreign Application Priority Data
Jul. 30, 2012   (JP) .................... 2012-168850

(51) Int. Cl.
*C07D 513/04* (2006.01)
*C07D 405/06* (2006.01)
*C07D 417/06* (2006.01)

(52) U.S. Cl.
CPC .......... *C07D 513/04* (2013.01); *C07D 405/06* (2013.01); *C07D 417/06* (2013.01)

(58) Field of Classification Search
CPC .................................................. C07D 513/04
See application file for complete search history.

(56) References Cited

U.S. PATENT DOCUMENTS

| | | |
|---|---|---|
| 2005/0171026 A1 | 8/2005 | Hagiwara et al. |
| 2006/0293338 A1 | 12/2006 | Hasegawa et al. |
| 2009/0023742 A1 | 1/2009 | Dhanak et al. |
| 2010/0184774 A1 | 7/2010 | Duffy et al. |

FOREIGN PATENT DOCUMENTS

| | | |
|---|---|---|
| JP | WO 2004/007491 A1 | 1/2004 |
| JP | 2009-528383 A | 8/2009 |
| WO | WO 2005/011686 A1 | 2/2005 |
| WO | WO 2007/103754 A2 | 9/2007 |
| WO | WO 2010/010797 A1 | 1/2010 |
| WO | WO 2012/065139 A2 | 5/2012 |

OTHER PUBLICATIONS

Chemical Abstracts Registry No. 701294-28-2, indexed in the Registry file on STN CAS Online Jun. 30, 2004.*
Thompson et al., Current Medicinal Chemistry, Oct. 2002, 9(19), pp. 1751-1762.*
Golub et al., Science, vol. 286, Oct. 15, 1999, pp. 531-537.*
Extended European Search Report for European Application No. 13825401.6, dated Mar. 3, 2016.
Ogawa et al., "Development of a Novel Selective Inhibitor of the Down Syndrome-related Kinase Dyrk1A," Nature Communications, vol. 1, No. 86, Oct. 5, 2010, pp. 1-9.
International Search Report issued in PCT/JP2013/070636, mailed on Nov. 5, 2013.
(Continued)

*Primary Examiner* — Laura L. Stockton
(74) *Attorney, Agent, or Firm* — Birch, Stewart, Kolasch & Birch, LLP

(57) ABSTRACT

The present invention provides a compound and a pharmaceutical composition for neuropsychological disorders or malignant tumors, the use of the compound and the pharmaceutical composition, or a method for preventing, improving, inhibiting the development of, and/or treating neuropsychological disorders or malignant tumors with the use of the compound and the pharmaceutical composition. One or more embodiments disclose a compound expressed by the following general formula (I) or (II) or a pharmaceutically acceptable salt of the compound:

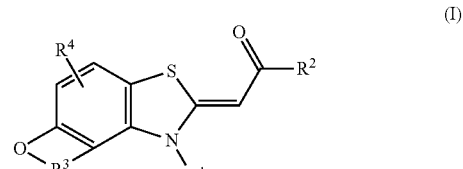

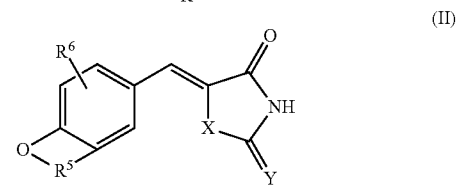

9 Claims, 9 Drawing Sheets

(56) References Cited

OTHER PUBLICATIONS

Janusz et al., "New Cyclooxygenase-2/5-Lipoxygenase Inhibitors. 3. 7-tert-Butyl-2,3-dihydro-3, 3-dimethylbenzofuran Derivatives as Gastrointestinal Safe Antiinflammatory and Analgesic Agents: Variations at the 5 Position", Journal of Medicinal Chemistry, vol. 41, No. 18, 1998, pp. 3515-3529.

Muraki et al., "Manipulation of Alternative Splicing by a Newly Developed Inhibitor of CIks", The Journal of Biological Chemistry, vol. 279, No. 23, Jun. 4, 2004, pp. 24246-24254.

Office Action issued Aug. 23, 2016, in Canadian Patent Application No. 2,880,487.

1 Canadian Office Action for Appl. No. 2,880,487 dated May 4, 2017.

* cited by examiner

COMPOUND AND PHARMACEUTICAL COMPOSITION FOR NEUROPSYCHOLOGICAL DISORDER OR MALIGNANT TUMOR

TECHNICAL FIELD

The present invention relates to a compound and a pharmaceutical composition for neuropsychological disorders or malignant tumors, the use of the compound and the pharmaceutical composition, and a method for preventing, improving, inhibiting the development of, and/or treating neuropsychological disorders or malignant tumors with the use of the compound and the pharmaceutical composition.

BACKGROUND ART

A protein phosphoenzyme (kinase) is essential for intracellular signal transduction, and abnormal expression or abnormal activation of the protein phosphoenzyme has been known to give rise to various diseases. Therefore, a wide variety of phosphoenzymes attracts attention as target agents for innovative drug development, and inhibitors specific to target phosphoenzymes are being searched for all over the world.

For example, Patent Document 1 discloses benzothiazole derivatives that can inhibit the phosphorylation activity of phosphoenzymes Clk1 and Clk4. Patent Document 2 discloses benzothiazole derivatives that can inhibit the phosphorylation activity of a phosphoenzyme DYRK.

PRIOR ART DOCUMENTS

Patent Documents

Patent Document 1: US 2005/0171026 A1
Patent Document 2: WO 2010/010797 A1

DISCLOSURE OF INVENTION

Problem to be Solved by the Invention

In one aspect, the present disclosure provides a compound and a pharmaceutical composition for neuropsychological disorders or malignant tumors, the use of the compound and the pharmaceutical composition, or a method for preventing, improving, inhibiting the development of, and/or treating neuropsychological disorders or malignant tumors with the use of the compound and the pharmaceutical composition.

Means for Solving Problem

In one aspect, the present disclosure relates to a compound expressed by the following general formula (I) or a prodrug of the compound or a pharmaceutically acceptable salt of the compound:

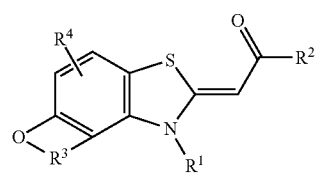

(I)

(where, in the general formula (I), $R^1$ and $R^2$ each independently represent a hydrogen atom or a $C_{1-6}$ hydrocarbon chain, $R^3$ represents

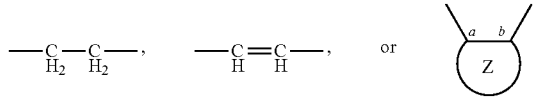

where Z and atoms marked with a and b form a ring selected from the group consisting of one benzene ring, one heteroaromatic ring, an aromatic ring in which one or more benzene rings are condensed, a heteroaromatic ring in which one or more heteroaromatic rings are condensed, a mixed condensed polycyclic ring in which one or more benzene rings are condensed with one or more heteroaromatic rings, and a cyclic aliphatic, and the ring may have at least one substituent that is a hydrogen atom, a halogen atom, or a $C_{1-6}$ alkyl group, and $R^4$ represents a hydrogen atom, a halogen atom, or a $C_{1-6}$ alkyl group).

In another aspect, the present disclosure relates to a compound expressed by

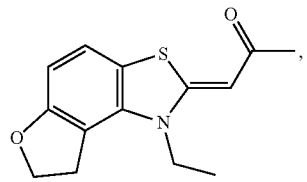

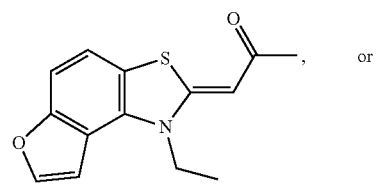

, or

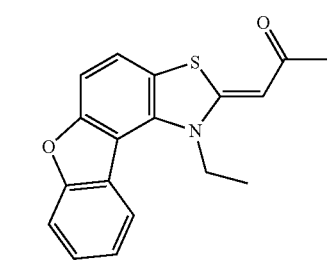

or a prodrug of the compound or a pharmaceutically acceptable salt of the compound.

In another aspect, the present disclosure relates to a compound expressed by the following general formula (III) or a prodrug of the compound or a pharmaceutically acceptable salt of the compound:

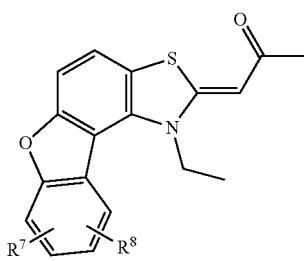

(III)

(where, in the general formula (III), $R^7$ and $R^8$ each independently represent a hydrogen atom, a halogen atom, or a linear, branched, or cyclic $C_{1-6}$ alkyl group).

In another aspect, the present disclosure relates to a compound expressed by

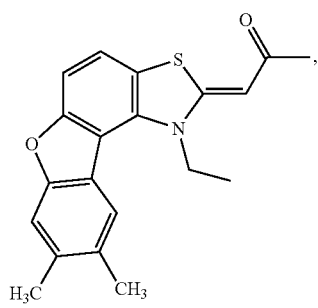

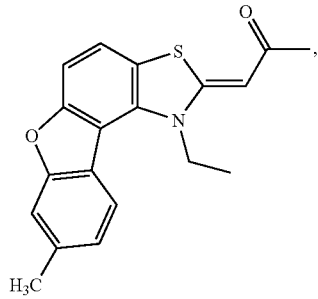

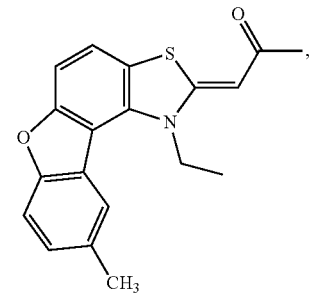

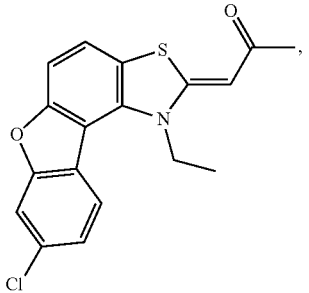

or

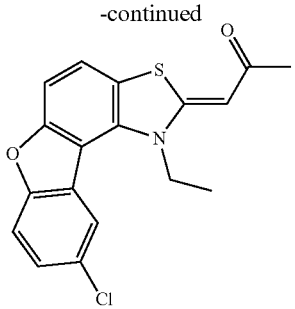

or a prodrug of the compound or a pharmaceutically acceptable salt of the compound.

In another aspect, the present disclosure relates to a compound expressed by the general formula (I) or (III) or a prodrug of the compound or a pharmaceutically acceptable salt of the compound and a pharmaceutical composition containing the compound. In another aspect, the present disclosure relates to a compound expressed by the general formula (I) or (III) or a prodrug of the compound or a pharmaceutically acceptable salt of the compound and a pharmaceutical composition containing the compound for preventing, improving, inhibiting the development of and/or treating neuropsychological disorders or malignant tumors, the use of the compound and the pharmaceutical composition, and a method of prevention, improvement, inhibition of the development, and/or treatment with the use of the compound and the pharmaceutical composition.

In another aspect, the present disclosure relates to a compound expressed by the following general formula (II) or a prodrug of the compound or a pharmaceutically acceptable salt of the compound:

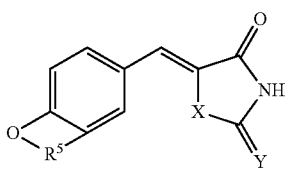

(II)

(where, in the general formula (II), X and Y each independently represent S or NH, $R^5$ represents

where Z and atoms marked with a and b form a ring selected from the group consisting of one benzene ring, one heteroaromatic ring, an aromatic ring in which one or more benzene rings are condensed, a heteroaromatic ring in which one or more heteroaromatic rings are condensed, a mixed condensed polycyclic ring in which one or more benzene rings are condensed with one or more heteroaromatic rings, and a cyclic aliphatic, and the ring may have at least one substituent that is a hydrogen atom, a halogen atom, or a $C_{1-6}$ alkyl group, and $R^6$ represents a hydrogen atom, a halogen atom, or a $C_{1-6}$ alkyl group).

In another aspect, the present disclosure relates to a compound expressed by

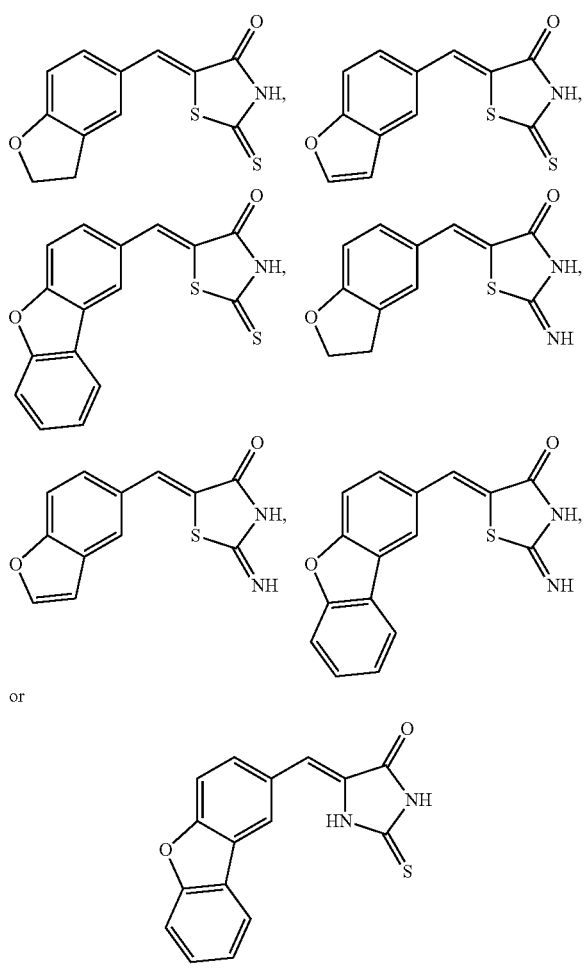

or a prodrug of the compound or a pharmaceutically acceptable salt of the compound.

In another aspect, the present disclosure relates to a compound expressed by the general formula (II) or a prodrug of the compound or a pharmaceutically acceptable salt of the compound and a pharmaceutical composition containing the compound. In another aspect, the present disclosure relates to a compound expressed by the general formula (II) or a prodrug of the compound or a pharmaceutically acceptable salt of the compound and a pharmaceutical composition containing the compound for preventing, improving, inhibiting the development of and/or treating neuropsychological disorders or malignant tumors, the use of the compound and the pharmaceutical composition, and a method of prevention, improvement, inhibition of the development, and/or treatment with the use of the compound and the pharmaceutical composition.

BRIEF DESCRIPTION OF DRAWINGS

FIG. 19A shows the results of a reference memory between the 8th day (training trial 1) and the 12th day (training trial 5) of the tests. FIG. 19B shows the results of a probe test on the 13th day of the tests.

DESCRIPTION OF THE INVENTION

Compound Expressed by General Formula (I)

Figure 1:
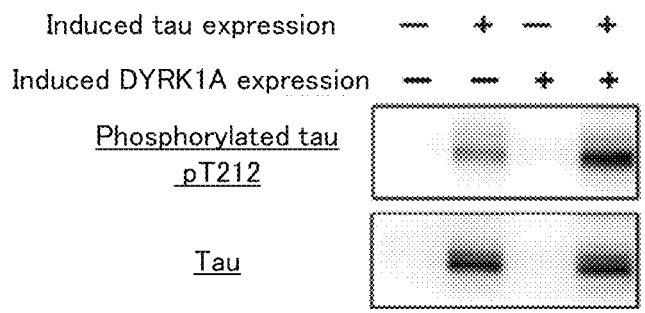
FIG. 1 shown an example of the results of performing western blotting on cultured cells in an evaluation system by using the following antibodies: (i) an antibody that specifically recognizes the phosphorylation of a threonine residue at position 212 of tau protein (upper side); and (ii) an antibody that specifically recognizes tau protein (lower side).

In one or more embodiments, the present disclosure relates to a compound expressed by the following general formula (I) or a prodrug of the compound or a pharmaceutically acceptable salt of the compound:

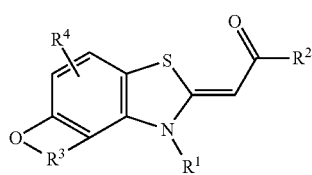

(where, in the general formula (I), $R^1$ and $R^2$ each independently represent a hydrogen atom or a $C_{1-6}$ hydrocarbon chain, $R^3$ represents

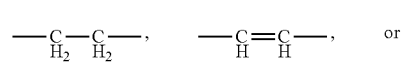 or 

where Z and atoms marked with a and b form a ring selected from the group consisting of one benzene ring, one heteroaromatic ring, an aromatic ring in which one or more benzene rings are condensed, a heteroaromatic ring in which one or more heteroaromatic rings are condensed, a mixed condensed polycyclic ring in which one or more benzene rings are condensed with one or more heteroaromatic rings, and a cyclic aliphatic, and the ring may have at least one substituent that is a hydrogen atom, a halogen atom, or a $C_{1-6}$ alkyl group, and $R^4$ represents a hydrogen atom, a halogen atom, or a $C_{1-6}$ alkyl group).

In one or more embodiments, the "prodrug" of the present disclosure may be a compound that is easily hydrolyzed in a living body to regenerate the compound of the formula (I). If a compound has, e.g., a carboxyl group, the prodrug of the compound may be a compound in which the carboxyl group is converted to an alkoxycarbonyl group, a compound in which the carboxyl group is converted to an alkylthiocarbonyl group, or a compound in which the carboxyl group is converted to an alkylaminocarbonyl group. Moreover, if a compound has, e.g., an amino group, the prodrug of the compound may be a compound in which the amino group is substituted with an alkanoyl group to form an alkanoylamino group, a compound in which the amino group is substituted with an alkoxycarbonyl group to form an alkoxycarbonylamino group, a compound in which the amino group is converted to an acyloxymethylamino group, or a compound in which the amino group is converted to hydroxylamine. Further, if a compound has, e.g., a hydroxyl group, the prodrug of the compound may be a compound in which the hydroxyl group is substituted with the acyl group to form an acyloxy group, a compound in which the hydroxyl group is converted to a phosphoric ester, or a compound in which the hydroxyl group is converted to an acyloxymethyloxy group. The alkyl portion of the group used for the above conversion to the prodrug may be an alkyl group, as will be described later. The alkyl group may be substituted (e.g., with an alkoxy group having 1 to 6 carbon atoms). In one or more embodiments, e.g., when the prodrug is a compound obtained by converting the carboxyl group to an alkoxycarbonyl group, the compound may include lower alkoxycarbonyl (i.e., having 1 to 6 carbon atoms) such as methoxycarbonyl and ethoxycarbonyl, or lower alkoxycarbonyl (e.g., having 1 to 6 carbon atoms) substituted with an alkoxy group such as methoxymethoxycarbonyl, ethoxymethoxycarbonyl, 2-methoxyethoxycarbonyl, 2-methoxyethoxymethoxycarbonyl, and pivaloyloxymethoxycarbonyl.

The "$C_{1-6}$ hydrocarbon chain" of the present disclosure refers to a monovalent group induced by removing any one of hydrogen atoms from an aliphatic hydrocarbon with 1 to 6 carbon atoms. In one or more embodiments, the hydrocarbon chain may have a linear, branched, or cyclic structure and may be an alkyl group, an alkenyl group, a phenyl group, or a cycloalkyl group. In one or more embodiments, examples of the "$C_{1-6}$ alkyl group" of the present disclosure include the following: a methyl group; an ethyl group; a 1-propyl group; a 2-propyl group; a 2-methyl-1-propyl group; a 2-methyl-2-propyl group; a 1-butyl group; a 2-butyl group; a 1-pentyl group; a 2-pentyl group; a 3-pentyl group; a 2-methyl-1-butyl group; a 3-methyl-1-butyl group; a 2-methyl-2-butyl group; a 3-methyl-2-butyl group; a 2,2-dimethyl-1-propyl group; a 1-hexyl group; a 2-hexyl group; a 3-hexyl group; a 2-methyl-1-pentyl group; a 3-methyl-1-pentyl group; a 4-methyl-1-pentyl group; a 2-methyl-2-pentyl group; a 3-methyl-2-pentyl group; a 4-methyl-2-pentyl group; a 2-methyl-3-pentyl group; a 3-methyl-3- pentyl group; a 2,3-dimethyl-1-butyl group; a 3,3-dimethyl-1-butyl group; a 2,2-dimethyl-1-butyl group; a 2-ethyl-1-butyl group; a 3,3-dimethyl-2-butyl group; and a 2,3-dimethyl-2-butyl group.

The "heterocyclic ring" of the present disclosure contains 1 to 2 hetero atoms as ring member atoms and may have a double bond. The heterocyclic ring means a non-aromatic ring or an aromatic ring. The "heteroaromatic ring" of the present disclosure means an aromatic heterocyclic ring. The "hetero atom" of the present disclosure means a sulfur atom, an oxygen atom, or a nitrogen atom.

The "cyclic aliphatic" of the present disclosure means an aliphatic having a cyclic structure. The group of the cyclic aliphatic may be, e.g., either a cyclic aliphatic group having 3 to 10 carbon atoms or a cyclic aliphatic group having a condensed ring structure of a plurality of rings. Specific examples of the cyclic aliphatic group include a cycloalkyl group having 3 to 10 carbon atoms, a cyclic ether group, a decahydronaphthyl group, and an adamantly group. Specific examples of the cyclic aliphatic group having 3 to 10 carbon atoms include a cyclopropyl group, a cyclobutyl group, a cyclopentyl group, a cyclohexyl group, and a cycloheptyl group.

The "pharmaceutically acceptable salt" of the present disclosure includes a pharmacologically and/or medically acceptable salt, and may be, e.g., an inorganic acid salt, an organic acid salt, an inorganic base salt, an organic base salt, or an acidic or basic amino acid salt.

Preferred examples of the inorganic acid salt include the following: hydrochloride; hydrobromate; sulfate; nitrate; and phosphate. Preferred examples of the organic acid salt include the following: acetate; succinate; fumarate; maleate; tartrate; citrate; lactate; stearate; benzoate; methanesulfonate; and p-toluenesulfonate.

Preferred examples of the inorganic base salt include the following: alkali metal salts such as sodium salt and potassium salt; alkaline-earth metal salts such as calcium salt and magnesium salt; aluminum salts; and ammonium salts. Preferred examples of the organic base salt include the following: diethylamine salt; diethanolamine salt; meglumine salt; and N,N'-dibenzylethylenediamine salt.

Preferred examples of the acidic amino acid salt include aspartate and glutamate. Preferred examples of the basic amino acid salt include arginine salt, lysine salt, and ornithine salt.

The "salt of the compound" of the present disclosure may include a hydrate that can be formed by allowing the compound to stand in the air so that it absorbs water. Moreover, the "salt of the compound" of the present disclosure may also include a solvate that can be formed by letting the compound absorb some type of solvent.

In one or more embodiments, $R^1$ of the general formula (I) represents a $C_{1-6}$ alkyl group. Moreover, in one or more embodiments, $R^1$ represents a methyl group, an ethyl group, or a propyl group. In one or more embodiments, $R^2$ of the general formula (I) represents a $C_{1-6}$ alkyl group. Moreover, in one or more embodiments, $R^2$ represents a methyl group. In one or more embodiments, $R^3$ of the general formula (I) represents

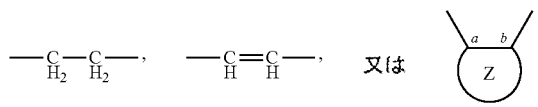

where, in one or more embodiments, Z and atoms marked with a and b form one benzene ring. In one or more embodiments, $R^4$ of the general formula (I) represents a hydrogen atom.

In one or more embodiments, the compound of the general formula (I) is a compound expressed by

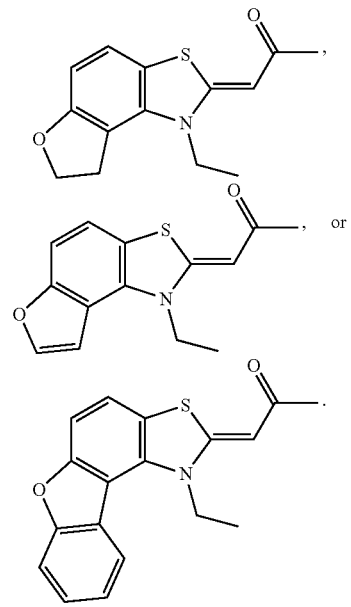

In one or more embodiments, the compound of the general formula (I) is a compound expressed by the following general formula (III):

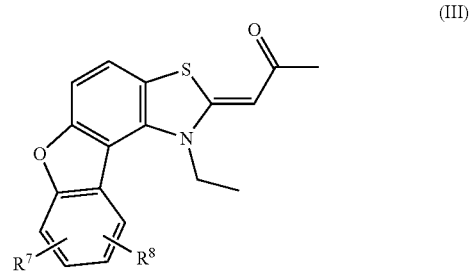

(III)

(where, in the general formula (III), $R^7$ and $R^8$ each independently represent a hydrogen atom, a halogen atom, or a linear, branched, or cyclic $C_{1-6}$ alkyl group).

In one or more embodiments, examples of the linear or branched $C_{1-6}$ alkyl group as represented by $R^7$ and $R^8$ include the following: a methyl group; an ethyl group; a 1-propyl group; a 2-propyl group; a 2-methyl-1-propyl group; a 2-methyl-2-propyl group; a 1-butyl group; a 2-butyl group; a 1-pentyl group; a 2-pentyl group; a 3-pentyl group; a 2-methyl-1-butyl group; a 3-methyl-1-butyl group; a 2-methyl-2-butyl group; a 3-methyl-2-butyl group; a 2,2-dimethyl-1-propyl group; a 1-hexyl group; a 2-hexyl group; a 3-hexyl group; a 2-methyl-1-pentyl group; a 3-methyl-1-pentyl group; a 4-methyl-1-pentyl group; a 2-methyl-2-pentyl group; a 3-methyl-2-pentyl group; a 4-methyl-2-pentyl group; a 2-methyl-3-pentyl group; a 3-methyl-3-pentyl group; a 2,3-dimethyl-1-butyl group; a 3,3-dimethyl-1-butyl group; a 2,2-dimethyl-1-butyl group; a 2-ethyl-1- butyl group; a 3,3-dimethyl-2-butyl group; and a 2,3-dimethyl-2-butyl group. In one or more embodiments, examples of the cyclic $C_{1-6}$ alkyl group as represented by $R^7$ and $R^8$ include the following: cyclopropyl; cyclobutyl; cyclopentyl; and cyclohexyl.

In one or more embodiments, the compound of the general formula (III) is a compound expressed by

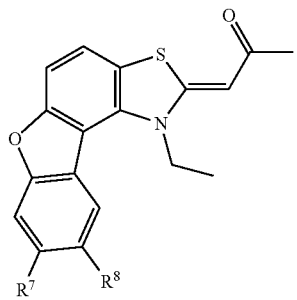

where $R^7$ and $R^8$ each independently represent the atoms or groups as defined above.

In one or more embodiments, $R^7$ and $R^8$ of the general formula (III) each independently represent a hydrogen atom, a halogen atom, or a linear or branched $C_{1-6}$ alkyl group.

In one or more embodiments, the compound of the general formula (III) is a compound expressed by

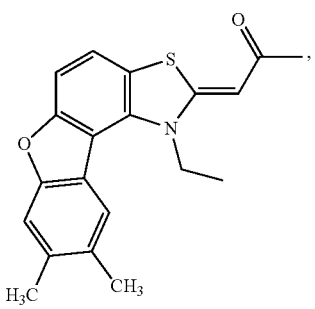

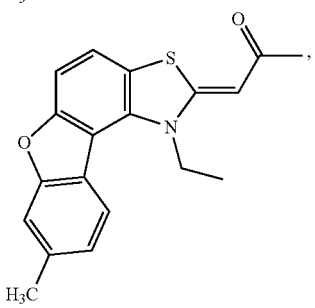

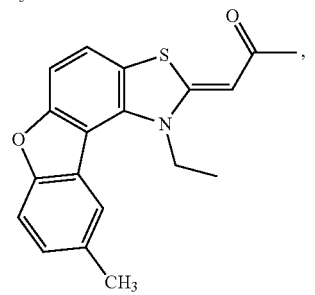

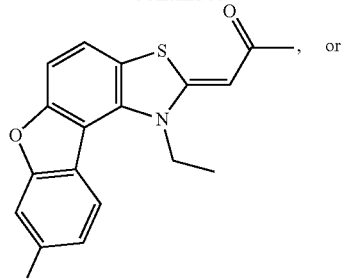

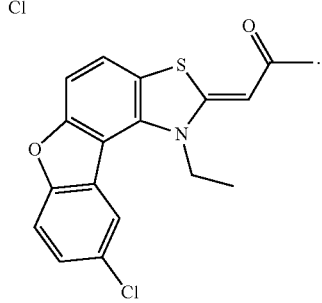

[Prevention, Improvement, Inhibition of Development, and/or Treatment of Neuropsychological Disorders or Malignant Tumors]

A compound expressed by the general formula (I) or (III) or a prodrug of the compound or a pharmaceutically acceptable salt of the compound is effective in preventing, improving, inhibiting the development of, and/or treating neuropsychological disorders or malignant tumors. This mechanism is estimated as follows. The compound of the general formula (I) or (III) or the pharmaceutically acceptable salt of the compound can inhibit not only abnormal phosphorylation of tau protein, but also phosphorylation of amyloid precursor protein (APP), and thus can inhibit the production of amyloid β (Aβ) peptide. Accordingly, neuropsychological disorders may be prevented, improved, inhibited in their development, and/or treated. Moreover, due to the effect of inhibiting the activity of phosphoenzymes, malignant tumors may be prevented, improved, inhibited in their development, and/or treated. However, the present disclosure should not be limited to the above estimation. In one or more embodiments, the compound of the general formula (I) or (III) or the prodrug of the compound or the pharmaceutically acceptable salt of the compound exhibits intracerebral transferability and oral absorbability. These properties can more effectively prevent, improve, inhibit the development of, and/or treat neuropsychological disorders or malignant tumors.

In one or more non-limiting embodiments, the "neuropsychological disorders" of the present disclosure may include the following: Down's syndrome; Alzheimer's disease; and Alzheimer's disease that can be seen in Down's syndrome.

In one or more non-limiting embodiments, the "malignant tumors" of the present disclosure may include the following: brain tumor; glioblastoma; pancreatic duct cancer; rhabdomyosarcoma; lung cancer; pancreatic cancer; colon cancer; skin cancer; prostatic cancer; breast cancer; and ovarian cancer.

In another one or more non-limiting embodiments, the "malignant tumors" of the present disclosure are existing drug-resistant malignant tumors. In yet another embodiment, the "malignant tumors" of the present disclosure are malignant tumors that are known or will be known in the future to be prevented, improved, inhibited in their development, and/or treated by suppressing or inhibiting the receptor tyrosine kinase activity. In yet another embodiment, the "malignant tumors" of the present disclosure are malignant tumors that are known or will be known in the future to be prevented, improved, inhibited in their development, and/or treated by suppressing or inhibiting the epidermal growth factor receptor (EGFR) tyrosine kinase activity. Moreover, in yet another embodiment, the "malignant tumors" of the present disclosure are malignant tumors for which it is known or will be known in the future that drugs for inhibiting the receptor tyrosine kinase activity or the epidermal growth factor receptor (EGFR) tyrosine kinase activity have no significant effect on the prevention, improvement, inhibition of the development, and/or treatment of the malignant tumors. Further, in yet another embodiment, the "malignant tumors" of the present disclosure are malignant tumors for which it is known or will be known in the future that gefitinib has no significant effect on the prevention, improvement, inhibition of the development, and/or treatment of the malignant tumors. In one or more non-limiting embodiments, the compounds of the general formulas (I) and/or (II) and/or (III) or the pharmaceutically acceptable salts of those compounds may affect the stability of the receptor tyrosine kinase or the epidermal growth factor receptor (EGFR) tyrosine kinase and make them unstable. Due to this effect, the malignant tumors may be prevented, improved, inhibited in their development, and/or treated. However, the present disclosure should not be limited to the above estimation.

In one or more embodiments, the present disclosure relates to a compound expressed by the general formula (I) or (III) or a prodrug of the compound or a pharmaceutically acceptable salt of the compound for preventing, improving, inhibiting the development of, and/or treating neuropsychological disorders or malignant tumors. In one or more embodiments, the present disclosure relates to a pharmaceutical composition containing the compound expressed by the general formula (I) or (III) or the prodrug of the compound or the pharmaceutically acceptable salt of the compound as an active ingredient. In one or more embodiments, the present disclosure relates to a pharmaceutical composition (also referred to as a "pharmaceutical composition I of the present disclosure" in the following) for preventing, improving, inhibiting the development of and/or treating neuropsychological disorders or malignant tumors, which contains the compound expressed by the general formula (I) or (III) or the prodrug of the compound or the pharmaceutically acceptable salt of the compound as an active ingredient. Moreover, in one or more embodiments, the present disclosure relates to the use of the compound expressed by the general formula (I) or (III) or the prodrug of the compound or the pharmaceutically acceptable salt of the compound in manufacture of a pharmaceutical composition for preventing, improving, inhibiting the development of, and/or treating neuropsychological disorders or malignant tumors.

In one or more embodiments, the "pharmaceutical composition" of the present disclosure may have a dosage form suitable for administration by using the known formulation technology. Specifically, the pharmaceutical composition can be administered orally in dosage forms (but not limited thereto) such as tablets, capsules, granules, powder, pills, troche, syrups, and liquid formulations. Alternatively, the pharmaceutical composition can be administered parenterally in dosage forms (but not limited thereto) such as injection, liquid formulations, aerosol, suppositories, patches, cataplasm, lotions, liniments, ointments, and eye drops. These formulations can be produced by a known method using additives (but not limited thereto) such as excipients, lubricants, binders, disintegrators, stabilizers, corrigents, and diluents.

Examples of the excipient include (but not limited thereto) the following: starches such as starch, potato starch, and corn starch; lactose; crystalline cellulose; and calcium hydrogen phosphate. Examples of the coating agent include (but not limited thereto) the following: ethyl cellulose; hydroxypropyl cellulose; hydroxypropyl methylcellulose; shellac; talc; carnauba wax; and paraffin. Examples of the binder include (but not limited thereto) the following: polyvinyl pyrrolidone; macrogol; and the compounds similar to those given as examples of the excipient. Examples of the disintegrator include (but not limited thereto) the following: the compounds similar to those given as examples of the excipient; and chemically modified starches and celluloses such as croscarmellose sodium, sodium carboxymethyl starch, and cross-linked polyvinylpyrrolidone. Examples of the stabilizer include (but not limited thereto) the following: parahydroxybenzoic acid esters such as methylparaben and propylparaben; alcohols such as chlorobutanol, benzyl alcohol, and phenylethyl alcohol; benzalkonium chloride; phenols such as phenol and cresol; thimerosal; dehydroacetic acid; and sorbic acid. Examples of the corrigent include (but not limited thereto) commonly used sweeteners, acidulants, and flavors.

The preparation of a liquid formulation may use (but not limited thereto) ethanol, phenol, chlorocresol, purified water, or distilled water as a solvent, and may also use a surface-active agent or an emulsifying agent as needed. Examples of the surface-active agent or the emulsifying agent include (but not limited thereto) polysorbate 80, polyoxyl 40 stearate, and lauromacrogol.

The method for using the pharmaceutical composition I of the present disclosure may differ depending on symptoms, ages, administration methods, etc. The method allows the pharmaceutical composition I to be intermittently or continuously administered (but not limited thereto) orally, endermically, submucosally, subcutaneously, intramuscularly, intravascularly, intracerebrally, or intraperitoneally so that the concentration of the compound (active ingredient) of the general formula (I) or (III) in the body is in the range of 100 nM to 1 mM. In a non-limiting embodiment, for oral administration, the pharmaceutical composition I may be administered to a subject (e.g., an adult human) in a dosage of 0.01 mg (preferably 0.1 mg) to 2000 mg (preferably 500 mg and more preferably 100 mg), which is expressed in terms of the compound of the general formula (I) or (III), once or several times a day based on the symptom. In a non-limiting embodiment, for intravenous administration, the pharmaceutical composition I may be administered to a subject (e.g., an adult human) in a dosage of 0.001 mg (preferably 0.01 mg) to 500 mg (preferably 50 mg) once or several times a day based on the symptom.

In one or more embodiments, the present disclosure relates to a method for preventing, improving, inhibiting the development of and/or treating neuropsychological disorders or malignant tumors, which includes administering the compound expressed by the general formula (I) or (III) or the prodrug of the compound or the pharmaceutically acceptable salt of the compound to a subject. In one or more embodiments, the compound expressed by the general formula (I) or (III) or the prodrug of the compound or the pharmaceutically acceptable salt of the compound may be administered according to the method for using the pharmaceutical composition I. Examples of the subject include humans and animals other than humans.

The present disclosure may relate to one or more embodiments below.

[A1] A compound expressed by the following general formula (I) or a prodrug of the compound or a pharmaceutically acceptable salt of the compound:

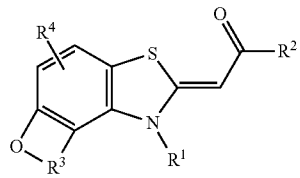
(I)

(where, in the general formula (I), $R^1$ and $R^2$ each independently represent a hydrogen atom or a $C_{1-6}$ hydrocarbon chain, $R^3$ represents

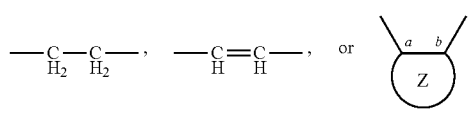

where Z and atoms marked with a and b form a ring selected from the group consisting of one benzene ring, one heteroaromatic ring, an aromatic ring in which one or more benzene rings are condensed, a heteroaromatic ring in which one or more heteroaromatic rings are condensed, a mixed condensed polycyclic ring in which one or more benzene rings are condensed with one or more heteroaromatic rings, and a cyclic aliphatic, and the ring may have at least one substituent that is a hydrogen atom, a halogen atom, or a $C_{1-6}$ alkyl group, and $R^4$ represents a hydrogen atom, a halogen atom, or a $C_{1-6}$ alkyl group).

[A2] A compound expressed by

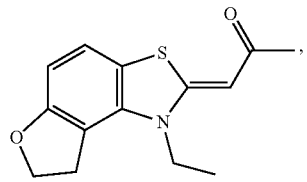

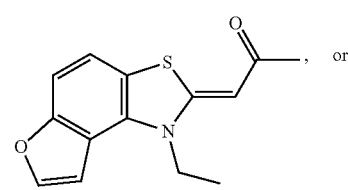, or

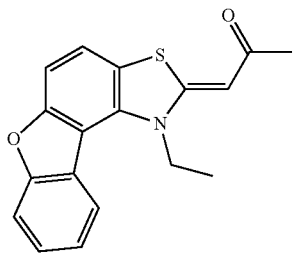

or a prodrug of the compound or a pharmaceutically acceptable salt of the compound.

[A3] A compound expressed by the following general formula (III) or a prodrug of the compound or a pharmaceutically acceptable salt of the compound:

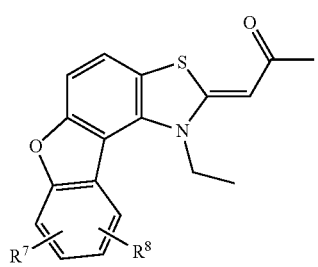
(III)

(where, in the general formula (III), $R^7$ and $R^8$ each independently represent a hydrogen atom, a halogen atom, or a linear, branched, or cyclic $C_{1-6}$ alkyl group).

[A4] A compound expressed by

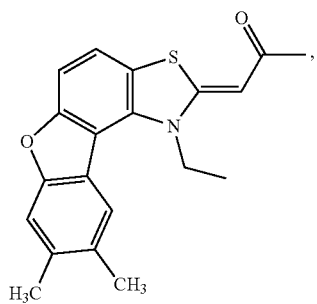,

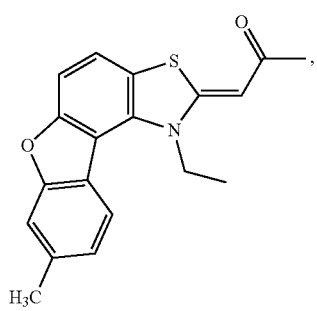,

-continued

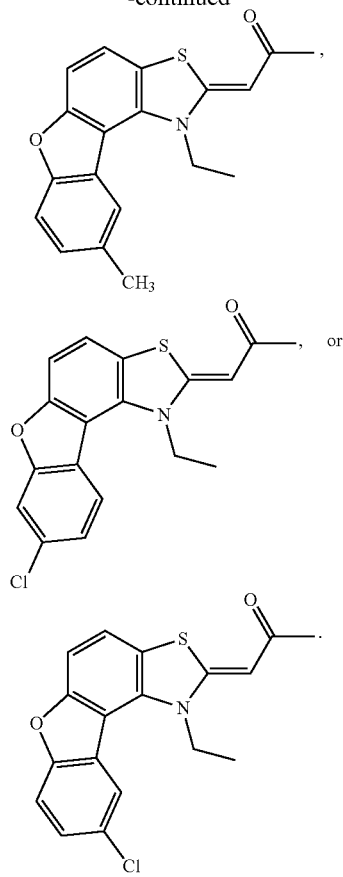

or a prodrug of the compound or a pharmaceutically acceptable salt of the compound.

[A5] A pharmaceutical composition containing the compound or the prodrug of the compound or the pharmaceutically acceptable salt of the compound according to any one of [A1] to [A4] as an active ingredient.

[A6] A pharmaceutical composition for preventing, improving, inhibiting the development of and/or treating neuropsychological disorders or malignant tumors, the pharmaceutical composition containing the compound or the prodrug of the compound or the pharmaceutically acceptable salt of the compound according to any one of [A1] to [A4] as an active ingredient.

[A7] The compound or the prodrug of the compound or the pharmaceutically acceptable salt of the compound according to any one of [A1] to [A4] for preventing, improving, inhibiting the development of, and/or treating neuropsychological disorders or malignant tumors.

[A8] Use of the compound or the prodrug of the compound or the pharmaceutically acceptable salt of the compound according to any one of [A1] to [A4] in manufacture of a pharmaceutical composition for preventing, improving, inhibiting the development of and/or treating neuropsychological disorders or malignant tumors.

[A9] A method for preventing, improving, inhibiting the development of, and/or treating neuropsychological disorders or malignant tumors, including:
administering a compound expressed by the following general formula (I) or a prodrug of the compound or a pharmaceutically acceptable salt of the compound to a subject:

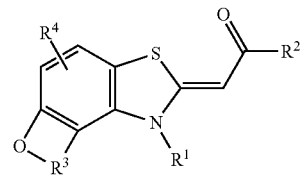

(where, in the general formula (I), $R^1$ and $R^2$ each independently represent a hydrogen atom or a $C_{1-6}$ hydrocarbon chain, $R^3$ represents

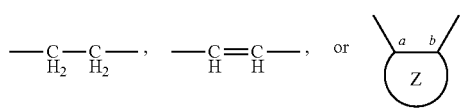

where Z and atoms marked with a and b form a ring selected from the group consisting of one benzene ring, one heteroaromatic ring, an aromatic ring in which one or more benzene rings are condensed, a heteroaromatic ring in which one or more heteroaromatic rings are condensed, a mixed condensed polycyclic ring in which one or more benzene rings are condensed with one or more heteroaromatic rings, and a cyclic aliphatic, and the ring may have at least one substituent that is a hydrogen atom, a halogen atom, or a $C_{1-6}$ alkyl group, and $R^4$ represents a hydrogen atom, a halogen atom, or a $C_{1-6}$ alkyl group).

[A10] A method for preventing, improving, inhibiting the development of, and/or treating neuropsychological disorders or malignant tumors, including:
administering a compound expressed by

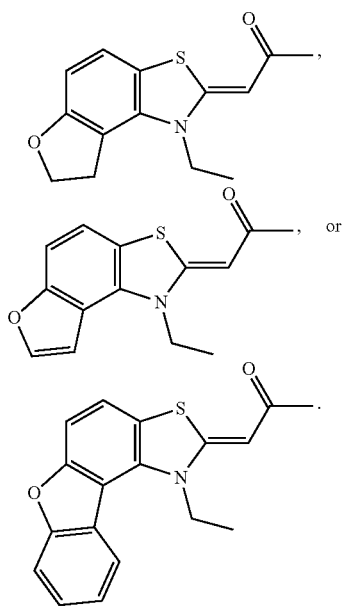

or a prodrug of the compound or a pharmaceutically acceptable salt of the compound to a subject.

[A11] A method for preventing, improving, inhibiting the development of, and/or treating neuropsychological disorders or malignant tumors, including:

administering a compound expressed by the following general formula (III) or a prodrug of the compound or a pharmaceutically acceptable salt of the compound to a subject:

(III)

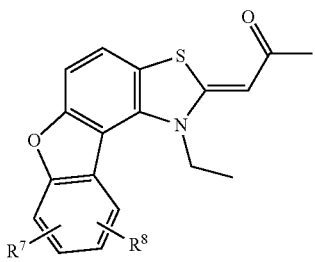

(where, in the general formula (III), R⁷ and R⁸ each independently represent a hydrogen atom, a halogen atom, or a linear, branched, or cyclic $C_{1-6}$ alkyl group).

[A12] A method for preventing, improving, inhibiting the development of, and/or treating neuropsychological disorders or malignant tumors, including:
administering a compound expressed by

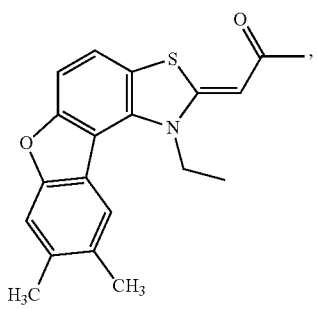

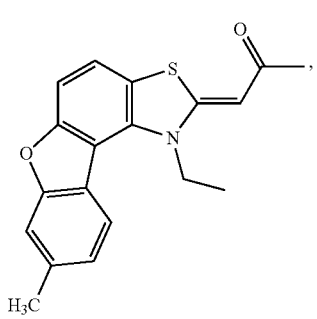

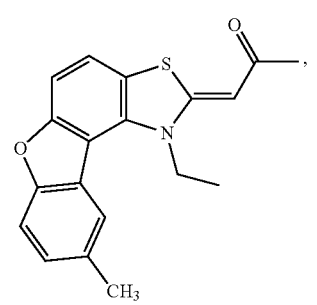

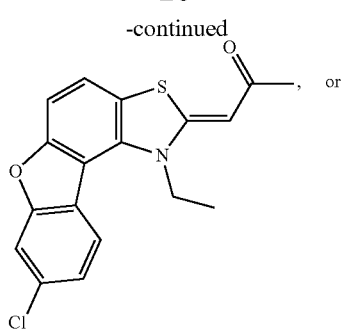

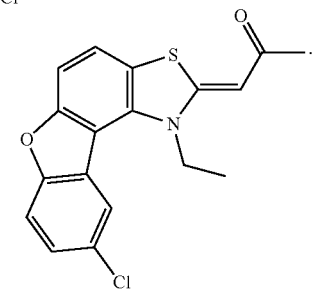

or a prodrug of the compound or a pharmaceutically acceptable salt of the compound to a subject.

[A13] The compound or the prodrug of the compound or the salt of the compound, the pharmaceutical composition, the use, or the method according to any one of [A1] to [A12], wherein the neuropsychological disorders include Down's syndrome, Alzheimer's disease, and/or Alzheimer's disease that can be seen in Down's syndrome.

[A14] The compound or the prodrug of the compound or the salt of the compound, the pharmaceutical composition, the use, or the method according to any one of [A1] to [A12], wherein the malignant tumors are selected from the group consisting of brain tumor, glioblastoma, pancreatic duct cancer, rhabdomyosarcoma, lung cancer, pancreatic cancer, colon cancer, skin cancer, prostatic cancer, breast cancer, and ovarian cancer.

[A15] The compound or the prodrug of the compound or the salt of the compound, the pharmaceutical composition, the use, or the method according to any one of [A1] to [A12], wherein the malignant tumors are selected from the group consisting of the following: (i) existing drug-resistant malignant tumors; (ii) malignant tumors that are known or will be known in the future to be prevented, improved, inhibited in their development, and/or treated by suppressing or inhibiting the receptor tyrosine kinase activity; (iii) malignant tumors that are known or will be known in the future to be prevented, improved, inhibited in their development, and/or treated by suppressing or inhibiting the epidermal growth factor receptor (EGFR) tyrosine kinase activity; (iv) malignant tumors for which it is known or will be known in the future that drugs for inhibiting the receptor tyrosine kinase activity or the epidermal growth factor receptor (EGFR) tyrosine kinase activity have no significant effect on the prevention, improvement, inhibition of the development, and/or treatment of the malignant tumors; and (v) malignant tumors for which it is known or will be known in the future that gefitinib has no significant effect on the prevention, improvement, inhibition of the development, and/or treatment of the malignant tumors.

[Compound Expressed by General Formula (II)]

In one or more embodiments, the present disclosure relates to a compound expressed by the following general formula (II) or a prodrug of the compound or a pharmaceutically acceptable salt of the compound:

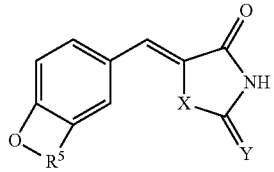
(II)

(where, in the general formula (II), X and Y each independently represent S or NH, $R^5$ represents

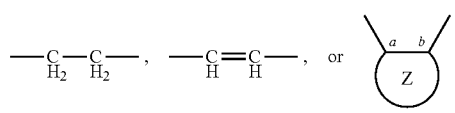

where Z and atoms marked with a and b form a ring selected from the group consisting of one benzene ring, one heteroaromatic ring, an aromatic ring in which one or more benzene rings are condensed, a heteroaromatic ring in which one or more heteroaromatic rings are condensed, a mixed condensed polycyclic ring in which one or more benzene rings are condensed with one or more heteroaromatic rings, and a cyclic aliphatic, and the ring may have at least one substituent that is a hydrogen atom, a halogen atom, or a $C_{1-6}$ alkyl group, and $R^6$ represents a hydrogen atom, a halogen atom, or a $C_{1-6}$ alkyl group).

In one or more embodiments, X of the general formula (II) represents S or NH. Moreover, in one or more embodiments, Y of the general formula (II) represents S or NH. In one or more embodiments, $R^5$ of the general formula (II) represents

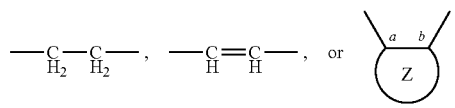

where, in one or more embodiments, Z and atoms marked with a and b form one benzene ring. In one or more embodiments, $R^6$ of the general formula (II) represents a hydrogen atom.

In one or more embodiments, the compound of the general formula (II) is a compound expressed by

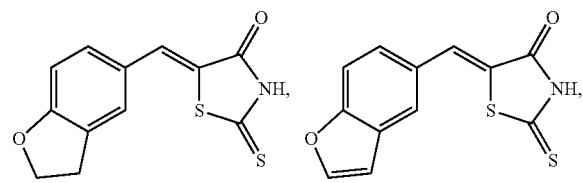

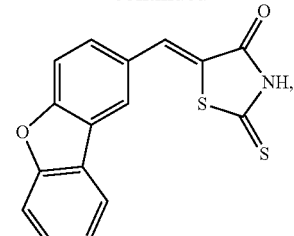

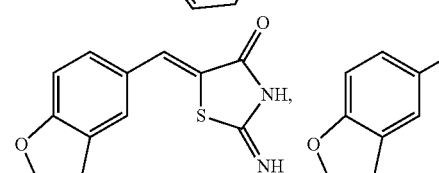

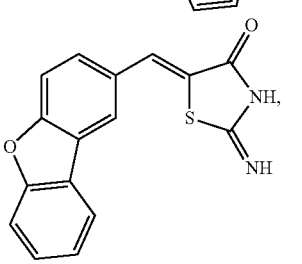

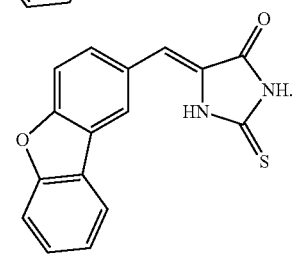

[Prevention, Improvement, Inhibition of Development, and/or Treatment of Neuropsychological Disorders or Malignant Tumors]

A compound expressed by the general formula (II) or a prodrug of the compound or a pharmaceutically acceptable salt of the compound is effective in preventing, improving, inhibiting the development of and/or treating neuropsychological disorders or malignant tumors. This mechanism is estimated as follows. The compound of the general formula (II) or the pharmaceutically acceptable salt of the compound can inhibit not only abnormal phosphorylation of tau protein, but also phosphorylation of amyloid precursor protein (APP), and thus can inhibit the production of amyloid β (Aβ) peptide. Accordingly, neuropsychological disorders may be prevented, improved, inhibited in their development, and/or treated. Moreover, due to the effect of inhibiting the activity of phosphoenzymes, malignant tumors may be prevented, improved, inhibited in their development, and/or treated. However, the present disclosure should not be limited to the above estimation. In one or more embodiments, the compound of the general formula (II) or the prodrug of the compound or the pharmaceutically acceptable salt of the compound exhibits intracerebral transferability and oral absorbability. These properties can more effectively prevent, improve, inhibit the development of, and/or treat neuropsychological disorders or malignant tumors.

In one or more embodiments, the present disclosure relates to a compound expressed by the general formula (II) or a prodrug of the compound or a pharmaceutically acceptable salt of the compound for preventing, improving, inhibiting the development of and/or treating neuropsychological disorders or malignant tumors. In one or more embodiments, the present disclosure relates to a pharmaceutical composition containing the compound expressed by the general formula (II) or the pharmaceutically acceptable salt of the compound as an active ingredient. In one or more embodiments, the present disclosure relates to a pharmaceutical composition (also referred to as a "pharmaceutical composition II of the present disclosure" in the following) for preventing, improving, inhibiting the development of, and/or treating neuropsychological disorders or malignant tumors, which contains the compound expressed by the general formula (II) or the pharmaceutically acceptable salt of the compound as an active ingredient. Moreover, in one or more embodiments, the present disclosure relates to the use of the compound expressed by the general formula (II) or the prodrug of the compound or the pharmaceutically acceptable salt of the compound in manufacture of a pharmaceutical composition for preventing, improving, inhibiting the development of, and/or treating neuropsychological disorders or malignant tumors.

The method for using the pharmaceutical composition II of the present disclosure may differ depending on symptoms, ages, administration methods, etc. The method allows the pharmaceutical composition II to be intermittently or continuously administered (but not limited thereto) orally, endermically, submucosally, subcutaneously, intramuscularly, intravascularly, intracerebrally, or intraperitoneally so that the concentration of the compound (active ingredient) of the general formula (II) in the body is in the range of 100 nM to 1 mM. In a non-limiting embodiment, for oral administration, the pharmaceutical composition II may be administered to a subject (e.g., an adult human) in a dosage of 0.01 mg (preferably 0.1 mg) to 2000 mg (preferably 500 mg and more preferably 100 mg), which is expressed in terms of the compound of the general formula (II), once or several times a day based on the symptom. In a non-limiting embodiment, for intravenous administration, the pharmaceutical composition II may be administered to a subject (e.g., an adult human) in a dosage of 0.001 mg (preferably 0.01 mg) to 500 mg (preferably 50 mg) once or several times a day based on the symptom.

In one or more embodiments, the present disclosure relates to a method for preventing, improving, inhibiting the development of, and/or treating neuropsychological disorders or malignant tumors, which includes administering the compound expressed by the general formula (II) or the prodrug of the compound or the pharmaceutically acceptable salt of the compound to a subject. In one or more embodiments, the compound expressed by the general formula (II) or the prodrug of the compound or the pharmaceutically acceptable salt of the compound may be administered according to the method for using the pharmaceutical composition II. Examples of the subject include humans and animals other than humans.

The present disclosure may relate to one or more embodiments below.

[B1] A compound expressed by the following general formula (II) or a prodrug of the compound or a pharmaceutically acceptable salt of the compound:

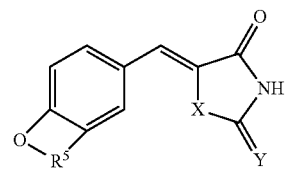

(where, in the general formula (II), X and Y each independently represent S or NH,
R⁵ represents

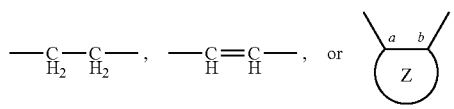

where Z and atoms marked with a and b form a ring selected from the group consisting of one benzene ring, one heteroaromatic ring, an aromatic ring in which one or more benzene rings are condensed, a heteroaromatic ring in which one or more heteroaromatic rings are condensed, a mixed condensed polycyclic ring in which one or more benzene rings are condensed with one or more heteroaromatic rings, and a cyclic aliphatic, and the ring may have at least one substituent that is a hydrogen atom, a halogen atom, or a $C_{1-6}$ alkyl group, and R⁶ represents a hydrogen atom, a halogen atom, or a $C_{1-6}$ alkyl group).

[B2] A compound expressed by

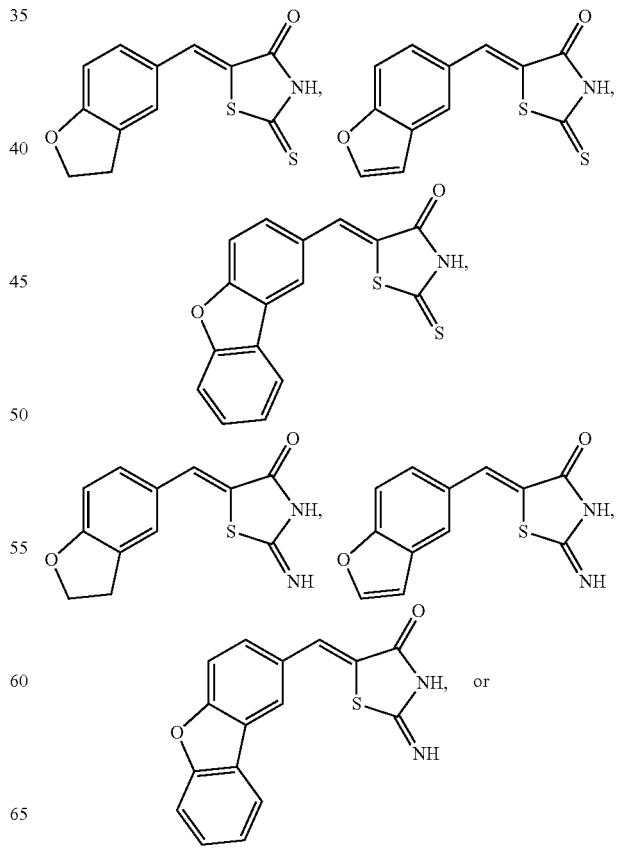

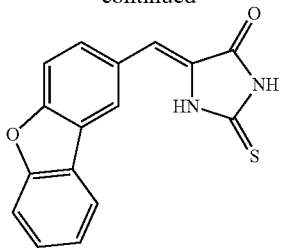

or a prodrug of the compound or a pharmaceutically acceptable salt of the compound.

[B3] A pharmaceutical composition containing the compound or the prodrug of the compound or the pharmaceutically acceptable salt of the compound according to [B1] or [B2] as an active ingredient.

[B4] A pharmaceutical composition for preventing, improving, inhibiting the development of and/or treating neuropsychological disorders or malignant tumors, the pharmaceutical composition containing the compound or the prodrug of the compound or the pharmaceutically acceptable salt of the compound according to [B1] or [B2] as an active ingredient.

[B5] The compound or the prodrug of the compound or the pharmaceutically acceptable salt of the compound according to [B1] or [B2] for preventing, improving, inhibiting the development of and/or treating neuropsychological disorders or malignant tumors.

[B6] Use of the compound or the prodrug of the compound or the pharmaceutically acceptable salt of the compound according to [B1] or [B2] in manufacture of a pharmaceutical composition for preventing, improving, inhibiting the development of, and/or treating neuropsychological disorders or malignant tumors.

[B7] A method for preventing, improving, inhibiting the development of, and/or treating neuropsychological disorders or malignant tumors, including:

administering a compound expressed by the following general formula (II) or a prodrug of the compound or a pharmaceutically acceptable salt of the compound to a subject:

(II)

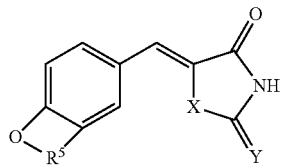

(where, in the general formula (II), X and Y each independently represent S or NH, $R^5$ represents

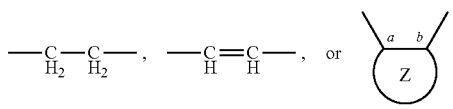

where Z and atoms marked with a and b form a ring selected from the group consisting of one benzene ring, one heteroaromatic ring, an aromatic ring in which one or more benzene rings are condensed, a heteroaromatic ring in which one or more heteroaromatic rings are condensed, a mixed condensed polycyclic ring in which one or more benzene rings are condensed with one or more heteroaromatic rings, and a cyclic aliphatic, and the ring may have at least one substituent that is a hydrogen atom, a halogen atom, or a $C_{1-6}$ alkyl group, and $R^6$ represents a hydrogen atom, a halogen atom, or a $C_{1-6}$ alkyl group).

[B8] A method for preventing, improving, inhibiting the development of, and/or treating neuropsychological disorders or malignant tumors, including:

administering a compound expressed by

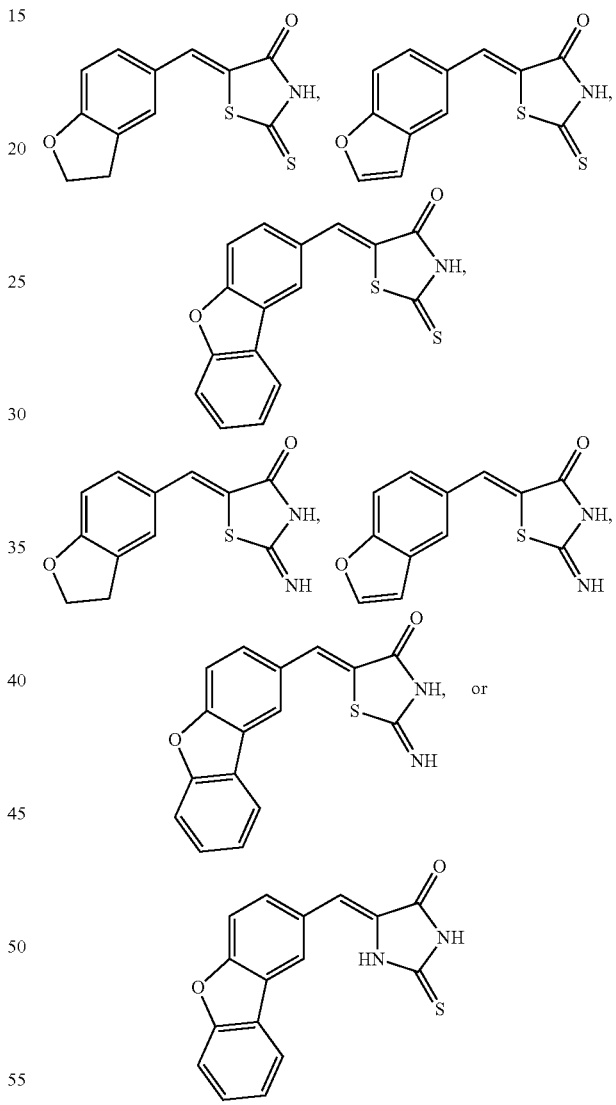

or a prodrug of the compound or a pharmaceutically acceptable salt of the compound to a subject.

[B9] The compound or the prodrug of the compound or the salt of the compound, the pharmaceutical composition, the use, or the method according to any one of [B1] to [B8], wherein the neuropsychological disorders include Down's syndrome, Alzheimer's disease, and/or Alzheimer's disease that can be seen in Down's syndrome.

[B10] The compound or the prodrug of the compound or the salt of the compound, the pharmaceutical composition, the use, or the method according to any one of [B1] to [B8], wherein the malignant tumors are selected from the group consisting of brain tumor, glioblastoma, pancreatic duct cancer, rhabdomyosarcoma, lung cancer, pancreatic cancer, colon cancer, skin cancer, prostatic cancer, breast cancer, and ovarian cancer.

[B11] The compound or the prodrug of the compound or the salt of the compound, the pharmaceutical composition, the use, or the method according to any one of [B1] to [B8], wherein the malignant tumors are selected from the group consisting of the following: (i) existing drug-resistant malignant tumors; (ii) malignant tumors that are known or will be known in the future to be prevented, improved, inhibited in their development, and/or treated by suppressing or inhibiting the receptor tyrosine kinase activity; (iii) malignant tumors that are known or will be known in the future to be prevented, improved, inhibited in their development, and/or treated by suppressing or inhibiting the epidermal growth factor receptor (EGFR) tyrosine kinase activity; (iv) malignant tumors for which it is known or will be known in the future that drugs for inhibiting the receptor tyrosine kinase activity or the epidermal growth factor receptor (EGFR) tyrosine kinase activity have no significant effect on the prevention, improvement, inhibition of the development, and/or treatment of the malignant tumors; and (v) malignant tumors for which it is known or will be known in the future that gefitinib has no significant effect on the prevention, improvement, inhibition of the development, and/or treatment of the malignant tumors.

EXAMPLES

Hereinafter, the present disclosure will be described in more detail by way of examples, which are for illustrative purposes only. However, the present disclosure is not limited to the examples. All the documents cited in the present disclosure are incorporated herein by reference.

Production Example 1: Production of Compound 1

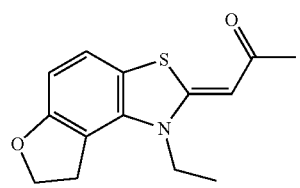

Compound 1

A compound 1 was produced in the following manner.

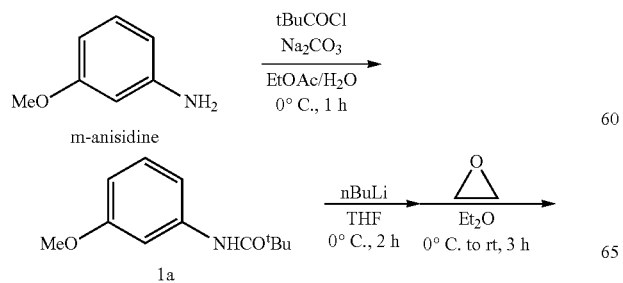

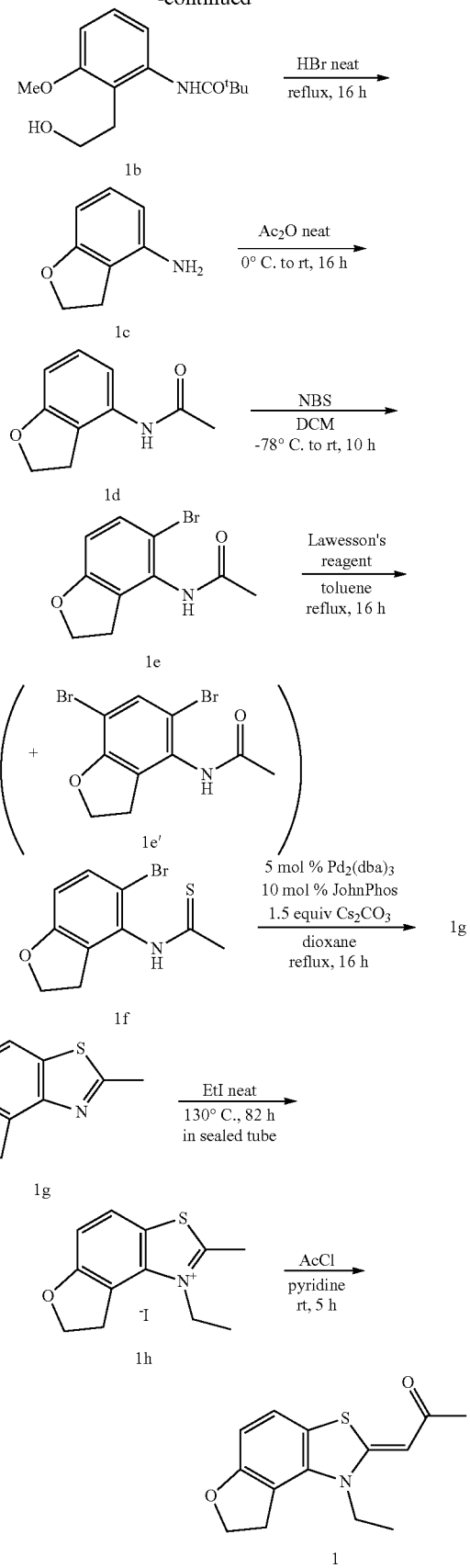

Synthesis of N-(3-methoxyphenyl)pivalamide (1a)

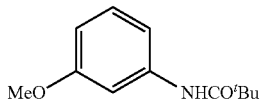

Under the argon atmosphere, pivaloyl chloride (25.0 mL, 205 mmol, commercial product) was slowly dropped at 0° C. into a mixed solution including m-anisidine (21.9 mL, 195 mmol, commercial product), ethyl acetate (EtOAc) (300 mL) of sodium carbonate monohydrate (62.0 g, 500 mmol, commercial product), and purified water (860 mL). After the mixture was stirred at 0° C. for 1 hour, the organic layer was separated and the aqueous layer was extracted with ethyl acetate (EtOAc). The combined organic layer was dried over sodium sulfate and filtered. The filtrate was concentrated under reduced pressure. The residue was recrystallized with ethyl acetate (EtOAc), and thus N-(3-methoxyphenyl)pivalamide (compound 1a) (40.2 g, 194 mmol, 99.5%) was obtained as a colorless solid.

TLC $R_f$=0.50 (n-hexane/EtOAc=6/1)

Synthesis of N-[2-(2-hydroxyethyl)-3-methoxyphenyl]pivalamide (1b)

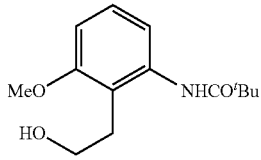

Under the argon atmosphere, n-butyllithium (nBuLi) (2.6 M in THF, 111 mL, 289 mmol, commercial product) was slowly dropped at 0° C. into a tetrahydrofuran (THF) (400 mL, dehydrated, commercial product) solution of the compound 1a (30.0 g, 145 mmol). After the mixture was stirred at 0° C. for 2 hours, ethylene oxide (1.3 M ether solution, 175 mL, 228 mmol, commercial product) was slowly added to the mixture and stirred at 0° C. for 1 hour. The temperature was raised to room temperature, and then the mixture was further stirred for 2 hours. The mixture was concentrated under reduced pressure, to which a saturated ammonium chloride aqueous solution (sat. NH₄Cl aq.) was added. Subsequently, the mixture was extracted with ethyl acetate (EtOAc) (100 mL×4). The combined organic layer was dried over sodium sulfate and filtered. The filtrate was concentrated under reduced pressure. The residue was recrystallized with ethyl acetate (EtOAc), and thus N-[2-(2-hydroxyethyl)-3-methoxyphenyl]pivalamide (compound 1b) (28.1 g, 112 mmol, 77.1%) was obtained as a colorless solid.

TLC $R_f$=0.40 (n-hexane/EtOAc=3/1)

Synthesis of 4-amino-2,3-dihydrobenzofuran (1c)

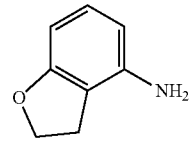

The compound 1b (4.10 g, 16.3 mmol) was dissolved in hydrobromic acid (HBr) (48% aqueous, 20.0 mL, commercial product), and the mixed solution was stirred by heating at 110° C. for 16 hours. After the mixed solution was allowed to cool to room temperature, sodium hydroxide granules were gradually added at 0° C. so that the pH was adjusted to about 9. Subsequently, the mixture was extracted with ethyl acetate (EtOAc) (50 mL×4). The combined organic layer was dried over sodium sulfate and filtered. The filtrate was concentrated under reduced pressure. The residue was purified by a medium-pressure column chromatography (Smart Flash EPCLC W-Prep 2XY system) (n-hexane/EtOAc=1/1), and thus 4-amino-2,3-dihydrobenzofuran (compound 1c) (1.49 g, 11.0 mmol, 67.7%) was obtained as a colorless solid.

TLC $R_f$=0.30 (n-hexane/EtOAc=1/1)

¹H NMR (400 MHz, CDCl₃) δ 6.94 (dd, J=8.4, 8.4 Hz, 1H), 6.28 (dd, J=0.4, 7.6 Hz, 1H), 6.23 (dd, J=0.4, 7.6 Hz, 1H), 4.59 (t, J=8.4 Hz, 2H), 3.60 (brs, 2H), 3.02 (t, J=8.4 Hz, 2H)

Synthesis of 4-acetylamino-2,3-dihydrobenzofuran (1d)

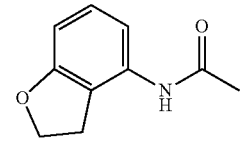

The compound 1c (2.00 g, 14.8 mmol) was dissolved in acetic anhydride (15.0 mL, commercial product), and the mixed solution was stirred at room temperature for 16 hours. After the reaction was completed, the mixture was concentrated under reduced pressure. The resultant brown solid was recrystallized with ethyl acetate (EtOAc), and thus 4-acetylamino-2,3-dihydrobenzofuran (compound 1d) (2.10 g, 11.9 mmol, 80.1%) was obtained as a colorless solid.

TLC $R_f$=0.15 (n-hexane/EtOAc=1/1)

¹H NMR (400 MHz, CDCl₃) δ 7.18 (d, J=6.4 Hz, 1H), 7.09 (t, J=6.4 Hz, 1H), 7.04 (brs, 1H), 6.62 (d, J=6.0 Hz, 1H), 4.59 (t, J=6.8 Hz, 2H), 3.13 (t, J=6.8 Hz, 2H), 2.18 (s, 3H)

Synthesis of 4-acetylamino-5-bromo-2,3-dihydrobenzofuran (1e)

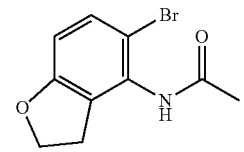

N-bromosuccinimide (2.31 g, 13.0 mmol, commercial product) was gradually added at −78° C. to a dichloromethane (50 ml, dehydrated, commercial product) solution of the compound 1d (2.10 g, 11.9 mmol), and the temperature was raised to room temperature for 10 hours. After the reaction was completed, the mixture was concentrated under reduced pressure. The residue was purified by a medium-pressure column chromatography (Smart Flash EPCLC W-Prep 2XY system) (n-hexane/EtOAc=1/1), and thus 4-acetylamino-5-bromo-2,3-dihydrobenzofuran (compound 1e) (1.76 g, 6.87 mmol, 57.8%) was obtained as a colorless solid. In this case, $^1$H NMR analysis confirmed the by-production of a product (TLC R$_f$=0.15 (n-hexane/EtOAc=1/1)) that can be a dibromo body 1e'.

TLC R$_f$=0.25 (n-hexane/EtOAc=1/1)
$^1$H NMR (400 MHz, CDCl$_3$) δ 7.29 (d, J=8.4 Hz, 1H), 7.11 (brs, 1H), 6.58 (d, J=8.4 Hz, 1H), 4.60 (t, J=8.8 Hz, 2H), 3.22 (t, J=8.8 Hz, 2H), 2.23 (s, 3H)

Synthesis of 5-bromo-4-thioacetylamino-2,3-dihydrobenzofuran (1f)

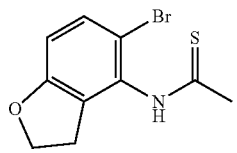

The compound 1e (1.76 g, 6.87 mmol) and a Lawesson's reagent (1.01 g, 2.50 mmol, commercial product) were dissolved in toluene (25 mL, dehydrated, commercial product). The mixture was heated to reflux for 16 hours. After the mixture was allowed to cool to room temperature, the mixture was concentrated under reduced pressure and purified by a medium-pressure column chromatography (Smart Flash EPCLC W-Prep 2XY system) (n-hexane/EtOAc=1/1), and thus 5-bromo-4-thioacetylamino-2,3-dihydrobenzofuran (compound 1f) (1.86 g, 6.83 mmol, 99.5%) was obtained as a light brown solid.

TLC R$_f$=0.35 (n-hexane/EtOAc=1/1)
$^1$H NMR (400 MHz, CDCl$_3$) for a mixture of two rotamers (70:30) δ 8.85 (brs, 0.3H), 8.33 (brs, 0.7H), 7.41 (d, J=8.8 Hz, 0.3H), 7.36 (d, J=8.4 Hz, 0.7H), 6.73 (d, J=8.8 Hz, 0.3H), 6.69 (d, J=8.4 Hz, 0.7H), 4.69-4.59 (m, 2H), 3.19-3.27 (m, 2H), 2.76 (s, 2.1H), 2.36 (s, 0.9H)

Synthesis of 2-methyl-7,8-dihydrobenzofuro[4,5-d]thiazole (1g)

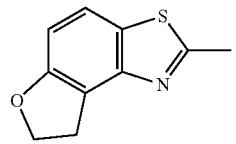

Under the argon atmosphere, trisdibenzylideneacetone (Pd$_2$(dba)$_3$) (237 mg, 0.259 mmol, commercial product), (2-biphenyl)-di-tert-butylphosphine (JohnPhos, 154 mg, 0.516 mmol, commercial product), and cesium carbonate (Cs$_2$CO$_3$) (2.50 g, 7.67 mmol, commercial product) were mixed with dioxane (30 mL, dehydrated, commercial product), and the mixture was stirred for 10 minutes. Then, a dioxane (20 mL, dehydrated, commercial product) solution of the compound 1f (1.40 g, 5.14 mmol) was added to this suspension and heated to reflux for 16 hours. After the mixture was allowed to cool to room temperature, the mixture was concentrated under reduced pressure. The residue was purified by a medium-pressure column chromatography (Smart Flash EPCLC W-Prep 2XY system), and thus 2-methyl-7,8-dihydrobenzofuro[4,5-d]thiazole (compound 1g) (780 mg, 4.08 mmol, 79.2%) was obtained as a light yellow solid.

TLC R$_f$=0.25 (n-hexane/EtOAc=1/1)
$^1$H NMR (400 MHz, CDCl$_3$) δ 7.45 (d, J=8.4 Hz, 1H), 6.82 (d, J=8.4 Hz, 1H), 4.63 (t, J=8.8 Hz, 2H), 3.51 (t, J=8.8 Hz, 2H), 2.75 (s, 3H)

Synthesis of 1-ethyl-2-methyl-7,8-dihydrobenzofuro[4,5-d]thiazol-1-ium iodide (1h)

The compound 1g (182 mg, 0.952 mmol) was dissolved in iodoethane (EtI) (3.0 mL, commercial product), and the mixed solution was stirred by heating at 130° C. (i.e., the temperature of an aluminum heating block) for 82 hours. After the mixed solution was allowed to cool to room temperature, the iodoethane was distilled under reduced pressure, and the precipitated solid was filtered off with a Hirsch funnel. The solid was washed with ethyl acetate (3 mL×4) on the funnel and dried under reduced pressure, and thus 1-ethyl-2-methyl-7,8-dihydrobenzofuro[4,5-d]thiazol-1-ium iodide (compound 1h) (327 mg, 0.942 mmol, 98.9%) was obtained as a light yellow solid.

TLC a tailing spot R$_f$=0.25 (CH$_2$Cl$_2$/MeOH=5/1)
$^1$H NMR (400 MHz, CD$_3$OD) δ 8.00 (d, J=8.8 Hz, 1H), 3.17 (s, 3H), 7.27 (d, J=8.8 Hz, 1H), 4.82 (t, J=8.8 Hz, 2H), 4.76 (q, J=7.2 Hz, 2H), 3.86 (t, J=8.8 Hz, 2H), 1.59 (t, J=7.2 Hz, 3H)

Synthesis of (Z)-1-[1-ethyl-7,8-dihydrobenzofuro[4,5-d]thiazol-2(1H)-ylidene]propan-2-one (Compound 1)

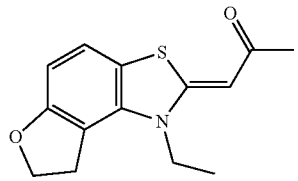 [SMILES: CCN1/C(=C/C(C)=O)Sc2ccc3c(c21)CCO3]

Under the argon atmosphere, acetyl chloride (61 μL, 0.86 mmol, commercial product) was added at 0° C. to a pyridine (4.0 mL, commercial product) solution of the compound 1h (150 mg, 0.432 mmol). The temperature was raised to room temperature, and then the mixture was stirred for 5 hours. After the reaction was completed, hydrochloric acid (0.25

M, 25 mL) was added to the mixture. Subsequently, the mixture was extracted with ethyl acetate (EtOAc) (3 mL×4). The combined organic layer was dried over sodium sulfate and filtered. The filtrate was concentrated under reduced pressure. The residue was purified by a medium-pressure column chromatography (Smart Flash EPCLC W-Prep 2XY system) (n-hexane/EtOAc=1/1), and thus (Z)-1-[1-ethyl-7,8-dihydrobenzofuro[4,5-d]thiazol-2(1H)-ylidene]propan-2-one (compound 1) (57.9 mg, 0.222 mmol, 51.3%) was obtained as a light yellow solid. This solid was recrystallized with acetonitrile, so that a light yellow crystal was produced.

TLC $R_f$=0.25 (n-hexane/EtOAc=1/1)

mp 226-227° C.

$^1$H NMR (500 MHz, CDCl$_3$) δ 7.29 (d, J=8.5 Hz, 1H), 6.67 (d, J=8.5 Hz, 1H), 5.84 (s, 1H), 4.65 (t, J=8.5 Hz, 2H), 4.12 (q, J=7.0 Hz, 2H), 3.55 (t, J=8.5 Hz, 2H), 2.23 (s, 3H), 1.40 (t, J=7.0 Hz, 3H)

Production Example 2: Production of Compound 2

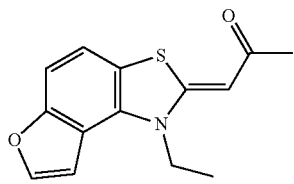

Compound 2

A compound 2 was produced in the following manner.

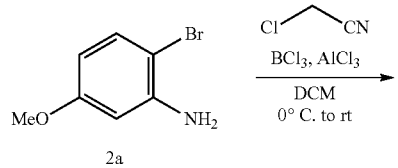

2a

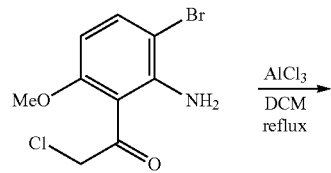

2b

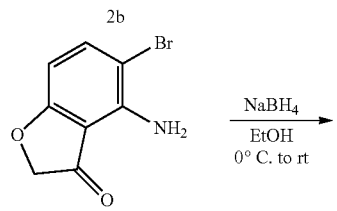

2c

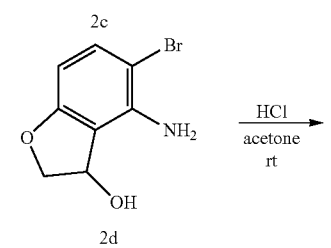

2d

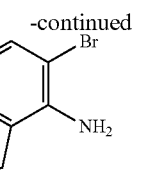

2e

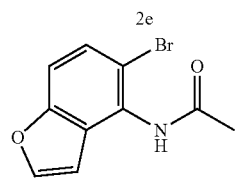

2f

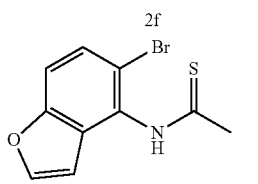

2g

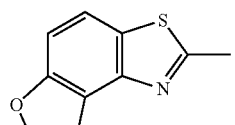

2h

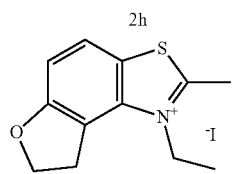

2i

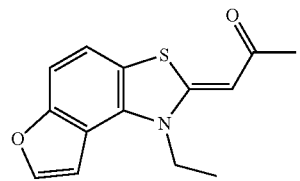

2

Synthesis of 1-(2-amino-3-bromo-6-methoxyphenyl)-2-chloroethanone (Compound 2b)

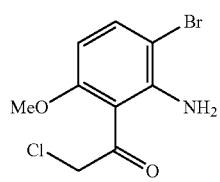

A dichloromethane (500 mL) solution of 2-bromo-5-methoxyphenylamine (compound 2a) (100 g, 0.495 mol) was slowly dropped at 0° C. into a dichloromethane (540 mL) solution of boron trichloride (BCl$_3$) (1M hexane solution, 540 mL, 0.540 mol). The resultant black reaction solution was stirred at 0° C. for 30 minutes, and chloroacetonitrile (76 mL, 1.2 mol) and aluminum chloride (AlCl$_3$) (72 g, 0.54 mol) were added to the solution. The mixture was stirred at room temperature for 1 hour, and then heated to reflux overnight. After the reaction was completed, the mixture was ice-cooled to 0° C., and hydrochloric acid (2 M, 100 mL) was added to the mixture. Then, hydrochloric acid (5 M, 200 mL) was further added to the mixture and stirred at room temperature for 1 hour. The organic layer was collected and the aqueous layer was extracted with dichloromethane. The combined organic layer was washed with water, dried over sodium sulfate, and filtered. The filtrate was concentrated under reduced pressure, and thus 1-(2-amino-3-bromo-6-methoxyphenyl)-2-chloroethanone (compound 2b) (138 g, 0.495 mol, 100%) was obtained as a dark green solid.

$^1$H NMR (400 MHz, CDCl$_3$) δ 7.46 (d, J=8.8 Hz, 1H), 6.74 (brs, 2H), 6.11 (d, J=8.8 Hz, 1H), 4.75 (s, 2H), 3.88 (s, 3H)

Synthesis of 4-amino-5-bromo-benzofuran-3-one (Compound 2c)

A dichloromethane (300 mL) solution of the compound 2b (70 g, 0.25 mol) was slowly dropped into a dichloromethane (400 mL, dehydrated) suspension of aluminum chloride (AlCl$_3$) (100 g, 0.75 mol). The mixture was heated to reflux for 12 hours. After the reaction was completed, the mixture was ice-cooled to 0° C., and hydrochloric acid (2 M) was slowly dropped into the mixture, followed by the addition of methanol and dichloromethane. The organic layer was collected and the aqueous layer was extracted with dichloromethane. The combined organic layer was dried over sodium sulfate and filtered. The filtrate was concentrated under reduced pressure and purified by a silica gel column chromatography, and thus 4-amino-5-bromo-benzofuran-3-one (compound 2c) (30 g, 0.13 mol, 53%) was obtained as a green-brown solid.

$^1$H NMR (400 MHz, CDCl$_3$) δ 7.49 (d, J=8.8 Hz, 1H), 6.28 (d, J=8.8 Hz, 1H), 5.78 (brs, 2H), 4.63 (s, 2H)

Synthesis of 4-amino-5-bromo-2,3-dihydrobenzofuran-3-ol (Compound 2d)

Sodium borohydride (NaBH$_4$) (47 g, 1.2 mol) was added at 0° C. to an ethanol (EtOH) (3 L) solution of the compound 2c (140 g, 0.614 mol). The temperature was raised to room temperature, and then the mixture was stirred overnight. After the reaction was completed, acetone was added to the mixture and stirred at room temperature for 30 minutes. The mixture was concentrated under reduced pressure. Subsequently, water was added to the mixture, and the mixture was extracted with dichloromethane (1000 mL×2). The combined organic layer was dried over sodium sulfate and filtered. The filtrate was concentrated under reduced pressure, and thus 4-amino-5-bromo-2,3-dihydrobenzofuran-3-ol (compound 2d) was obtained as a colorless solid. This compound was used for the next reaction without purification.

$^1$H NMR (400 MHz, CDCl$_3$) δ 7.28 (d, J=8.4 Hz, 1H), 6.18 (d, J=8.4 Hz, 1H), 5.42 (brs, 1H), 4.64-4.60 (m, 1H), 4.42-4.39 (m, 3H), 1.81 (brs, 1H)

Synthesis of 4-amino-5-bromobenzofuran (Compound 2e)

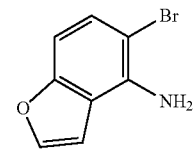 [SMILES: Nc1c(Br)ccc2occc12]

Hydrochloric acid (1M, 100 mL) was added to an acetone solution of the compound 2d (<0.614 mol) and stirred at room temperature for 30 minutes. The mixture was concentrated under reduced pressure, and then diluted with dichloromethane and water. The organic layer was dried over sodium sulfate and filtered. The filtrate was concentrated under reduced pressure, and thus 4-amino-5-bromobenzofuran (compound 2e) was obtained as a yellow solid. This compound was used for the next reaction without purification.

$^1$H NMR (400 MHz, CDCl$_3$) δ 7.52 (d, J=2.4 Hz, 1H), 7.30 (d, J=8.8 Hz, 1H), 6.84 (d, J=8.8 Hz, 1H), 6.67 (d, J=2.4 Hz, 1H), 4.33-4.29 (brs, 2H)

Synthesis of 4-acetamino-5-bromobenzofuran (Compound 2f)

An acetic anhydride (1.5 L) solution of the compound 2e (<0.614 mol) was stirred at room temperature for 2 hours. The precipitated colorless solid was filtered off, and the filtrate was concentrated under reduced pressure. Then, the residue was purified by recrystallization. The solid obtained by the filtration and the solid obtained by the recrystallization were combined and dried, and thus 4-acetamino-5-bromobenzofuran (compound 2f) (120 g, 0.47 mol, 77%, for 3 steps) was obtained.

$^1$H NMR (400 MHz, CDCl$_3$) δ 7.56 (d, J=2.0 Hz, 1H), 7.49 (brs, 1H), 7.42 (d, J=8.8 Hz, 1H), 7.23 (d, J=8.8 Hz, 1H), 6.73 (d, J=2.0 Hz, 1H), 2.27 (s, 3H)

Synthesis of 4-(thioacetyl)amino-5-bromobenzofuran (Compound 2g)

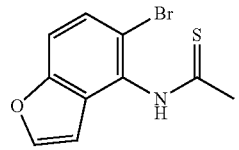

A toluene (2 L) solution of the compound 2f (120 g, 0.472 mol) and Lawesson's reagent (76 g, 0.19 mol) was heated to reflux for 16 hours. After the mixture was allowed to cool to room temperature, the mixture was concentrated under reduced pressure. The residue was purified by a silica gel column chromatography, and thus 4-(thioacetyl)amino-5-bromobenzofuran (compound 2g) (98 g, 0.36 mol, 77%) was obtained as a light yellow solid.

$^1$H NMR (300 MHz, DMSO-$d_6$) δ 11.60 (brs, 1H), 8.01 (d, J=2.1 Hz, 1H), 7.56 (s, 2H), 6.77 (d, J=2.1 Hz, 1H), 2.66 (s, 3H)

Synthesis of 2-methyl-7,8-benzofuro[4,5-d]thiazole (Compound 2h)

Under the nitrogen atmosphere, the compound 2g (98 g, 0.36 mol) was added to a dioxane (1.5 L) suspension of tris(dibenzylideneacetone)dipalladium (Pd$_2$(dba)$_3$) (33 g, 36 mmol), XantPhos (9,9-dimethyl-4,5-bis(diphenylphosphino)xanthene) (41 g, 71 mmol), and cesium carbonate (234 g, 0.72 mol). The mixture was heated to reflux for 16 hours. After the mixture was allowed to cool to room temperature, the mixture was concentrated under reduced pressure. The residue was partially purified (EtOAc) with florisil. The resultant solution was concentrated under reduced pressure and purified by a silica gel column chromatography, and thus 2-methyl-7,8-benzofuro[4,5-d]thiazole (compound 2 h) (60 g, 0.32 mol, 88%) was obtained as a yellow solid.

$^1$H NMR (300 MHz, CDCl$_3$) δ 7.73 (d, J=2.1 Hz, 1H), 7.67 (d, J=8.7 Hz, 1H), 7.53 (d, J=8.7 Hz, 1H), 7.28 (d, J=2.1 Hz, 1H), 2.90 (s, 3H)

Synthesis of 1-ethyl-2-methyl-7,8-benzofuro[4,5-d]thiazol-1-ium iodide (Compound 2i)

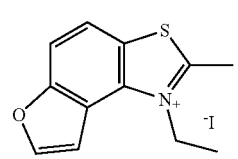

An iodoethane (400 mL) solution of the compound 2h (50 g, 0.26 mol) was tightly sealed and stirred by heating at 130° C. for 50 hours in an autoclave. After the solution was allowed to cool to room temperature, the solution was concentrated under reduced pressure to remove the iodoethane. The residue was suspended in ethyl acetate. This suspension was filtered and the residue was washed with ethyl acetate, and thus 1-ethyl-2-methyl-7,8-benzofuro[4,5-d]thiazol-1-ium iodide (compound 2i) (66 g, 0.19 mol, 74%) was obtained as a green solid.

$^1$H NMR (400 MHz, DMSO-$d_6$) δ 8.49 (d, J=2.1 Hz, 1H), 8.36 (d, J=8.8 Hz, 1H), 8.16 (d, J=8.8 Hz, 1H), 7.77 (d, J=2.1 Hz, 1H), 4.90 (q, J=7.2 Hz, 2H), 3.26 (s, 3H), 1.53 (t, J=7.2 Hz, 3H)

Synthesis of (Z)-1-[1-ethyl-7,8-benzofuro[4,5-d]thiazol-2(1H)-ylidene]propan-2-one (Compound 2)

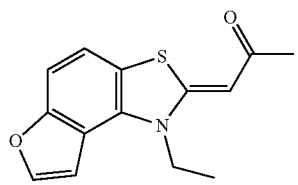 [SMILES: CCN1/C(=C/C(C)=O)Sc2ccc3occc3c21]

Acetic anhydride (43 mL, 0.46 mol) and triethylamine (80 mL, 0.57 mol) were added to an acetonitrile (250 mL) suspension of the compound 2i (66 g, 0.19 mol). The mixture was heated to reflux for 3 hours. After the mixture was allowed to cool to room temperature, the mixture was concentrated under reduced pressure. The residue was purified by a silica gel column chromatography (petroleum ether/EtOAc=1/1), and thus (Z)-1-[1-ethyl-7,8-benzofuro[4,5-d]thiazol-2(1H)-ylidene]propan-2-one (compound 2) (42 g, 0.16 mol, 84%) was obtained as a yellow solid.

$^1$H NMR (400 MHz, CDCl$_3$) δ 7.71 (t, J=1.2 Hz, 1H), 7.44 (d, J=8.8 Hz, 1H), 7.33 (dd, J=8.8, 0.9 Hz, 1H), 6.94 (dd, J=2.1, 0.9 Hz, 1H), 5.92 (s, 1H), 4.27 (q, J=7.2 Hz, 2H), 2.24 (s, 3H), 1.47 (t, J=7.2 Hz, 3H)

Production Example 3: Production of Compound 3

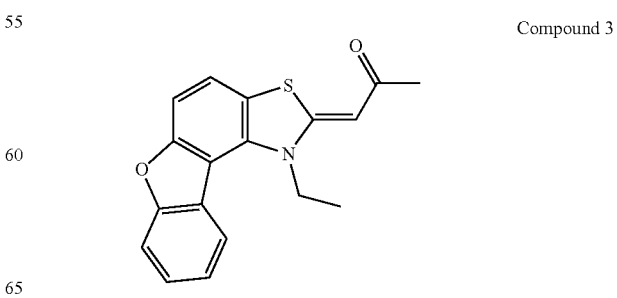

A compound 3 was produced in the following manner.

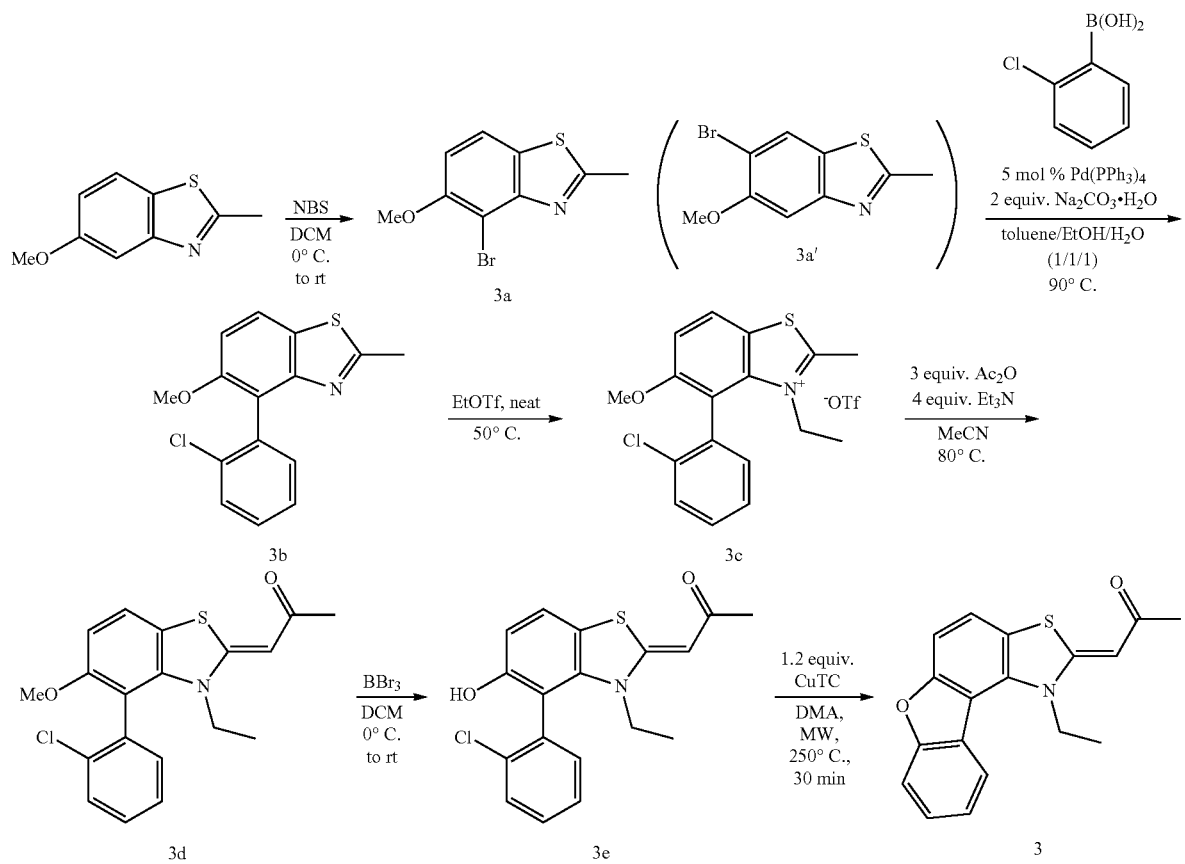

Synthesis of 4-bromo-5-methoxy-2-methylbenzo[d]thiazole (Compound 3a)

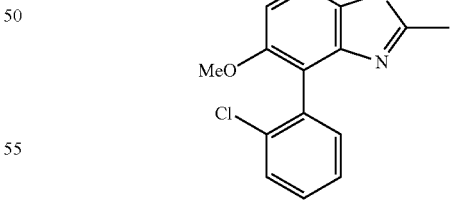

N-bromosuccinimide (6.05 g, 34.0 mmol, commercial product) was gradually added at 0° C. to a dichloromethane (60 mL, dehydrated, commercial product) solution of 5-methoxy-2-methylbenzo[d]thiazole (5.54 g, 30.9 mmol, commercial product). The mixture was stirred at room temperature for 40 hours. After the reaction was completed, a sodium thiosulfate aqueous solution (5 mL) was added to the mixture. Subsequently, the mixture was extracted with dichloromethane. The organic layer was dried over sodium sulfate and filtered. The filtrate was concentrated under reduced pressure and purified by a medium-pressure column chromatography (Smart Flash EPCLC W-Prep 2XY system) (n-hexane/EtOAc=5/1), and thus 4-bromo-5-methoxy-2-methylbenzo[d]thiazole (compound 3a) (7.02 g, 27.2 mmol, 88.0%) was obtained as a colorless solid. In this case, $^1$H NMR analysis confirmed the production of a 6-bromo body 3a' (TLC $R_f$=0.20 (n-hexane/EtOAc=5/1), about 12%) that can be a positional isomer.

TLC $R_f$=0.35 (n-hexane/EtOAc=5/1)

$^1$H NMR (500 MHz, CDCl$_3$) δ 7.68 (d, J=9.0 Hz, 1H, aromatic), 7.02 (d, J=9.0 Hz, 1H, aromatic), 3.98 (s, 3H, OCH$_3$), 2.87 (s, 3H, ArCH$_3$)

$^{13}$C NMR (126 MHz, CDCl$_3$) δ 169.7, 154.9, 153.1, 128.2, 120.3, 110.5, 104.7, 57.2, 20.5

Synthesis of 4-(2-chlorophenyl)-5-methoxy-2-methylbenzo[d]thiazole (Compound 3b)

Under the argon atmosphere, toluene (7.0 mL, dehydrated, commercial product), ethanol (7.0 mL, dehydrated, commercial product), and H$_2$O (7.0 mL) solutions of the compound 3a (516 mg, 2.00 mmol), 2-chlorophenylboronic acid (375 mg, 2.40 mmol, commercial product), tetrakis (triphenylphosphine)palladium (116 mg, 0.100 mmol, commercial product), and sodium carbonate monohydrate (424 mg, 3.42 mmol, commercial product) were stirred by heating at 90° C. for 20 hours. After the mixture was allowed to cool to room temperature, the mixture was partially purified with florisil (75 to 150 μm, commercial product). The resultant solution was concentrated under reduced pressure and purified by a medium-pressure column chromatography (Smart Flash EPCLC W-Prep 2XY system) (n-hexane/EtOAc=5/1), and thus 4-(2-chlorophenyl)-5-methoxy-2-methylbenzo[d]thiazole (compound 3b) (490 mg, 1.69 mmol, 84.5%) was obtained as a light yellow oily matter.

TLC $R_f$=0.35 (n-hexane/EtOAc=5/1)*

*TLC $R_f$=0.45 (triple or quadruple development with n-hexane/EtOAc=10/1), cf. TLC of 3a: $R_f$=0.40 (triple or quadruple development with n-hexane/EtOAc=10/1)

IR (KBr, cm$^{-1}$) 3404, 3057, 2937, 1459, 1395, 1275, 1216, 1100, 749, 642

$^1$H NMR (500 MHz, CDCl$_3$) δ 7.79 (d, J=8.5 Hz, 1H, aromatic), 7.53-7.51 (m, 1H, aromatic), 7.39-7.33 (m, 3H, aromatic), 7.11 (d, J=8.5 Hz, 1H, aromatic), 3.83 (s, 3H, OCH$_3$), 2.74 (s, 3H, hetArCH$_3$)

$^{13}$C NMR (126 MHz, CDCl$_3$) δ 168.2, 155.5, 153.3, 134.8, 134.4, 132.4, 129.4, 128.9, 128.2, 126.4, 121.8, 121.2, 110.0, 56.8, 20.5

Synthesis of 4-(2-chlorophenyl)-3-ethyl-5-methoxy-2-methylbenzo[d]thiazol-3-ium triflate (Compound 3c)

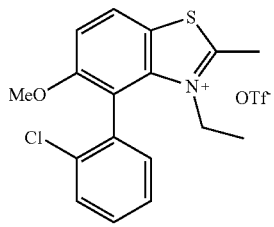

Under the argon atmosphere, the compound 3b (661 mg, 2.28 mmol) was dissolved in ethyl triflate (2.0 mL, commercial product), and the mixed solution was stirred by heating at 50° C. (i.e., the bath temperature) for 17 hours. After the mixed solution was allowed to cool to room temperature, the precipitated crystal was filtered off with a Hirsch funnel. The crystal was washed with n-hexane (3 mL×4), and thus 4-(2-chlorophenyl)-3-ethyl-5-methoxy-2-methylbenzo[d]thiazol-3-ium triflate (compound 3c) (744 mg, 1.59 mmol, 69.7%) was obtained as a light orange solid.

IR (KBr, cm$^{-1}$) 3404, 3057, 2937, 1459, 1395, 1275, 1216, 1100, 749, 642

$^1$H NMR (500 MHz, DMSO-d$_6$) δ 8.52 (d, J=9.0 Hz, 1H, aromatic), 7.74-7.67 (m, 2H, aromatic), 7.61-7.50 (m, 3H, aromatic), 4.15-4.06 (m, 1H, NCH$_{gem-AA}$CH$_3$), 3.98-3.90 (m, 1H, NCH$_{gem-AA}$CH$_3$), 3.81 (s, 3H, OCH$_3$), 3.12 (s, 3H, hetArCH$_3$) 0.99 (t, J=7.0 Hz, 3H, CH$_2$CH$_3$)

$^{13}$C NMR, (126 MHz, DMSO-d$_6$) δ 179.0, 158.2, 138.6, 133.9, 132.7, 131.2, 130.7, 129.6, 127.5, 125.8, 121.9, 120.7 (q, J=324 Hz), 116.1, 113.4, 57.2, 45.6, 17.3, 13.1

Synthesis of (Z)-1-[4-(2-chlorophenyl)-3-ethyl-5-methoxybenzo[d]thiazole-2(3H)-ylidene]propan-2-one (Compound 3d)

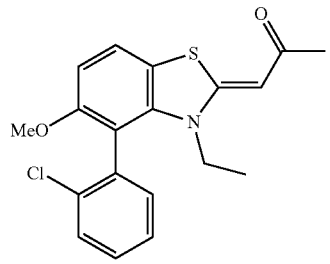 [SMILES: CCN1/C(=C/C(C)=O)Sc2ccc(OC)c(-c3ccccc3Cl)c21]

Under the argon atmosphere, triethylamine (0.56 mL, 4.02 mmol, commercial product) and acetic anhydride (0.28 mL, 2.96 μmol commercial product) were added at room temperature to an acetonitrile (MeCN) (10 mL, dehydrated, commercial product) solution of the compound 3c (468 mg, 1.00 mmol). The mixture was stirred at 80° C. for 2.5 hours. After the reaction was completed, distilled water (about 5 mL) was added to the mixture. Subsequently, the mixture was extracted with dichloromethane (3 mL×4). The combined organic layer was dried over sodium sulfate and filtered. The filtrate was concentrated under reduced pressure and purified by a medium-pressure column chromatography (Smart Flash EPCLC W-Prep 2XY system) (n-hexane/EtOAc=1/1), and thus (Z)-1-[4-(2-chlorophenyl)-3-ethyl-5-methoxybenzo[d]thiazole-2(3H)-ylidene]propan-2-one (compound 3d) (288 mg, 0.800 mmol, 80.0%) was obtained as a light yellow solid.

TLC $R_f$=0.30 (n-hexane/EtOAc=1/1)

IR (KBr, cm$^{-1}$) 2935, 2839, 1458, 1424, 1194, 1091, 1044, 969, 765

$^1$H NMR (500 MHz, CDCl$_3$) δ 7.55-7.50 (m, 2H, aromatic), 7.42-7.31 (m, 3H, aromatic), 6.84 (d, J=9.0 Hz, 1H, aromatic), 5.78 (s, 1H, olefinic), 3.72 (s, 3H, OCH$_3$), 3.65-3.46 (m, 2H, CH$_2$CH$_3$), 2.21 (s, 3H, C(O)CH$_3$), 0.93 (t, J=7.2 Hz, 3H, CH$_2$CH$_3$)

$^{13}$C NMR (126 MHz, CDCl$_3$) δ 191.1, 161.6, 156.8, 137.5, 135.3, 134.0, 132.2, 129.6, 129.4, 126.6, 122.3, 120.3, 112.9, 106.3, 90.7, 56.7, 41.9, 29.1, 11.9

Synthesis of (Z)-1-[4-(2-chlorophenyl)-3-ethyl-5-hydroxybenzo[d]thiazole-2(3H)-ylidene]propan-2-one (Compound 3e)

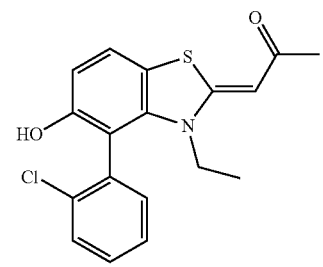 [SMILES: CCN1/C(=C/C(C)=O)Sc2ccc(O)c(-c3ccccc3Cl)c21]

Under the argon atmosphere, boron tribromide (1.0 M dichloromethane solution, 1.20 mL, 1.20 mmol, commercial product) was added at 0° C. to a dichloromethane (4.0 mL, dehydrated, commercial product) solution of the compound 3d (144 mg, 0.400 mmol). The temperature was raised to room temperature, and then the mixture was stirred for 5 hours. After the reaction was completed, distilled water (about 5 mL) was added to the mixture. Subsequently, the mixture was extracted with dichloromethane (3 mL×4) and a small amount of methanol (about 0.5 mL). The combined organic layer was dried over sodium sulfate and filtered. The filtrate was concentrated under reduced pressure and purified by a silica gel column chromatography (n-hexane/EtOAc=1/1), and thus (Z)-1-[4-(2-chlorophenyl)-3-ethyl-5-hydroxybenzo[d]thiazole-2(3H)-ylidene]propan-2-one (compound 3e) (138 mg, 0.399 mmol, 99.8%) was obtained as a yellow solid.

TLC $R_f$=0.20 (n-hexane/EtOAc=1/1, broad spot)

IR (KBr, cm$^{-1}$) 3118, 1473, 1420, 1287, 991, 814, 765

$^1$H NMR (500 MHz, DMSO-d$_6$) δ 9.62 (s, 1H, ArOH), 7.59 (d, J=8.0 Hz, 1H, aromatic), 7.54 (d, J=8.5 Hz, 1H, aromatic), 7.48-7.40 (m, 3H, aromatic), 6.80 (d, J=8.5 Hz, 1H, aromatic), 5.93 (s, 1H, olefinic), 3.63-3.55 (m, 1H, CH$_{AA'\text{-}Gem}$CH$_3$), 3.46-3.38 (m, 1H, CH$_{AA'\text{-}Gem}$CH$_3$), 2.05 (s, 3H, C(O)CH$_3$), 0.81 (t, J=7.0 Hz, 3H, CH$_2$CH$_3$)

$^{13}$C NMR (126 MHz, DMSO-d$_6$) δ 189.9, 160.4, 155.2, 137.4, 134.7, 134.4, 133.2, 130.4, 129.5, 127.5, 122.9, 116.9, 111.5, 111.0, 90.7, 41.7, 29.2, 12.1

Synthesis of (Z)-1-[1-ethylbenzo[2,3]benzofuro[4,5-d]thiazol-2(1H)-ylidene]propan-2-one (Compound 3)

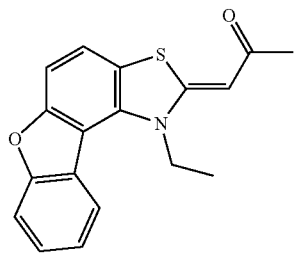 [SMILES: CCN1/C(=C/C(C)=O)Sc2ccc3oc4ccccc4c3c21]

Under the argon atmosphere, an N,N-dimethylacetamide (2 mL, dehydrated, commercial product) solution of the compound 3e (69.2 mg, 0.200 mmol) and copper (I) thiophene-2-carboxylate (45.8 mg, 0.240 mmol, commercial product) was stirred by heating at 250° C. for 30 minutes under microwave irradiation. After the solution was allowed to cool to room temperature, diluted hydrochloric acid (0.1 M, 3 mL) was added to the solution. Subsequently, the mixture was extracted with dichloromethane (3 mL×4). The organic layer was dried over sodium sulfate and filtered. The filtrate was concentrated under reduced pressure and purified by a silica gel column chromatography (n-hexane/EtOAc=1/1), and thus (Z)-1-[1-ethylbenzo[2,3]benzofuro[4,5-d]thiazol-2(1H)-ylidene]propan-2-one (compound 3) (35.3 mg, 0.114 mmol, 57.0%) was obtained as a light brown solid.

TLC $R_f$=0.30 (n-hexane/EtOAc=1/1)

mp 190-192° C.

IR (KBr, cm$^{-1}$) 3058, 2987, 2931, 1346, 1203, 1011, 741, 647, 542

$^1$H NMR (500 MHz, CDCl$_3$) δ 8.07 (d, J=8.5 Hz, 1H, aromatic), 7.67-7.64 (m, 2H, aromatic), 7.52 (dd, J=8.0, 1.5 Hz, 1H, aromatic), 7.46-7.39 (m, 2H, aromatic), 6.05 (s, 1H, olefinic), 4.69 (q, J=7.0 Hz, 2H, CH$_2$CH$_3$), 2.30 (s, 3H, C(O)CH$_3$), 1.75 (t, J=7.0 Hz, 3H, CH$_2$CH$_3$)

$^{13}$C NMR (126 MHz, CDCl$_3$) δ 191.1, 160.7, 156.7, 156.1, 135.2, 127.2, 123.3, 122.6, 121.4, 121.3, 121.1, 112.4, 109.3, 107.0, 90.2, 43.7, 29.1, 14.4

Production Example 4: Production of Compound 4

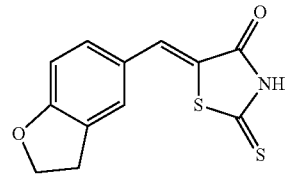

A compound 4 was produced in the following manner.

Synthesis of (Z)-5-[(2,3-dihydrobenzofuran-5-yl)methylene]-2-thioxothiazolidin-4-one (compound 4)

Under the argon atmosphere, acetic acid (AcOH) (120 μL, 2.10 mmol, commercial product) was added at room temperature to an acetonitrile (MeCN) (2 mL, dehydrated, commercial product) solution of 2,3-dihydrobenzofuran-5-carbaldehyde (296 mg, 2.00 mmol, commercial product), ammonium acetate (NH$_4$OAc) (77.0 mg, 1.00 mmol, commercial product), and rhodanine (266 mg, 2.00 mmol, commercial product). The mixture was heated to reflux for 3.5 hours. After the mixture was allowed to cool to room temperature, the precipitated crystal was filtered off with a Hirsch funnel. The crystal was washed with water (3 mL×4) and diethyl ether (3 mL×2), and thus (Z)-5-[(2,3-dihydrobenzofuran-5-yl)methylene]-2-thioxothiazolidin-4-one (compound 4) (488 mg, 1.86 mmol, 92.7%) was obtained as a yellow solid.

mp 247-248° C.

$^1$H NMR (400 MHz, DMSO-ds) δ 13.70 (brs, 1H), 7.58 (s, 1H), 7.47 (s, 1H), 7.41 (d, J=8.4 Hz, 1H), 6.93 (d, J=8.4 Hz, 1H), 4.63 (t, J=8.4 Hz, 2H), 3.25 (t, J=8.4 Hz, 2H)

Production Example 5: Production of Compound 5

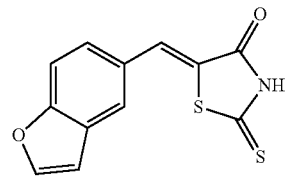

A compound 5 was produced in the following manner.

Synthesis of (Z)-5-[(benzofuran-5-yl)methylene]-2-thioxothiazolidin-4-one (Compound 5)

Under the argon atmosphere, acetic acid (AcOH) (60 μL, 1.1 mmol, commercial product) was added at mom temperature to an acetonitrile (MeCN) (2 mL, dehydrated, commercial product) solution of benzofuran-5-carbaldehyde (146 mg, 1.00 mmol, synthesized according to J. Med. Chem., 2009, 52, 6270-6286), ammonium acetate (NH$_4$OAc) (38.5 mg, 0.500 mmol, commercial product), and rhodanine (133 mg, 1.00 mmol, commercial product). The mixture was heated to reflux for 2 hours. After the mixture was allowed to cool to room temperature, the precipitated crystal was filtered off with a Hirsch funnel. The crystal was washed with water (3 mL×4) and diethyl ether (3 mL×2), and thus (Z)-5-[(benzofuran-5-yl)methylene]-2-thioxothiazolidin-4-one (compound 5) (212 mg, 0.812 mmol, 81.2%) was obtained as a yellow solid.

mp 264-265° C.

$^1$H NMR (400 MHz, DMSO-d$_6$) δ 13.84 (brs, 1H), 8.13 (d, J=2.0 Hz, 1H), 7.96 (d, J=2.0 Hz, 1H), 7.81-7.78 (m, 2H), 7.61 (dd, J=8.8, 2.0 Hz, 1H), 7.12 (d, J=2.0 Hz, 1H)

Production Example 6: Production of Compound 6

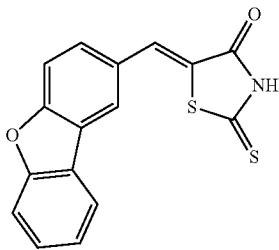

Compound 6

A compound 6 was produced in the following manner.

Synthesis of (Z)-5-[(dibenzo[b,d]furan-2-yl)methylene]-2-thioxothiazolidin-4-one (Compound 6)

Under the argon atmosphere, acetic acid (AcOH) (57 μL, 1.0 mmol, commercial product) was added at room temperature to an acetonitrile (MeCN) (2 mL, dehydrated, commercial product) solution of dibenzofuran-2-carbaldehyde (196 mg, 0.999 mmol, synthesized according to Eur. J. Med. Chem., 2011, 46, 4827-4833), ammonium acetate (NH$_4$OAc) (38.5 mg, 0.499 mmol, commercial product), and rhodanine (133 mg, 0.999 mmol, commercial product). The mixture was heated to reflux for 2 hours. After the mixture was allowed to cool to room temperature, the precipitated crystal was filtered off with a Hirsch funnel. The crystal was washed with water (3 mL×4) and diethyl ether (3 mL×2), and thus (Z)-5-[(dibenzo[b,d]furan-2-yl)methylene]-2-thioxothiazolidin-4-one (compound 6) (351 mg, >0.999 mmol, >100%, purity: about 85%) was obtained as a light yellow solid.

mp 287-288° C.

$^1$H NMR (400 MHz, DMSO-d$_6$) δ 13.85 (brs, 1H, NH), 8.37 (s, 1H, aromatic), 8.29 (d, J=7.2 Hz, 1H, aromatic), 7.88 (d, J=8.4 Hz, 1H, aromatic), 7.82 (s, 1H, olefinic), 7.80-7.74 (m, 2H, aromatic), 7.60 (dd, J=8.4, 0.8 Hz, 1H, aromatic), 7.45 (dd, J=8.4, 1.2 Hz, 1H, aromatic)

Production Example 7: Production of Compound 7

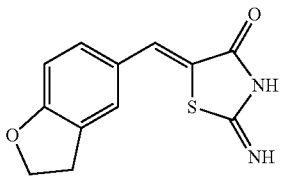

Compound 7

A compound 7 was produced in the following manner.

Synthesis of (Z)-5-[(2,3-dihydrobenzofuran-5-yl)methylene]-2-iminothiazolidin-4-one (Compound 7)

Under the argon atmosphere, acetic acid (AcOH) (120 μL, 2.10 mmol, commercial product) was added at room temperature to an acetonitrile (MeCN) (2 mL, dehydrated, commercial product) solution of 2,3-dihydrobenzofuran-5-carbaldehyde (296 mg, 2.00 mmol, commercial product), ammonium acetate (NH$_4$OAc) (77.0 mg, 1.00 mmol, commercial product), and pseudothiohydantoin (232 mg, 2.00 mmol, commercial product). The mixture was heated to reflux for 6 hours. After the mixture was allowed to cool to room temperature, the precipitated crystal was filtered off with a Hirsch funnel. The crystal was washed with water (3 mL×4) and diethyl ether (3 mL×2), and thus (Z)-5-[(2,3-dihydrobenzofuran-5-yl)methylene]-2-iminothiazolidin-4-one (compound 7) (468 mg, 1.90 mmol, 95.1%) was obtained as a light yellow solid.

mp 280° C. (dec)

$^1$H NMR (400 MHz, DMSO-d$_6$) δ 9.33 (brs, 1H), 9.07 (brs, 1H), 7.55 (s, 1H), 7.46 (s, 1H), 7.36 (dd, J=7.2, 0.8 Hz, 1H), 6.92 (d, J=7.2 Hz, 1H), 4.62 (t, J=7.2 Hz, 2H), 3.26 (t, J=7.2 Hz, 2H)

Production Example 8: Production of Compound 8

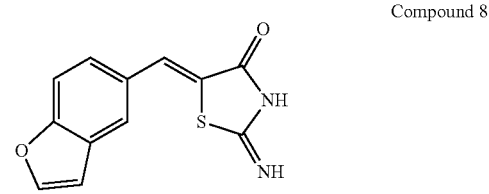 [SMILES: N=C1NC(=O)/C(=C/c2ccc3occc3c2)S1]

Compound 8

A compound 8 was produced in the following manner.

Synthesis of (Z)-5-[(benzofuran-5-yl)methylene]-2-iminothiazolidin-4-one (Compound 8)

Under the argon atmosphere, acetic acid (AcOH) (60 μL, 1.1 mmol, commercial product) was added at room temperature to an acetonitrile (MeCN) (2 mL, dehydrated, commercial product) solution of benzofuran-5-carbaldehyde (146 mg, 1.00 mmol, synthesized according to J. Med. Chem., 2009, 52, 6270-6286), ammonium acetate (NH$_4$OAc) (38.5 mg, 0.500 mmol, commercial product), and pseudothiohydantoin (133 mg, 1.00 mmol, commercial product). The mixture was heated to reflux for 2 hours. After the mixture was allowed to cool to room temperature, the precipitated crystal was filtered off with a Hirsch funnel. The crystal was washed with water (3 mL×4) and diethyl ether (3 mL×2), and thus (Z)-5-[(benzofuran-5-yl)methylene]-2-iminothiazolidin-4-one (compound 8) (94.8 mg, 0.389 mmol, 38.9%) was obtained as a light yellow solid.

mp 250° C. (dec)

$^1$H NMR (400 MHz, DMSO-d$_6$) δ 9.43 (brs, 1H), 9.17 (brs, 1H), 8.13 (d, J=2.0 Hz, 1H), 7.93 (d, J=2.0 Hz, 1H), 7.79-7.76 (m, 2H), 7.59 (dd, J=8.8, 2.0 Hz, 1H), 7.11 (d, J=2.0 Hz, 1H)

Production Example 9: Production of Compound 9

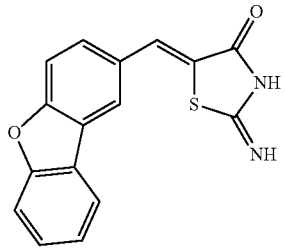

Compound 9

A compound 9 was produced in the following manner.

Synthesis of (Z)-5-[(dibenzo[b,d]furan-2-yl)methylene]-2-iminothiazolidin-4-one (Compound 9)

Under the argon atmosphere, acetic acid (AcOH) (57 μL, 1.0 mmol, commercial product) was added at room temperature to an acetonitrile (MeCN) (2 mL, dehydrated, commercial product) solution of dibenzofuran-2-carbaldehyde (196 mg, 0.999 mmol, synthesized according to Eur. J. Med. Chem., 2011, 46, 4827-4833), ammonium acetate (NH$_4$OAc) (38.5 mg, 0.499 mmol, commercial product), and pseudothiohydantoin (133 mg, 1.15 mmol, commercial product). The mixture was heated to reflux for 2 hours. After the mixture was allowed to cool to room temperature, the precipitated crystal was filtered off with a Hirsch funnel. The crystal was washed with water (3 mL×4) and diethyl ether (3 mL×2), and thus (Z)-5-[(dibenzo[b,d]furan-2-yl)methylene]-2-iminothiazolidin-4-one (compound 9) (263 mg, 0.894 mmol, 89.5%, purity: about 85%) was obtained as a light yellow solid.

mp 290-291° C. (dec)

$^1$H NMR (400 MHz, DMSO-d$_6$) δ 9.43 (brs, 1H, NH), 9.17 (brs, 1H, NH), 8.35 (s, 1H, aromatic), 8.17 (d, J=6.8 Hz, 1H, aromatic), 7.85 (d, J=7.2 Hz, 1H, aromatic), 7.77 (s, 1H, olefinic), 7.75-7.71 (m, 2H, aromatic), 7.58 (dd, J=8.0, 1.2 Hz, 1H, aromatic), 7.46 (dd, J=8.0, 0.8 Hz, 1H, aromatic)

Production Example 10: Production of Compound 10

A compound 10 was produced in the following manner.

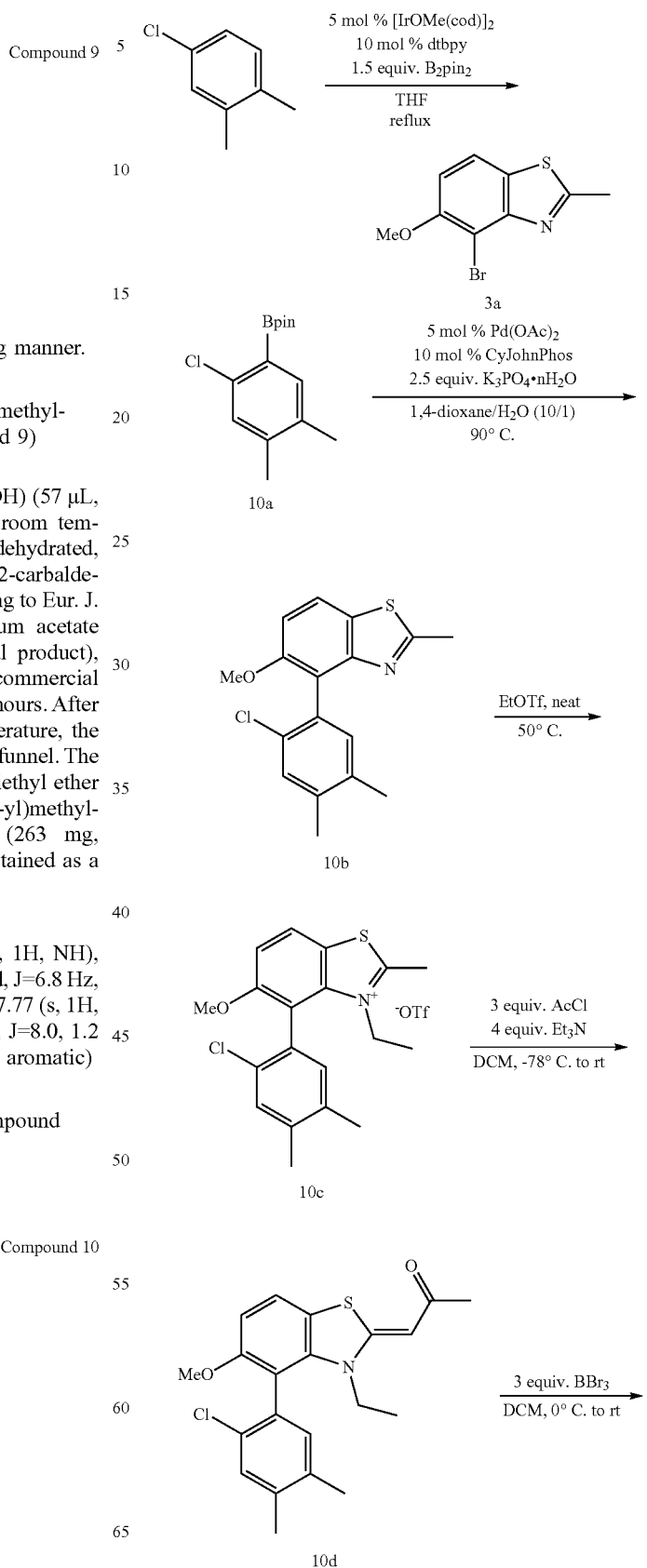

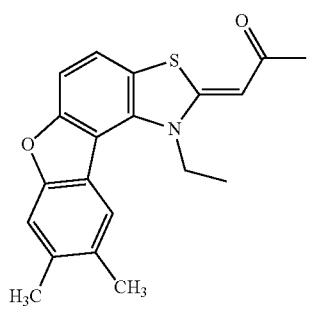

Compound 10

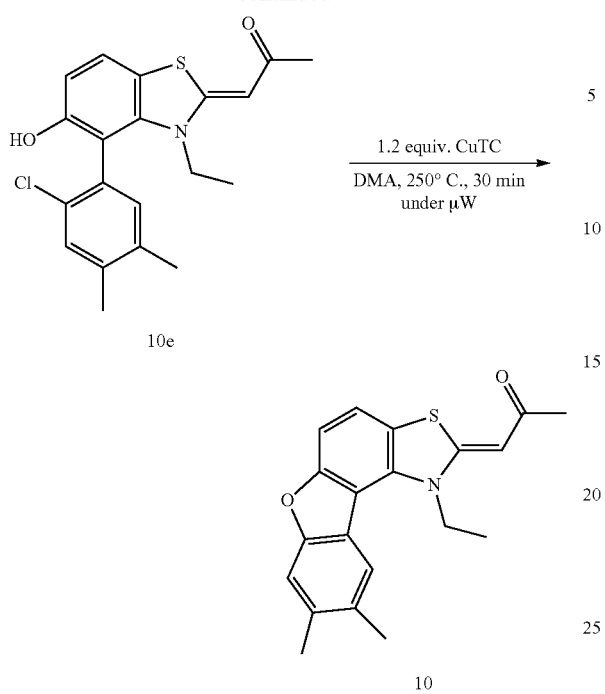

10e

10

Synthesis of 2-(2-chloro-4,5-dimethylphenyl)-4,4,5,5-tetramethyl-1,3,2-dioxaborolane (Compound 10a)

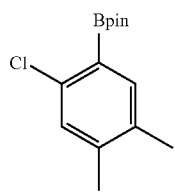

Under the argon atmosphere, 4-chloro-1,2-dimethylbenzene (1.30 mL, 9.68 mmol, commercial product) was added to a tetrahydrofuran (THF) (30 mL, dehydrated, commercial product) solution of (1,5-cyclooctadiene)(methoxy)iridium (I) dimer (331 mg, 0.499 mmol, commercial product), 4,4'-di-tert-butyl bipyridine (268 mg, 0.999 mmol, commercial product), and bis(pinacolato)diboron (3.81 g, 15.0 mmol, commercial product). The mixture was heated to reflux for 4 hours. After the mixture was allowed to cool to room temperature, the mixture was partially purified (n-hexane/AcOEt=20/1) with florisil (75 to 150 μm, commercial product). The resultant solution was concentrated under reduced pressure and purified by a silica gel column chromatography (n-hexane/EtOAc=20/1), and thus 2-(2-chloro-4,5-dimethylphenyl)-4,4,5,5-tetramethyl-1,3,2-dioxaborolane) (compound 10a) (1.99 g, 7.47 mmol, 77.1%) was obtained as a colorless liquid.

TLC $R_f$=0.40 (n-hexane/EtOAc=20/1)

$^1$H NMR (400 MHz, CDCl$_3$) δ 7.45 (s, 1H, aromatic), 7.13 (s, 1H, aromatic), 2.23 (s, 3H, ArCH$_3$), 2.21 (s, 3H, ArCH$_3$), 1.36 (s, 12H, (CH$_3$)$_2$C—C(CH$_3$)$_2$)

Synthesis of 4-(2-chloro-4,5-dimethylphenyl)-5-methoxy-2-methylbenzo[d]thiazole (Compound 10b)

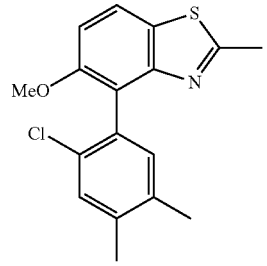 [SMILES: COc1ccc2sc(C)nc2c1-c1cc(C)c(C)cc1Cl]

Under the argon atmosphere, a mixed solution including the compound 3a (141 mg, 0.546 mmol), the compound 10a (159 mg, 0.596 mmol), palladium acetate (Pd(OAc)$_2$) (5.6 mg, 0.025 mmol, commercial product), (2-biphenyl)dicyclohexylphosphine (17.5 mg, 49.9 μmol, commercial product), dioxane (5.0 mL, dehydrated, commercial product) of tri-potassium phosphate n-hydrate (265 mg, 0.992 mmol, commercial product), and purified water (0.5 mL) was stirred by heating at 90° C. for 14.5 hours. After the mixed solution was allowed to cool to room temperature, water (5 mL) was added to the mixed solution. Subsequently, the mixture was extracted with ethyl acetate (5 mL×4). The combined organic layer was dried over sodium sulfate. The mixture was concentrated under reduced pressure and purified by a medium-pressure column chromatography (Smart Flash EPCLC W-Prep 2XY system) (n-hexane/AcOEt=5/1), and thus 4-(2-chloro-4,5-dimethylphenyl)-5-methoxy-2-methylbenzo[d]thiazole (compound 10b) (106 mg, 0.334 mmol, 61.1%) was obtained as a colorless solid.

TLC $R_f$=0.40 (n-hexane/EtOAc=5/1)

$^1$H NMR (400 MHz, CDCl$_3$) δ 7.77 (d, J=8.8 Hz, 1H, aromatic), 7.31 (s, 1H, aromatic), 7.16 (s, 1H, aromatic), 7.11 (d, J=8.8, 1H, aromatic), 3.84 (s, 3H, OCH$_3$), 2.75 (s, 3H, hetArCH$_3$), 2.30 (s, 3H, ArCH$_3$), 2.28 (s, 3H, ArCH$_3$)

Synthesis of 4-(2-chloro-4,5-dimethylphenyl)-3-ethyl-5-methoxy-2-methylbenzo[d]thiazol-3-ium Triflate (Compound 10c)

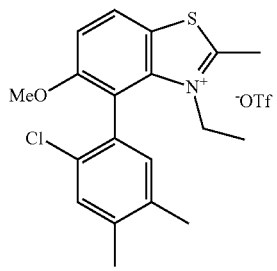 [SMILES: CC[n+]1c(C)sc2ccc(OC)c(-c3cc(C)c(C)cc3Cl)c21 ; "-OTf"]

Under the argon atmosphere, an ethyl triflate (EtOTf) (0.5 mL, commercial product) suspension of the compound 10b (106 mg, 0.334 mmol) was stirred by heating at 50° C. (i.e., the oil bath temperature) for 2.5 hours. After the suspension was allowed to cool to room temperature, the precipitated crystal was filtered off with a Hirsch funnel. The crystal was washed with n-hexane (3 mL×4), and thus 4-(2-chloro-4,5- dimethylphenyl)-3-ethyl-5-methoxy-2-methylbenzo[d]thi-azol-3-ium triflate (compound 10c) (156 mg, 0.315 mmol, 94.2%) was obtained as a colorless solid. $^1$H NMR (400 MHz, CDCl$_3$) δ 8.06 (d, J=8.8 Hz, 1H, aromatic), 7.42 (d, J=8.8 Hz, 1H, aromatic), 7.32 (s, 1H, aromatic), 7.27 (s, 1H, aromatic), 4.28 (q, J=7.2 Hz, 2H, CH$_2$CH$_3$), 3.86 (s, 3H, OCH$_3$), 3.19 (s, 3H, hetArCH$_3$), 2.35 (s, 3H, ArCH$_3$), 2.30 (s, 3H, ArCH$_3$), 1.14 (t, J=7.2 Hz, 3H, CH$_2$CH$_3$)

Synthesis of (Z)-1-(2-chloro-4,5-dimethylphenyl)-3-ethyl-5-methoxybenzo[d]thiazole-2(3H)-ylidene) propan-2-one (Compound 10d)

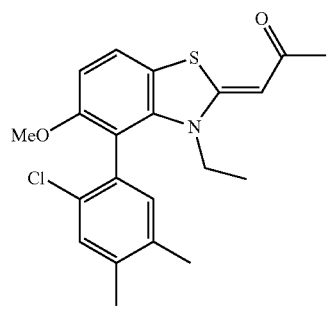 [SMILES: CCN1/C(=C/C(C)=O)Sc2ccc(OC)c(-c3cc(C)c(C)cc3Cl)c21]

Under the argon atmosphere, triethylamine (167 μL, 1.20 mmol, commercial product) and acetyl chloride (64 μL, 0.90 μmol, commercial product) were added at −78° C. to a dichloromethane (3.0 mL, dehydrated, commercial product) solution of the compound 10c (149 mg, 0.300 mmol). The temperature was raised to room temperature, and then the mixture was stirred for 1 hour. After the reaction was completed, water (about 3 mL) was added to the mixture. Subsequently, the mixture was extracted with dichloromethane (3 mL×4). The combined organic layer was dried over sodium sulfate and filtered. The filtrate was concentrated under reduced pressure and purified by a medium-pressure column chromatography (Smart Flash EPCLC W-Prep 2XY system) (n-hexane/EtOAc=1/1), and thus (Z)-1-(2-chloro-4,5-dimethylphenyl)-3-ethyl-5-methoxybenzo[d]thiazole-2(3H)-ylidene) propan-2-one (compound 10d) (74.8 mg, 0.193 mmol, 64.3%) was obtained as a yellow solid.

TLC R$_f$=0.35 (n-hexane/EtOAc=1/1)

$^1$H NMR (400 MHz, CDCl$_3$) δ 7.51 (d, J=8.8 Hz, 1H, aromatic), 7.28 (s, 1H, aromatic), 7.06 (s, 1H, aromatic), 6.82 (d, J=8.8 Hz, 1H, aromatic), 5.77 (s, 1H, olefinic), 3.72 (s, 3H, OCH$_3$), 3.62-3.49 (m, 2H, CH$_2$CH$_3$), 2.32 (s, 3H, ArCH$_3$), 2.26 (s, 3H, ArCH$_3$), 2.21 (s, 3H, C(O)CH$_3$), 0.95 (t, J=7.2 Hz, 3H, CH$_2$CH$_3$)

Synthesis of (Z)-1-(2-chloro-4,5-dimethylphenyl)-3-ethyl-5-hydroxybenzo[d]thiazol-2(3H)-ylidene) propan-2-one (Compound 10e)

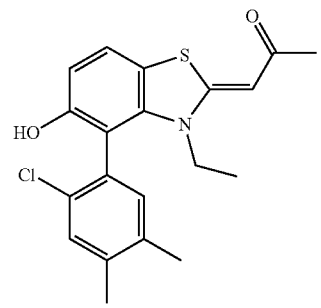 [SMILES: CCN1/C(=C/C(C)=O)Sc2ccc(O)c(-c3cc(C)c(C)cc3Cl)c21]

Under the argon atmosphere, boron tribromide (1.0 M dichloromethane solution, 0.58 mL, 0.58 mmol, commercial product) was added at 0° C. to a dichloromethane solution (2.0 mL, dehydrated, commercial product) of the compound 10d (74.8 mg, 0.193 mmol). The temperature was raised to room temperature, and then the mixture was stirred for 5 hours. After the reaction was completed, water (about 2 mL) was added at 0° C. to the mixture. Subsequently, the mixture was extracted with dichloromethane (2 mL×4) and a small amount of methanol (about 0.3 mL). The combined organic layer was dried over sodium sulfate and filtered. The filtrate was concentrated under reduced pressure. The resultant solid was filtered off with a Hirsch funnel. The solid was washed with cold methanol (3 mL×4), and thus (Z)-1-(2-chloro-4,5-dimethylphenyl)-3-ethyl-5-hydroxybenzo[d]thi-azol-2(3H)-ylidene) propan-2-one (compound 10e) (56.2 mg, 0.150 mmol, 77.9%) was obtained as an orange solid.

TLC R$_f$=0.20 (CH$_2$Cl$_2$/MeOH=20/1)

$^1$H NMR (400 MHz, DMSO-d$_6$) δ 9.53 (s, 1H, ArOH), 7.50 (d, J=8.4, 1H, aromatic), 7.35 (s, 1H, aromatic), 7.20 (s, 1H, aromatic), 6.78 (d, J=8.4 Hz, 1H, aromatic), 5.91 (s, 1H, olefinic), 3.66-3.56 (m, 1H, CH$_{AA'-Gem}$CH$_3$), 3.51-3.41 (m, 1H, CH$_{AA'-Gem}$CH$_3$), 2.29 (s, 3H, ArCH$_3$), 2.23 (s, 3H, ArCH$_3$), 2.06 (s, 3H, C(O)CH$_3$), 0.84 (t, J=6.8 Hz, 3H, CH$_2$CH$_3$)

Synthesis of (Z)-1-(8,9-dimethyl-1-ethylbenzo[2,3] benzofuro[4,5-d]thiazol-2(1H)-ylidene)propan-2-one (Compound 10)

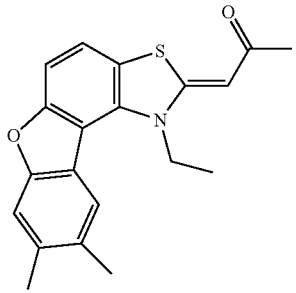 [SMILES: CCN1/C(=C/C(C)=O)Sc2ccc3oc4cc(C)c(C)cc4c3c21]

Under the argon atmosphere, an N,N-dimethylacetamide (1.4 mL, dehydrated, commercial product) solution of the compound 10e (52.5 mg, 0.140 mmol) and copper (I) thiophene-2-carboxylate (32.0 mg, 0.168 mmol, commercial product) was stirred by heating at 250° C. for 30 minutes under microwave irradiation. After the solution was allowed to cool to room temperature, hydrochloric acid (1 M, 0.2 mL) was added to the solution. Subsequently, the mixture was extracted with dichloromethane (2 mL×4). The combined organic layer was dried over sodium sulfate and filtered. The filtrate was concentrated under reduced pressure and purified by a medium-pressure column chromatography (Smart Flash EPCLC W-Prep 2XY system) (n-hexane/EtOAc=1/1), and thus (Z)-1-(8, 9-dimethyl-1-ethylbenzo[2,3]benzofuro[4,5-d]thiazol-2(1H)-ylidene)propan-2-one (compound 10) (25.8 mg, 76.5 µmol, 54.6%) was obtained as a brown solid.

TLC $R_f$=0.40 (n-hexane/EtOAc=1/1)

mp 263-265° C.

IR (KBr cm$^{-1}$) 3074, 2977, 2941, 1607, 1506, 1489, 1330, 1316, 1115, 975, 863, 802, 777

$^1$H NMR (500 MHz, CDCl$_3$) δ 7.72 (s, 1H, aromatic), 7.54 (d, J=8.5 Hz, 1H, aromatic), 7.38 (s, 1H, aromatic), 7.35 (d, J=8.5 Hz, 1H, aromatic), 6.00 (s, 1H, olefinic), 4.60 (q, 2H, J=6.5 Hz, CH$_2$CH$_3$), 2.41 (s, 6H, ArCH$_3$×2), 2.29 (s, 3H, C(O)CH$_3$), 1.70 (t, J=6.5 Hz, 3H, CH$_2$CH$_3$)

$^{13}$C NMR (126 MHz, CDCl$_3$) δ 190.9, 160.7, 156.6, 154.9, 136.7, 134.9, 131.5, 122.9, 121.0, 120.2, 118.8, 112.6, 109.3, 106.9, 90.0, 43.5, 29.0, 20.6, 20.4, 14.3

Production Example 11: Production of Compound 11

Compound 11

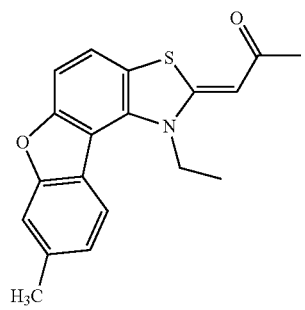

A compound 11 was produced in the following manner.

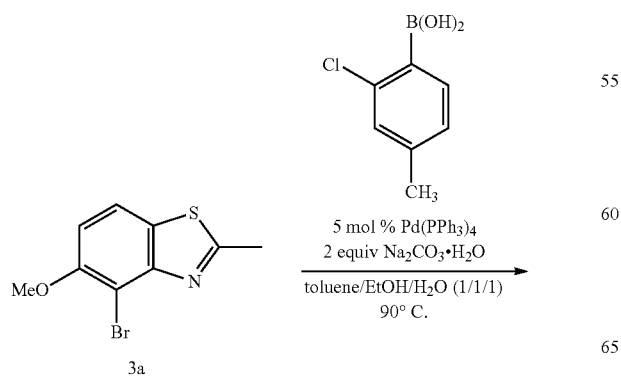

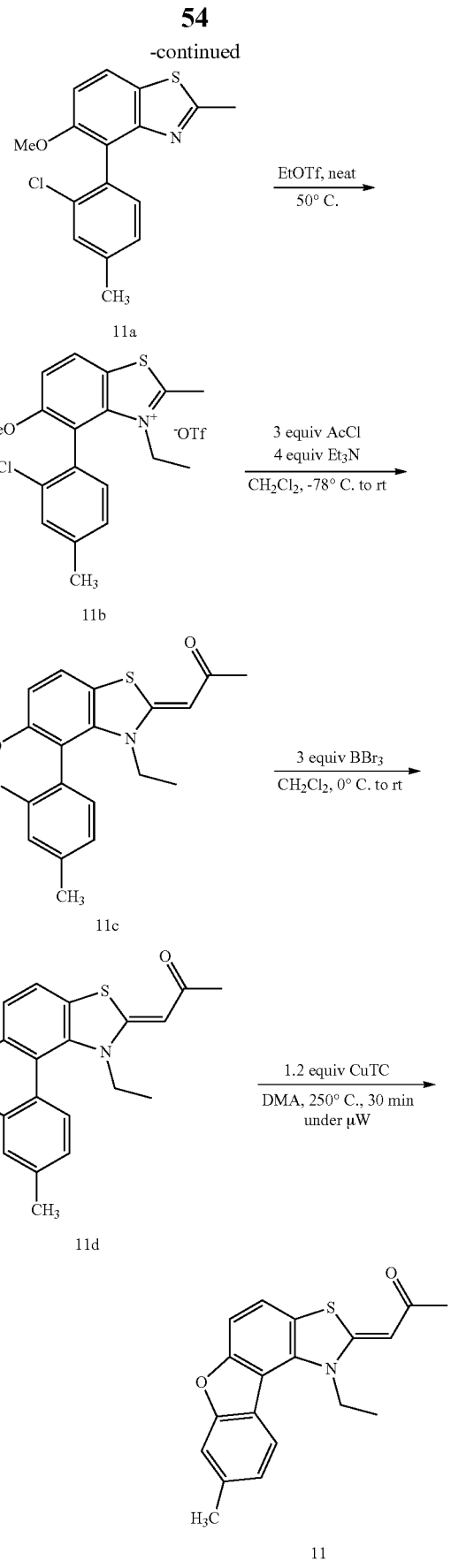

Synthesis of 4-(2-chloro-4-methylphenyl)-5-methoxy-2-methylbenzo[d]thiazole (Compound 11a)

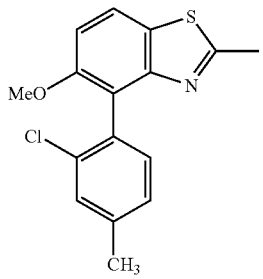 [SMILES: COc1ccc2sc(C)nc2c1-c1ccc(C)cc1Cl]

Under the argon atmosphere, a mixed solution including the compound 3a (285 mg, 1.10 mmol), (2-chloro-4-methylphenyl)boronic acid (226 mg, 1.33 mmol, commercial product), tetrakis(triphenylphosphine)palladium (63.6 mg, 55.0 μmol, commercial product), toluene (4 mL, dehydrated, commercial product) of sodium carbonate monohydrate (233 mg, 1.88 mmol, commercial product), ethanol (EtOH) (4 mL, dehydrated, commercial product), and purified water (4 mL) was stirred by heating at 90° C. for 2.5 hours. After the mixed solution was allowed to cool to room temperature, the mixture was concentrated under reduced pressure and purified by a medium-pressure column chromatography (Smart Flash EPCLC W-Prep 2XY system) (n-hexane/AcOEt=5/1), and thus 4-(2-chloro-4-methylphenyl)-5-methoxy-2-methylbenzo[d]thiazole (compound 11a) (188 mg, 0.619 mmol, 56.3%) was obtained as a colorless solid.

TLC $R_f$=0.40 (n-hexane/EtOAc=5/1)

$^1$H NMR (400 MHz, CDCl$_3$) δ 7.77 (d, J=8.8 Hz, 1H, aromatic), 7.35 (d, J=0.8 Hz, 1H, aromatic), 7.27 (d, J=7.6 Hz, 1H, aromatic), 7.17 (d, J=7.6, 0.8 Hz, 1H, aromatic), 7.10, (d, J=8.8 Hz, 1H, aromatic), 3.83 (s, 3H, OCH$_3$), 2.74 (s, 3H, hetArCH$_3$), 2.40 (s, 3H, ArCH$_3$)

Synthesis of 4-(2-chloro-4-methylphenyl)-3-ethyl-5-methoxy-2-methylbenzo[d]thiazol-3-ium triflate (Compound 11b)

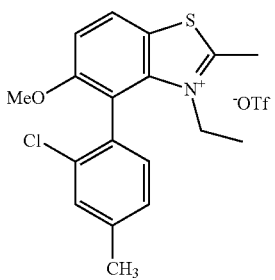 [SMILES: CC[n+]1c(C)sc2ccc(OC)c(-c3ccc(C)cc3Cl)c21 ; "-OTf"]

Under the argon atmosphere, an ethyl triflate (EtOTf) (about 1 mL, commercial product) suspension of the compound 11a (606 mg, 1.99 mmol) was stirred by heating at 50° C. (i.e., the oil bath temperature) for 13.5 hours. After the suspension was allowed to cool to room temperature, the precipitated crystal was filtered off with a Hirsch funnel. The crystal was washed with n-hexane (3 mL×4), and thus 4-(2-chloro-4-methylphenyl)-3-ethyl-5-methoxy-2-methylbenzo[d]thiazol-3-ium triflate (compound 11b) (899 mg, 1.87 mmol, 93.7%) was obtained as a light yellow solid.

$^1$H NMR (400 MHz, CDCl$_3$) δ 8.09 (d, J=9.2 Hz, 1H, aromatic), 7.44-7.41 (m, 3H, aromatic), 7.28 (d, J=9.2 Hz, 1H, aromatic), 4.28 (q, 2H, J=7.2 Hz, CH$_2$CH$_3$), 3.85 (s, 3H, OCH$_3$), 3.18 (s, 3H, hetArCH$_3$), 2.46 (s, 3H, ArCH$_3$), 1.13 (t, J=7.2 Hz, 3H, CH$_2$CH$_3$)

Synthesis of (Z)-1-(4-(2-chloro-4-methylphenyl)-3-ethyl-5-methoxybenzo[d]thiazole-2(3H)-ylidene)propan-2-one (Compound 11c)

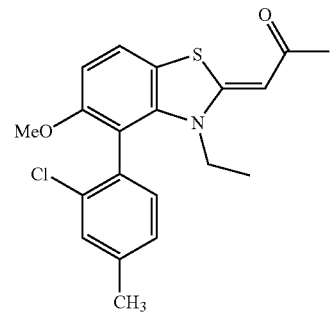 [SMILES: CCN1/C(=C/C(C)=O)Sc2ccc(OC)c(-c3ccc(C)cc3Cl)c21]

Under the argon atmosphere, triethylamine (170 μL, 1.22 mmol, commercial product) and acetyl chloride (64 μL, 0.90 μmol, commercial product) were added at −78° C. to a dichloromethane (3.0 mL, dehydrated, commercial product) solution of the compound 11b (145 mg, 0.301 mmol). The temperature was raised to room temperature, and then the mixture was stirred for 1.5 hours. After the reaction was completed, water (about 5 mL) was added to the mixture. Subsequently, the mixture was extracted with dichloromethane (3 mL×4). The combined organic layer was dried over sodium sulfate and filtered. The filtrate was concentrated under reduced pressure and purified by a medium-pressure column chromatography (Smart Flash EPCLC W-Prep 2XY system) (n-hexane/EtOAc=1/1), and thus (Z)-1-(4-(2-chloro-4-methylphenyl)-3-ethyl-5-methoxybenzo[d]thiazole-2(3H)-ylidene)propan-2-one (compound 11c) (54.3 mg, 0.145 mmol, 48.2%) was obtained as a yellow solid.

TLC $R_f$=0.30 (n-hexane/EtOAc=1/1)

$^1$H NMR (400 MHz, CDCl$_3$) δ 7.52 (d, J=8.4 Hz, 1H, aromatic), 7.34 (s, 1H, aromatic), 7.21-7.14 (m, 2H, aromatic), 6.83 (d, J=8.4 Hz, 1H, aromatic), 5.78 (s, 1H, olefinic), 3.72 (s, 3H, OCH$_3$), 3.65-3.48 (m, 2H, CH$_2$CH$_3$), 2.43 (s, 3H, C(O)CH$_3$), 2.21 (s, 3H, ArCH$_3$), 0.95 (t, J=7.2 Hz, 3H, CH$_2$CH$_3$)

Synthesis of (Z)-1-[4-(2-chloro-4-methylphenyl)-3-ethyl-5-hydroxybenzo[d]thiazol-2(3H)-ylidene]propan-2-one (Compound 11d)

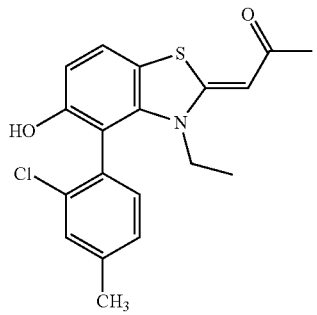 [SMILES: CCN1/C(=C/C(C)=O)Sc2ccc(O)c(-c3ccc(C)cc3Cl)c21]

Under the argon atmosphere, boron tribromide (1.0 M dichloromethane solution, 0.30 mL, 0.30 mmol, commercial product) was added at 0° C. to a dichloromethane (1.0 mL, dehydrated, commercial product) solution of the compound 11c (37.4 mg, 0.100 mmol). The temperature was raised to room temperature, and then the mixture was stirred for 1.5 hours. After the reaction was completed, water (about 5 mL) was added at 0° C. to the mixture. Subsequently, the mixture was extracted with dichloromethane (3 mL×4) and a small amount of methanol (about 0.5 mL). The combined organic layer was dried over sodium sulfate and filtered. The filtrate was concentrated under reduced pressure, and thus (Z)-1-[4-(2-chloro-4-methylphenyl)-3-ethyl-5-hydroxybenzo[d]thiazol-2(3H)-ylidene]propan-2-one (compound 11d) was obtained as a yellow solid. This compound was used for the next reaction without purification.

$^1$H NMR (400 MHz, DMSO-d$_6$) δ 9.55 (s, 1H, ArOH), 7.52 (d, J=8.4 Hz, 1H, aromatic), 7.42 (s, 1H, aromatic), 7.32 (d, J=8.4 Hz, 1H, aromatic), 7.23 (d, J=8.4 Hz, 1H, aromatic), 6.79 (d, J=8.4 Hz, 1H, aromatic), 5.92 (s, 1H, olefinic), 3.67-3.57 (m, 1H, CH$_{AA'-Gem}$CH$_3$), 3.53-3.41 (m, 1H, CH$_{AA'-Gem}$CH$_3$), 2.38 (s, 3H, ArCH$_3$), 2.06 (s, 3H, C(O)CH$_3$), 0.83 (t, J=7.2 Hz, 3H, CH$_2$CH$_3$)

Synthesis of (Z)-1-(1-ethyl-8-methylbenzo[2,3]benzofuro[4,5-d]thiazol-2(1H)-ylidene)propan-2-one (Compound 11)

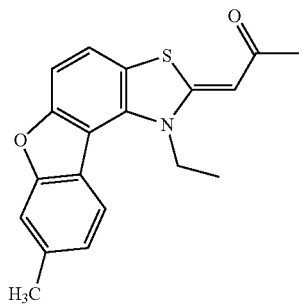 [SMILES: CCN1/C(=C/C(C)=O)Sc2ccc3oc4cc(C)ccc4c3c21]

Under the argon atmosphere, an N,N-dimethylacetamide (1.0 mL, dehydrated, commercial product) solution of the compound 11d (<0.100 mmol) and copper (I) thiophene-2-carboxylate (22.9 mg, 0.120 mmol, commercial product) was stirred by heating at 250° C. for 30 minutes under microwave irradiation. After the solution was allowed to cool to room temperature, hydrochloric acid (1 M, 0.2 mL) was added to the solution. Subsequently, the mixture was extracted with dichloromethane (3 mL×4). The combined organic layer was dried over sodium sulfate and filtered. The filtrate was concentrated under reduced pressure and purified by a silica gel column chromatography (n-hexane/EtOAc=1/1), and thus (Z)-1-(1-ethyl-8-methylbenzo[2,3]benzofuro[4,5-d]thiazol-2(1H)-ylidene)propan-2-one (compound 11) (13.2 mg, 40.8 μmol, 40.8% in 2 steps) was obtained as a light brown solid.

TLC R$_f$=0.25 (n-hexane/EtOAc=1/1)

mp 204-205° C.

IR (KBr, cm$^{-1}$) 3062, 2970, 2360, 1606, 1470, 1187, 1014, 805, 723

$^1$H NMR (500 MHz, CDCl$_3$) δ 7.90 (d, J=8.5 Hz, 1H, aromatic), 7.60 (d, J=8.0 Hz, 1H, aromatic), 7.45 (s, 1H, aromatic), 7.41 (d, J=8.0 Hz, 1H, aromatic), 7.21, (d, J=8.5 Hz, 1H, aromatic), 6.04 (s, 1H, olefinic), 4.66 (q, J=7.0 Hz, 2H, CH$_2$CH$_3$), 2.55 (s, 3H, ArCH$_3$), 2.30 (s, 3H, C(O)CH$_3$), 1.72 (t, J=7.0 Hz, 3H, CH$_2$CH$_3$)

$^{13}$C NMR (126 MHz, CDCl$_3$) δ 191.1, 160.7, 156.6, 156.5, 137.9, 134.9, 124.6, 122.1, 121.2, 120.5, 118.6, 112.5, 109.3, 107.0, 90.1, 43.6, 29.1, 21.6, 14.3

Production Example 12: Production of Compound 12

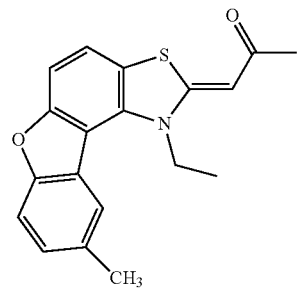

Compound 12

A compound 12 was produced in the following manner.

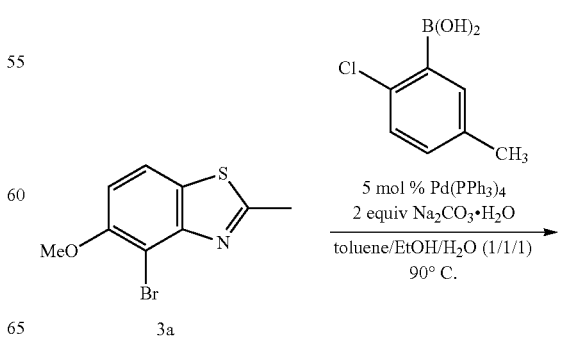

Synthesis of 4-(2-chloro-5-methylphenyl)-5-methoxy-2-methylbenzo[d]thiazole (Compound 12a)

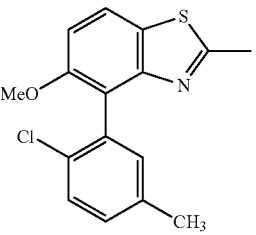 [SMILES: COc1ccc2sc(C)nc2c1-c1cc(C)ccc1Cl]

Under the argon atmosphere, a mixed solution including the compound 3a (521 mg, 2.02 mmol), (2-chloro-5-methylphenyl)boronic acid (409 mg, 2.40 mmol, commercial product), tetrakis(triphenylphosphine)palladium (116 mg, 0.100 mmol, commercial product), toluene (7 mL, dehydrated, commercial product) of sodium carbonate monohydrate (424 mg, 3.42 mmol, commercial product), ethanol (EtOH) (7 mL, dehydrated, commercial product), and purified water (7 mL) was heated to reflux at 90° C. for 7 hours. After the mixed solution was allowed to cool to room temperature, the mixture was concentrated under reduced pressure and purified by a medium-pressure column chromatography (Smart Flash EPCLC W-Prep 2XY system) (n-hexane/EtOAc=5/1), and thus 4-(2-chloro-5-methylphenyl)-5-methoxy-2-methylbenzo[d]thiazole (compound 12a) (399 mg, 1.31 mmol, 65.0%) was obtained as a colorless solid.

TLC $R_f$=0.40 (n-hexane/EtOAc=5/1)

$^1$H NMR (400 MHz, CDCl$_3$) δ 7.77 (d, J=8.8 Hz, 1H, aromatic), 7.39 (d, J=8.0 Hz, 1H, aromatic), 7.18-7.12 (m, 2H, aromatic), 7.10 (d, J=8.8 Hz, 1H, aromatic), 3.83 (s, 3H, OCH$_3$), 2.74 (s, 3H, hetArCH$_3$), 2.37 (s, 3H, ArCH$_3$)

Synthesis of 4-(2-chloro-5-methylphenyl)-3-ethyl-5-methoxy-2-methylbenzo[d]thiazol-3-ium Triflate (Compound 12b)

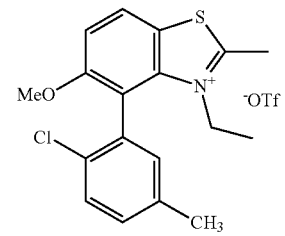 [SMILES: CC[n+]1c(C)sc2ccc(OC)c(-c3cc(C)ccc3Cl)c21 ; "-OTf"]

Under the argon atmosphere, the compound 12a (399 mg, 1.31 mmol) was dissolved in ethyl triflate (EtOTf) (1 mL, commercial product), and the mixed solution was stirred by heating at 50° C. (i.e., the oil bath temperature) for 14 hours. After the mixed solution was allowed to cool to room temperature, the precipitated crystal was filtered off with a Hirsch funnel. The crystal was washed with n-hexane (about 3 mL×4), and thus 4-(2-chloro-5-methylphenyl)-3-ethyl-5-methoxy-2-methylbenzo[d]thiazol-3-ium triflate (compound 12b) (584 mg, 1.21 mmol, 92.5%) was obtained as a colorless solid.

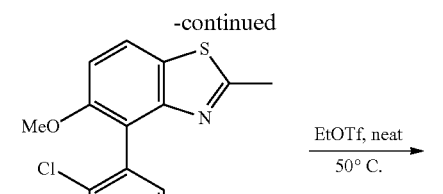

12a

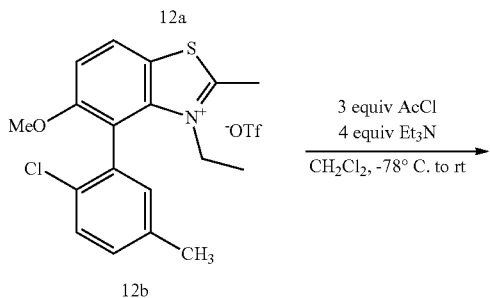

12b

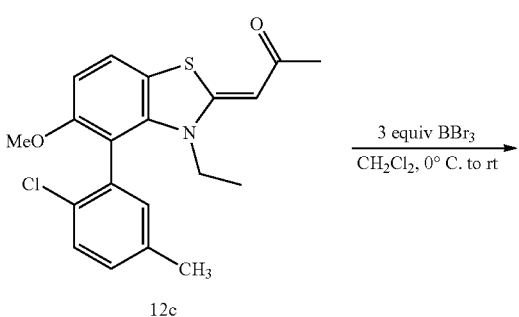

12c

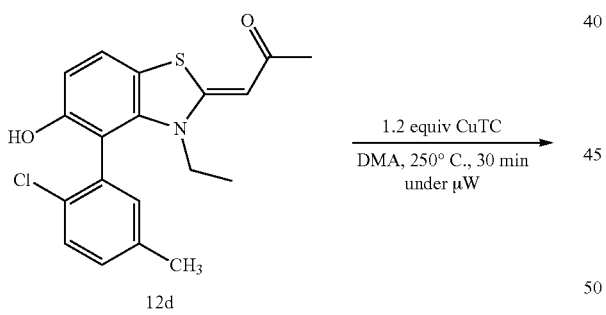

12d

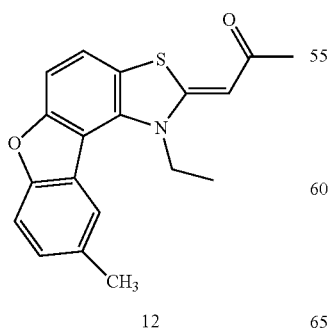

12

$^1$H NMR (400 MHz, CDCl$_3$) δ 8.08 (d, J=9.2 Hz, 1H, aromatic), 7.45-7.41 (m, 2H, aromatic), 7.34-7.26 (m, 2H, aromatic), 4.31-4.21 (m, 2H, NCH$_2$CH$_3$), 3.86 (s, 3H, OCH$_3$), 3.18 (s, 3H, hetArCH$_3$), 2.41 (s, 3H, ArCH$_3$), 1.13 (t, J=7.2 Hz, 3H, NCH$_2$CH$_3$)

Synthesis of (Z)-1-(4-(2-chloro-5-methylphenyl)-3-ethyl-5-methoxybenzo[d]thiazole-2(3H)-ylidene)propan-2-one (Compound 12c)

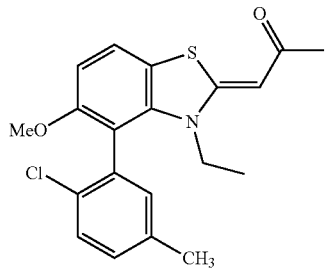 [SMILES: CCN1/C(=C/C(C)=O)Sc2ccc(OC)c(-c3cc(C)ccc3Cl)c21]

Under the argon atmosphere, triethylamine (670 μL, 4.81 mmol, commercial product) and acetyl chloride (260 μL, 3.66 μmol, commercial product) were added at −78° C. to a dichloromethane (12 mL, dehydrated, commercial product) solution of the compound 12b (584 mg, 1.21 mmol). The temperature was raised to room temperature, and then the mixture was stirred for 30 minutes. After the reaction was completed, water (about 15 mL) was added to the mixture. Subsequently, the mixture was extracted with dichloromethane (about 10 mL×4). The combined organic layer was dried over sodium sulfate and filtered. The filtrate was concentrated under reduced pressure and purified by a medium-pressure column chromatography (Smart Flash EPCLC W-Prep 2XY system) (n-hexane/EtOAc=1/1), and thus (Z)-1-(4-(2-chloro-5-methylphenyl)-3-ethyl-5-methoxybenzo[d]thiazole-2(3H)-ylidene)propan-2-one (compound 12c) (335 mg, 0.896 mmol, 74.0%) was obtained as a yellow solid.

$^1$H NMR, (400 MHz, CDCl$_3$) δ 7.53 (d, J=8.4 Hz, 1H, aromatic), 7.38 (d, J=8.0 Hz, 1H, aromatic), 7.19 (dd, J=8.0, 2.0 Hz, 1H, aromatic), 7.12 (d, J=0.8 Hz, 1H, aromatic), 6.83 (d, J=8.4 Hz, 1H, aromatic), 5.78 (s, 1H, olefinic), 3.73 (s, 3H, OCH$_3$), 3.60-3.47 (m, 2H, NCH$_2$CH$_3$), 2.37 (s, 3H, ArCH$_3$), 2.22 (s, 3H, C(O)CH$_3$), 0.95 (t, J=7.2 Hz, 3H, NCH$_2$CH$_3$)

Synthesis of (Z)-1-(4-(2-chloro-5-methylphenyl)-3-ethyl-5-hydroxybenzo[d]thiazole-2(3H)-ylidene)propan-2-one (Compound 12d)

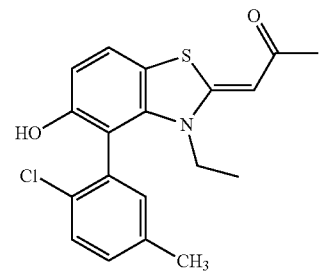 [SMILES: CCN1/C(=C/C(C)=O)Sc2ccc(O)c(-c3cc(C)ccc3Cl)c21]

Under the argon atmosphere, boron tribromide (2.2 mL, 2.2 mmol, commercial product) was added at 0° C. to a dichloromethane (7.5 mL, dehydrated, commercial product) solution of the compound 12c (277 mg, 0.741 mmol). The temperature was raised to room temperature, and then the mixture was stirred for 4.5 hours. After the reaction was completed, water (about 10 mL) was added at 0° C. to the mixture. Subsequently, the mixture was extracted with dichloromethane (about 5 mL×4) and a small amount of methanol (about 0.5 mL). The combined organic layer was dried over sodium sulfate and filtered. The filtrate was concentrated under reduced pressure and purified by a silica gel column chromatography (n-hexane/EtOAc=1/1), and thus (Z)-1-(4-(2-chloro-5-methylphenyl)-3-ethyl-5-hydroxybenzo[d]thiazole-2(3H)-ylidene)propan-2-one (compound 12d) (220 mg, 0.611 mmol, 82.5%) was obtained as an yellowish brown solid.

TLC R$_f$=0.30 (CH$_2$Cl$_2$/MeOH=20/1)

$^1$H NMR (400 MHz, DMSO-d$_6$) δ 9.57 (s, 1H, ArOH), 7.52 (d, J=8.4 Hz, 1H, aromatic), 7.45 (d, J=8.8 Hz, 1H, aromatic), 7.28-7.26 (m, 2H, aromatic), 6.80 (d, J=8.4 Hz, 1H, aromatic), 5.92 (s, 1H, olefinic), 3.63-3.56 (m, 1H, NCH$_{gem-AA}$CH$_3$), 3.47-3.39 (m, 1H, NCH$_{gem-AA}$CH$_3$), 2.32 (s, 3H, ArCH$_3$), 2.06 (s, 3H, C(O)CH$_3$), 0.83 (t, J=6.8 Hz, 3H, NCH$_2$CH$_3$)

Synthesis of (Z)-1-(1-ethyl-9-methylbenzo[2,3]benzofuro[4,5-d]thiazol-2(1H)-ylidene)propan-2-one (Compound 12)

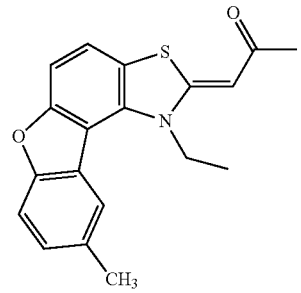 [SMILES: CCN1/C(=C/C(C)=O)Sc2ccc3oc4ccc(C)cc4c3c21]

Under the argon atmosphere, an N,N-dimethylacetamide (20 mL, dehydrated, commercial product) solution of the compound 12d (144 mg, 0.400 mmol) and copper (I) thiophene-2-carboxylate (91.5 mg, 0.480 mmol, commercial product) was stirred by heating at 250° C. for 30 minutes under microwave irradiation. After the solution was allowed to cool to room temperature, diluted hydrochloric acid (0.1 M, 0.4 mL) was added to the solution. Subsequently, the mixture was extracted with dichloromethane (about 10 mL×4). The combined organic layer was dried over sodium sulfate and filtered. The filtrate was concentrated under reduced pressure and purified by a silica gel column chromatography (n-hexane/EtOAc=1/1), and thus (Z)-1-(1-ethyl-9-methylbenzo[2,3]benzofuro[4,5-d]thiazol-2(1H)-ylidene)propan-2-one (compound 12) (96.4 mg, 0.298 mmol, 74.5%) was obtained as a brown solid.

TLC R$_f$=0.30 (n-hexane/EtOAc=1/1)

mp 191-192° C.

IR (KBr, cm$^{-1}$) 3357, 2973, 2921, 2360, 1610, 1360, 1193, 1013, 803

$^1$H NMR (500 MHz, CDCl$_3$) δ 7.84 (s, 1H, aromatic), 7.63 (d, J=8.5 Hz, 1H, aromatic), 7.54 (d, J=8.5 Hz, 1H, aromatic), 7.43 (d, J=8.5 Hz, 1H, aromatic), 7.34, (d, J=8.5 Hz, 1H, aromatic), 6.05 (s, 1H, olefinic), 4.68 (q, 2H, J=7.0 Hz, CH₂CH₃), 2.56 (s, 3H, ArCH₃), 2.31 (s, 3H, C(O)CH₃), 1.75 (t, J=7.0 Hz, 3H, CH₂CH₃)
¹³C NMR (126 MHz, CDCl₃) δ 191.1, 160.8, 156.9, 154.4, 135.2, 132.5, 128.2, 122.7, 121.2, 121.1, 120.9, 111.8, 109.3, 107.0, 90.2, 43.7, 29.1, 22.0, 14.4
Production Example 13: Production of Compound 13
Compound 13
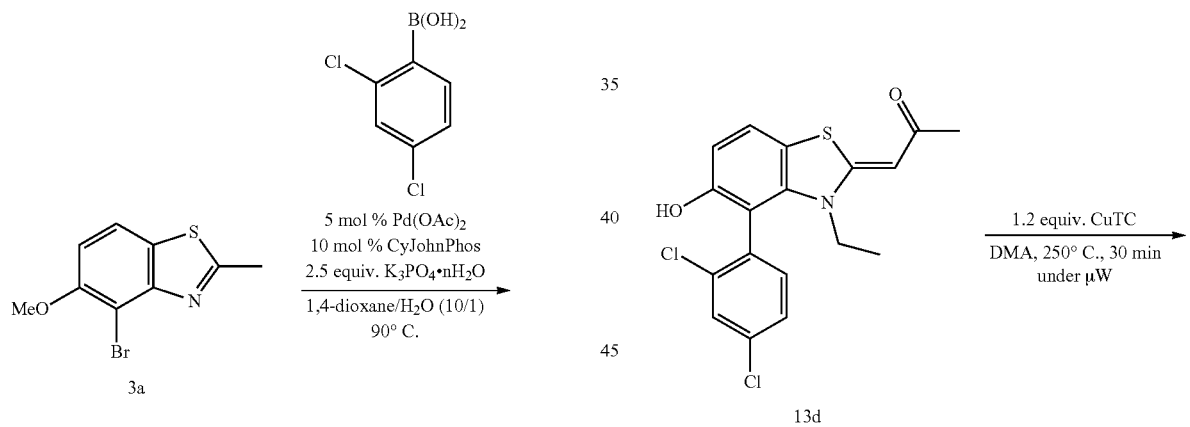
A compound 13 was produced in the following manner.
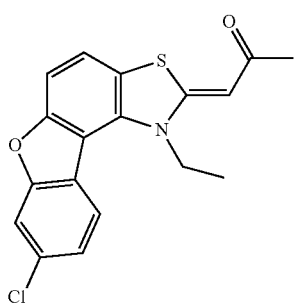
3a
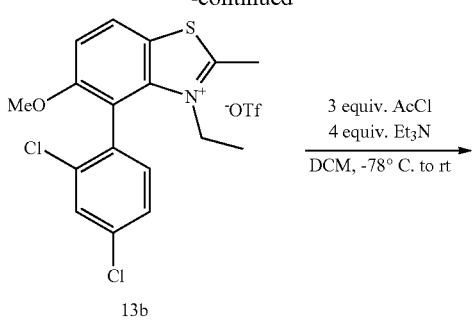
13b
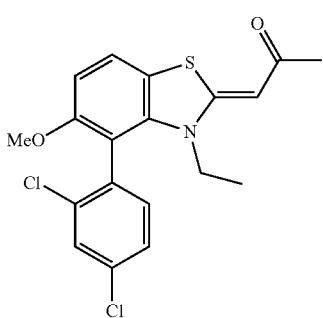
13c
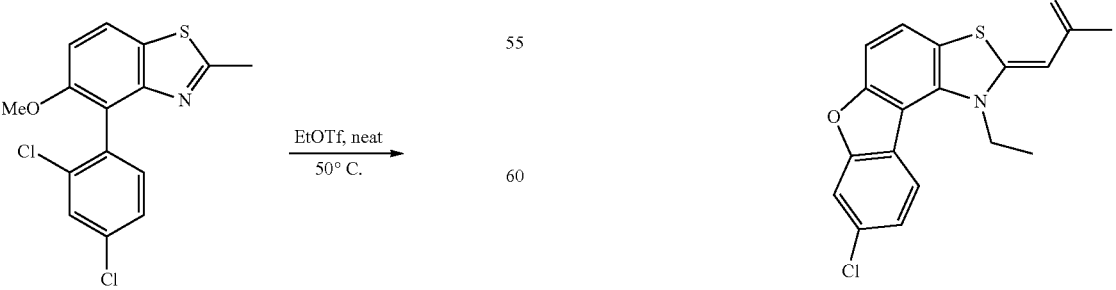
13d
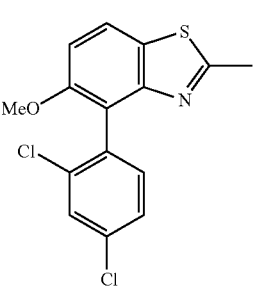
13a
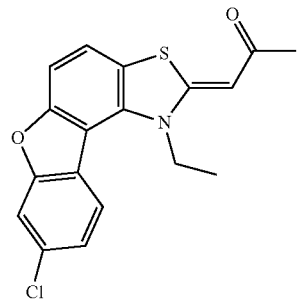
13

Synthesis of 4-(2,4-dichlorophenyl)-5-methoxy-2-methylbenzo[d]thiazole (Compound 13a)

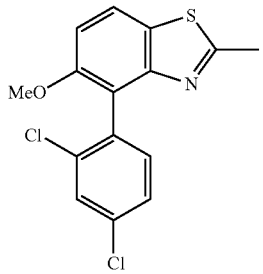 [SMILES: COc1ccc2sc(C)nc2c1-c1ccc(Cl)cc1Cl]

Under the argon atmosphere, a mixed solution including the compound 3a (3.26 g, 12.6 mmol), (2,4-dichlorophenyl)boronic acid (3.40 g, 17.8 mmol, commercial product), palladium acetate (Pd(OAc)$_2$) (135 mg, 0.601 mmol, commercial product), (2-biphenyl)dicyclohexylphosphine (421 mg, 1.20 mmol, commercial product), dioxane (120 mL, dehydrated, commercial product) of tri-potassium phosphate n-hydrate (5.10 g, 19.1 mmol, commercial product), and purified water (12 mL) was stirred by heating at 90° C. for 16 hours. After the mixed solution was allowed to cool to room temperature, water (50 mL) and saturated saline (50 mL) were added to the mixed solution. Subsequently, the mixture was extracted with ethyl acetate (100 mL×4). The combined organic layer was dried over sodium sulfate. The mixture was concentrated under reduced pressure and purified by a medium-pressure column chromatography (Smart Flash EPCLC W-Prep 2XY system) (n-hexane/AcOEt=5/1), and thus 4-(2,4-dichlorophenyl)-5-methoxy-2-methylbenzo[d]thiazole (compound 13a) (4.08 g, 12.6 mmol, quantitative) was obtained as an orange-brown solid.

TLC R$_f$=0.45 (n-hexane/EtOAc=5/1)

$^1$H NMR (400 MHz, CDCl$_3$) δ 7.71 (d, J=8.8 Hz, 1H, aromatic), 7.50 (s, 1H, aromatic), 7.29 (s, 2H, aromatic), 7.02 (d, J=8.8 Hz, 1H, aromatic), 3.75 (s, 3H, OCH$_3$), 2.66 (s, 3H, hetArCH$_3$)

Synthesis of 4-(2,4-dichlorophenyl)-3-ethyl-5-methoxy-2-methylbenzo[d]thiazol-3-ium triflate (Compound 13b)

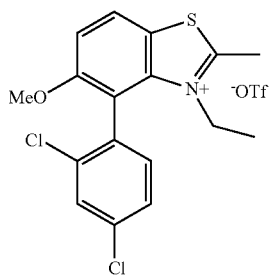 [SMILES: CC[n+]1c(C)sc2ccc(OC)c(-c3ccc(Cl)cc3Cl)c21 ; "-OTf"]

Under the argon atmosphere, an ethyl triflate (EtOTf) (5.5 mL, commercial product) suspension of the compound 13a (3.89 mg, 12.0 mmol) was stirred by heating at 50° C. (i.e., the oil bath temperature) for 19.5 hours. After the suspension was allowed to cool to room temperature, the precipitated crystal was filtered off with a Hirsch funnel. The crystal was washed with n-hexane (3 mL×4), and thus 4-(2,4-dichlorophenyl)-3-ethyl-5-methoxy-2-methylbenzo[d]thiazol-3-ium triflate (compound 13b) (5.50 g, 10.9 mmol, 91.2%) was obtained as a gray solid.

$^1$H NMR (400 MHz, CDCl$_3$) δ 8.12 (d, J=9.2 Hz, 1H, aromatic), 7.58 (d, J=2.4 Hz, 1H, aromatic), 7.54 (d, J=8.4 Hz, 1H, aromatic), 7.48-7.41 (m, 2H, aromatic), 7.28 (d, J=9.2 Hz, 1H, aromatic), 4.27 (q, J=7.2 Hz, 2H, CH$_2$CH$_3$), 3.85 (s, 3H, OCH$_3$), 3.16 (s, 3H, hetArCH$_3$), 1.14 (t, J=7.2 Hz, 3H, CH$_2$CH$_3$)

Synthesis of (Z)-1-(4-(2,4-dichlorophenyl)-3-ethyl-5-methoxybenzo[d]thiazole-2(3H)-ylidene)propan-2-one (Compound 13c)

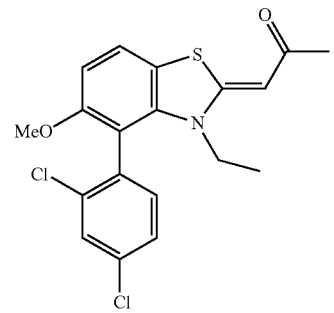 [SMILES: CCN1/C(=C/C(C)=O)Sc2ccc(OC)c(-c3ccc(Cl)cc3Cl)c21]

Under the argon atmosphere, triethylamine (6.10 mL, 43.8 mmol, commercial product) and acetyl chloride (2.30 mL, 32.3 µmol, commercial product) were added at −78° C. to a dichloromethane (110 mL, dehydrated, commercial product) solution of the compound 13b (5.50 g, 10.9 mmol). The temperature was raised to room temperature, and then the mixture was stirred for 1.5 hours. After the reaction was completed, water (about 50 mL) was added to the mixture. Subsequently, the mixture was extracted with dichloromethane (50 mL×4). The combined organic layer was dried over sodium sulfate and filtered. The filtrate was concentrated under reduced pressure and purified by a medium-pressure column chromatography (Smart Flash EPCLC W-Prep 2XY system) (n-hexane/EtOAc=1/1), and thus (Z)-1-(4-(2,4-dichlorophenyl)-3-ethyl-5-methoxybenzo[d]thiazole-2(3H)-ylidene)propan-2-one (compound 13c) (2.54 g, 6.44 mmol, 59.1%) was obtained as an yellow solid.

TLC R$_f$=0.30 (n-hexane/EtOAc=1/1)

$^1$H NMR (400 MHz, CDCl$_3$) δ 7.55 (d, J=6.4 Hz, 1H, aromatic), 7.54 (s, 1H, aromatic), 7.37 (d, J=6.4 Hz, 1H, aromatic), 7.27 (d, J=6.4 Hz, 1H, aromatic), 6.83 (d, J=6.4 Hz, 1H, aromatic), 5.80 (s, 1H, olefinic), 3.72 (s, 3H, OCH$_3$), 3.64-3.48 (m, 2H, CH$_2$CH$_3$), 2.23 (s, 3H, C(O)CH$_3$), 0.97 (t, J=5.6 Hz, 3H, CH$_2$CH$_3$)

Synthesis of (Z)-1-(4-(2,4-dichlorophenyl)-3-ethyl-5-hydroxybenzo[d]thiazol-2(3H)-ylidene)propan-2-one (Compound 13d)

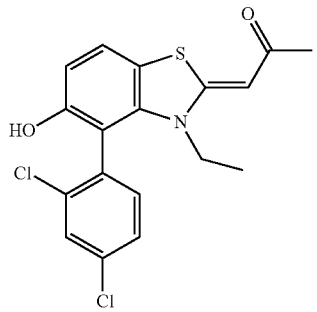 [SMILES: CCN1/C(=C/C(C)=O)Sc2ccc(O)c(-c3ccc(Cl)cc3Cl)c21]

Under the argon atmosphere, boron tribromide (1.0 M dichloromethane solution, 18.5 mL, 18.5 mmol, commercial product) was added at 0° C. to a dichloromethane (65 mL, dehydrated, commercial product) solution of the compound 13c (2.54 g, 6.44 mmol). The temperature was raised to room temperature, and then the mixture was stirred for 3 hours. After the reaction was completed, water (about 50 mL) was added at 0° C. to the mixture. Subsequently, the mixture was extracted with dichloromethane (30 mL×4) and a small amount of methanol (about 2 mL). The combined organic layer was dried over sodium sulfate and filtered. The filtrate was concentrated under reduced pressure. The resultant solid was filtered off with a Hirsch funnel. The solid was washed with cold methanol (3 mL×4), and thus (Z)-1-(4-(2,4-dichlorophenyl)-3-ethyl-5-hydroxybenzo[d]thiazol-2(3H)-ylidene)propan-2-one (compound 13d) (1.73 g, 4.55 mmol, 70.6%) was obtained as an yellow solid.

TLC $R_f$=0.20 ($CH_2Cl_2$/MeOH=20/1)

$^1$H NMR (400 MHz, DMSO-$d_6$) δ 9.72 (s, 1H, ArOH), 7.78 (d, J=1.2 Hz, 1H, aromatic), 7.57 (d, J=8.4 Hz, 1H, aromatic), 7.52 (brs, 2H, aromatic), 6.82 (d, J=8.4 Hz, 1H, aromatic), 5.96 (s, 1H, olefinic), 3.70-3.60 (m, 1H, $CH_{AA'\text{-}Gem}CH_3$), 3.50-3.41 (m, 1H, $CH_{AA'\text{-}Gem}CH_3$), 2.07 (s, 3H, C(O)CH$_3$), 0.85 (t, J=6.8 Hz, 3H, CH$_2$CH$_3$)

Synthesis of (Z)-1-(8-chloro-1-ethylbenzo[2,3]benzofuro[4,5-d]thiazol-2(1H)-ylidene)propan-2-one (Compound 13)

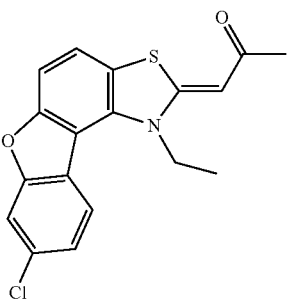 [SMILES: CCN1/C(=C/C(C)=O)Sc2ccc3oc4cc(Cl)ccc4c3c21]

Under the argon atmosphere, an N,N-dimethylacetamide (20 mL, dehydrated, commercial product) solution of the compound 13d (152 mg, 0.400 mmol) and copper (I) thiophene-2-carboxylate (91.5 mg, 0.480 mmol, commercial product) was stirred by heating at 250° C. for 30 minutes under microwave irradiation. After the solution was allowed to cool to room temperature, hydrochloric acid (1 M, 0.8 mL) was added to the solution. Subsequently, the mixture was extracted with dichloromethane (10 mL×4). The combined organic layer was dried over sodium sulfate and filtered. The filtrate was concentrated under reduced pressure and purified by a medium-pressure column chromatography (Smart Flash EPCLC W-Prep 2XY system) (n-hexane/EtOAc=1/1), and thus (Z)-1-(8-chloro-1-ethylbenzo[2,3]benzofuro[4,5-d]thiazol-2(1H)-ylidene)propan-2-one (compound 13) (82.6 mg, 0.240 mmol, 60.1%) was obtained as an yellow solid.

TLC $R_f$=0.35 (n-hexane/EtOAc=1/1)

mp 224-225° C.

IR (KBr, cm$^{-1}$) 3066, 2970, 2928, 1607, 1589, 1270, 1125, 600, 500

$^1$H NMR (500 MHz, CDCl$_3$) δ 7.92 (d, J=9.0 Hz, 1H, aromatic), 7.64 (s, 1H, aromatic), 7.63 (dd, J=9.0, 1.5 Hz, 1H, aromatic), 7.41 (d, J=8.5 Hz, 1H, aromatic), 7.37 (dd, J=8.5, 1.5 Hz, 1H, aromatic), 6.04 (s, 1H, olefinic), 4.61 (q, J=7.5 Hz, 2H, CH$_2$CH$_3$), 2.30 (s, 3H, C(O)CH$_3$), 1.71 (t, J=7.5 Hz, 3H, CH$_2$CH$_3$)

$^{13}$C NMR (126 MHz, CDCl$_3$) δ 191.3, 160.6, 157.0, 156.3, 135.0, 132.8, 123.8, 123.1, 121.8, 121.4, 120.1, 112.8, 108.6, 106.9, 90.4, 43.6, 29.1, 14.3

Production Example 14: Production of Compound 14

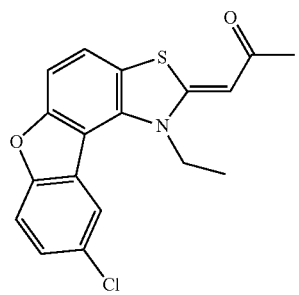

Compound 14

A compound 14 was produced in the following manner.

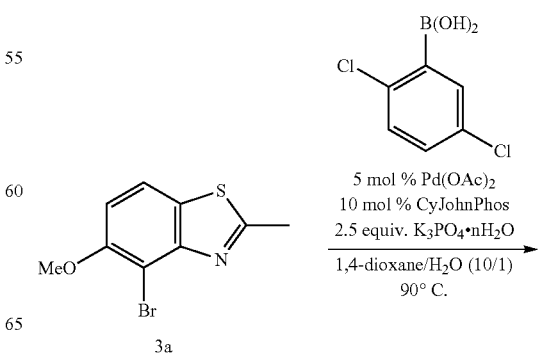

-continued

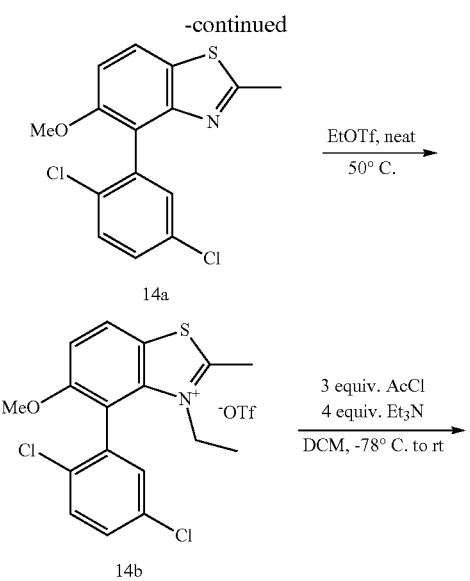

Synthesis of 4-(2,5-dichlorophenyl)-5-methoxy-2-methylbenzo[d]thiazole (Compound 14a)

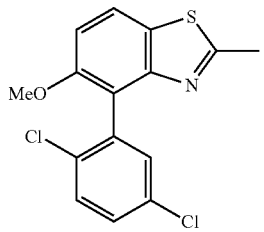 [SMILES: COc1ccc2sc(C)nc2c1-c1cc(Cl)ccc1Cl]

Under the argon atmosphere, a mixed solution including the compound 3a (3.10 g, 12.0 mmol), (2,5-dichlorophenyl) boronic acid (3.26 g, 17.1 mmol, commercial product), palladium acetate (Pd(OAc)$_2$) (135 mg, 0.601 mmol, commercial product), (2-biphenyl)dicyclohexylphosphine (421 mg, 1.20 mmol, commercial product), dioxane (120 mL, dehydrated, commercial product) of tri-potassium phosphate n-hydrate (6.40 g, 24.0 mmol, commercial product), and purified water (12 mL) was stirred by heating at 90° C. for 8.5 hours. After the mixed solution was allowed to cool to room temperature, water (50 mL) and saturated saline (50 mL) were added to the mixed solution. Subsequently, the mixture was extracted with ethyl acetate (100 mL×4). The combined organic layer was dried over sodium sulfate. The mixture was concentrated under reduced pressure and purified by a medium-pressure column chromatography (Smart Flash EPCLC W-Prep 2XY system) (n-hexane/AcOEt=5/1), and thus 4-(2,5-dichlorophenyl)-5-methoxy-2-methylbenzo[d]thiazole (compound 14a) (3.61 g, 11.1 mmol, 92.8%) was obtained as a brown solid.

TLC R$_f$=0.45 (n-hexane/EtOAc=5/1)

$^1$H NMR (400 MHz, CDCl$_3$) δ 7.80 (d, J=8.8 Hz, 1H, aromatic), 7.44 (d, J=8.4 Hz, 1H, aromatic), 7.37 (d, J=2.4 Hz, 1H, aromatic), 7.30 (dd, J=8.4, 2.4 Hz, 1H, aromatic), 7.10, (d, J=8.8 Hz, 1H, aromatic), 3.84 (s, 3H, OCH$_3$), 2.75 (s, 3H, hetArCH$_3$)

Synthesis of 4-(2,5-dichlorophenyl)-3-ethyl-5-methoxy-2-methylbenzo[d]thiazol-3-ium triflate (Compound 14b)

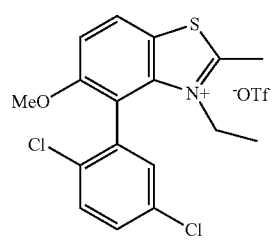 [SMILES: CC[n+]1c(C)sc2ccc(OC)c(-c3cc(Cl)ccc3Cl)c21 ; "-OTf"]

Under the argon atmosphere, an ethyl triflate (EtOTf) (10 mL, commercial product) suspension of the compound 14a (3.61 mg, 11.1 mmol) was stirred by heating at 50° C. (i.e., the oil bath temperature) for 11.5 hours. After the suspension was allowed to cool to room temperature, the precipitated crystal was filtered off with a Hirsch funnel. The crystal was washed with n-hexane (3 mL×4), and thus 4-(2,5-dichlorophenyl)-3-ethyl-5-methoxy-2-methylbenzo[d]thiazol-3-ium

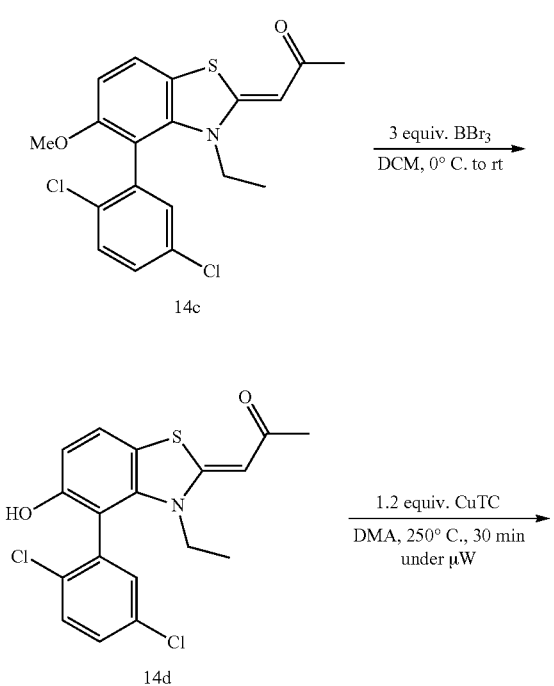

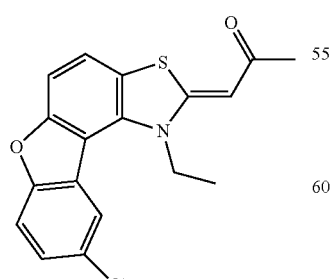

triflate (compound 14b) (4.98 g, 9.91 mmol, 89.3%) was obtained as a light brown solid.

$^1$H NMR (400 MHz, CDCl$_3$) δ 8.18 (d, J=7.2 Hz, 1H, aromatic), 7.53-7.43 (m, 4H, aromatic), 4.32-4.17 (m, 2H, CH$_2$CH$_3$), 3.86 (s, 3H, OCH$_3$), 3.18 (s, 3H, hetArCH$_3$), 1.16 (t, J=7.2 Hz, 3H, CH$_2$CH$_3$)

Synthesis of (Z)-1-(4-(2,5-dichlorophenyl)-3-ethyl-5-methoxybenzo[d]thiazole-2(3H)-ylidene)propan-2-one (Compound 14c)

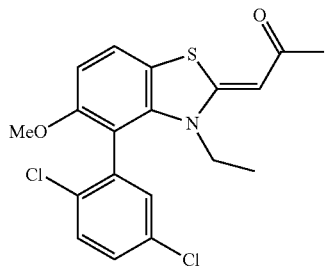 [SMILES: CCN1/C(=C/C(C)=O)Sc2ccc(OC)c(-c3cc(Cl)ccc3Cl)c21]

Under the argon atmosphere, triethylamine (1.40 mL, 10.0 mmol, commercial product) and acetyl chloride (530 μL, 7.45 μmol, commercial product) were added at −78° C. to a dichloromethane (25 mL, dehydrated, commercial product) solution of the compound 14b (1.26 g, 2.51 mmol). The temperature was raised to room temperature, and then the mixture was stirred for 30 minutes. After the reaction was completed, water (about 5 mL) was added to the mixture. Subsequently, the mixture was extracted with dichloromethane (20 mL×4). The combined organic layer was dried over sodium sulfate and filtered. The filtrate was concentrated under reduced pressure and purified by a medium-pressure column chromatography (Smart Flash EPCLC W-Prep 2XY system) (n-hexane/EtOAc=1/1), and thus (Z)-1-(4-(2,5-dichlorophenyl)-3-ethyl-5-methoxybenzo[d]thiazole-2(3H)-ylidene)propan-2-one (compound 14c) (545 mg, 1.38 mmol, 55.1%) was obtained as an yellow solid.

TLC R$_f$=0.30 (n-hexane/EtOAc=1/1)

$^1$H NMR (400 MHz, CDCl$_3$) δ 7.54 (d, J=7.6 Hz, 1H, aromatic), 7.45 (d, J=8.8 Hz, 1H, aromatic), 7.39-7.33 (m, 2H, aromatic), 6.82 (d, J=8.8 Hz, 1H, aromatic), 5.80 (s, 1H, olefinic), 3.73 (s, 3H, OCH$_3$), 3.64-3.45 (m, 2H, CH$_2$CH$_3$), 2.22 (s, 3H, C(O)CH$_3$), 0.99 (t, J=7.2 Hz, 3H, CH$_2$CH$_3$)

Synthesis of (Z)-1-(4-(2,5-dichlorophenyl)-3-ethyl-5-hydroxybenzo[d]thiazol-2(3H)-ylidene)propan-2-one (Compound 14d)

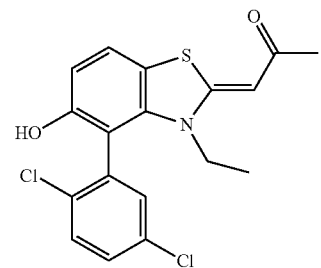 [SMILES: CCN1/C(=C/C(C)=O)Sc2ccc(O)c(-c3cc(Cl)ccc3Cl)c21]

Under the argon atmosphere, boron tribromide (1.0 M dichloromethane solution, 6.0 mL, 6.0 mmol, commercial product) was added at 0° C. to a dichloromethane (20 mL, dehydrated, commercial product) solution of the compound 14c (805 mg, 2.04 mmol). The temperature was raised to room temperature, and then the mixture was stirred for 2.5 hours. After the reaction was completed, water (about 5 mL) was added at 0° C. to the mixture. Subsequently, the mixture was extracted with dichloromethane (3 mL×4) and a small amount of methanol (about 0.5 mL). The combined organic layer was dried over sodium sulfate and filtered. The filtrate was concentrated under reduced pressure and purified by a medium-pressure column chromatography (Smart Flash EPCLC W-Prep 2XY system) (CH$_2$Cl$_2$/MeOH=20/1), and thus (Z)-1-(4-(2,5-dichlorophenyl)-3-ethyl-5-hydroxybenzo[d]thiazol-2(3H)-ylidene)propan-2-one (compound 14d) (740 mg, 1.95 mmol, 95.4%) was obtained as a light yellow solid.

TLC R$_f$=0.20 (CH$_2$Cl$_2$/MeOH=20/1)

$^1$H NMR (400 MHz, DMSO-d$_6$) δ 9.72 (s, 1H, ArOH), 7.64-7.62 (m, 2H, aromatic), 7.57-7.53 (m, 2H, aromatic), 6.81 (d, J=8.8 Hz, 1H, aromatic), 5.95 (s, 1H, olefinic), 3.68-3.58 (m, 1H, CH$_{AA'\text{-}Gem}$CH$_3$), 3.47-3.30 (m, 1H, CH$_{AA'\text{-}Gem}$CH$_3$), 2.07 (s, 3H, C(O)CH$_3$), 0.87 (t, J=6.8 Hz, 3H, CH$_2$CH$_3$)

Synthesis of (Z)-1-(9-chloro-1-ethylbenzo[2,3]benzofuro[4,5-d]thiazol-2(1H)-ylidene)propan-2-one (Compound 14)

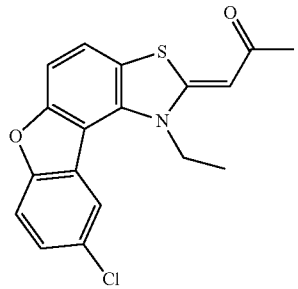 [SMILES: CCN1/C(=C/C(C)=O)Sc2ccc3oc4ccc(Cl)cc4c3c21]

Under the argon atmosphere, an N,N-dimethylacetamide (20 mL, dehydrated, commercial product) solution of the compound 14d (152 mg, 0.400 mmol) and copper (I) thiophene-2-carboxylate (91.5 mg, 0.480 mmol, commercial product) was stirred by heating at 250° C. for 30 minutes under microwave irradiation. After the solution was allowed to cool to room temperature, hydrochloric acid (1 M, 0.8 mL) was added to the solution. Subsequently, the mixture was extracted with dichloromethane (10 mL×4). The combined organic layer was dried over sodium sulfate and filtered. The filtrate was concentrated under reduced pressure and purified by a medium-pressure column chromatography (Smart Flash EPCLC W-Prep 2XY system) (n-hexane/EtOAc=1/1), and thus (Z)-1-(9-chloro-1-ethylbenzo[2,3]benzofuro[4,5-d]thiazol-2(1H)-ylidene)propan-2-one (compound 14) (103 mg, 0.300 mmol, 74.9%) was obtained as an orange-brown solid.

TLC R$_f$=0.40 (n-hexane/EtOAc=1/1)

mp 231-232° C.

IR (KBr cm$^{-1}$) 3099, 2962, 2360, 1485, 1201, 1013, 809, 773

$^1$H NMR (500 MHz, CDCl$_3$) δ 7.99 (d, J=2.0 Hz, 1H, aromatic), 7.65 (d, J=8.5 Hz, 1H, aromatic), 7.56 (d, J=8.5

Hz, 1H, aromatic), 7.47 (dd, J=8.5, 2.0 Hz, 1H, aromatic), 7.41, (d, J=8.5 Hz, 1H, aromatic), 6.05 (s, 1H, olefinic), 4.59 (q, 2H, J=7.2 Hz, $CH_2CH_3$), 2.30 (s, 3H, $C(O)CH_3$), 1.74 (t, J=7.5 Hz, 3H, $CH_2CH_3$)

$^{13}$C NMR (126 MHz, $CDCl_3$) δ 191.3, 160.6, 157.3, 154.4, 135.2, 128.7, 127.2, 122.7, 122.5, 121.9, 121.7, 113.2, 108.4, 107.0, 90.4, 43.7, 29.1, 14.4

Production Example 15: Production of Compound 15

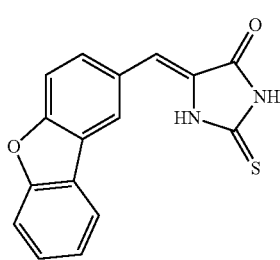

Compound 15

A compound 15 was produced in the following manner.

Under the argon atmosphere, acetic acid (AcOH) (57 μL, 1.0 mmol, commercial product) was added at room temperature to an acetonitrile (MeCN) (2 mL, dehydrated, commercial product) solution of dibenzofuran-2-carbaldehyde (196 mg, 0.999 mmol, synthesized according to Eur. J. Med. Chem., 2011, 46, 4827-4833), ammonium acetate ($NH_4OAc$) (38.5 mg, 0.499 mmol, commercial product), and thiohydantoin (133 mg, 1.15 mmol, commercial product). The mixture was heated to reflux for 2 hours. After the mixture was allowed to cool to room temperature, the precipitated crystal was filtered off with a Hirsch funnel. The crystal was washed with water (3 mL×4) and diethyl ether (3 mL×2), and thus (Z)-5-[(dibenzo[b, d]furan-2-yl)methylene]-2-thioxoimidazolidin-4-one (compound 15) (261 mg, 0.887 mmol, 88.8%, purity: about 90%) was obtained as a colorless solid. mp 291-292° C.

$^1$H NMR (400 MHz, DMSO-$d_6$) δ 12.40 (brs, 1H, NH), 12.25 (brs, 1H, NH), 8.58 (d, J=1.6 Hz, 1H, aromatic), 8.20 (d, J=7.6 Hz, 1H, aromatic), 7.84 (dd, J=8.8, 2.0 Hz, 1H, aromatic), 7.75-7.71 (m, 2H, aromatic), 7.59-7.54 (m, 1H, aromatic), 7.49-7.44 (m, 1H, aromatic), 6.67 (s, 1H, olefinic)

Experimental Example 1: Evaluation of Inhibitory Activity on Phosphorylation of Tau Protein The inhibitory activity of the compounds synthesized in the production examples on the phosphorylation of tau protein was evaluated by an evaluation system using the following cultured cells.

[Evaluation System]

The cultured cells that can induce the expressions of tau protein and DYRK1A protein individually and that allow the phosphorylation of the tau protein to be evaluated depending on the activity of the DYRK1A protein were used in the evaluation system. FIG. 1 shows an example of the results of performing western blotting on the cultured cells by using the following antibodies: (i) an antibody that specifically recognizes the phosphorylation of a threonine residue at position 212 of the tau protein (upper side); and (ii) an antibody that specifically recognizes the tau protein (lower side). As shown in FIG. 1, the cultured cells can express the tau protein and the DYRK1A protein individually, and the phosphorylation of the tau protein can be promoted by the DYRK1A protein. Therefore, the inhibitory activity on the phosphorylation of the tau protein can be evaluated by inducing the expressions of both the tau protein and the DYRK1A protein, and evaluating the degree of phosphorylation of a threonine residue at position 212 of the tau protein.

[Evaluation Results]

Figure 2:
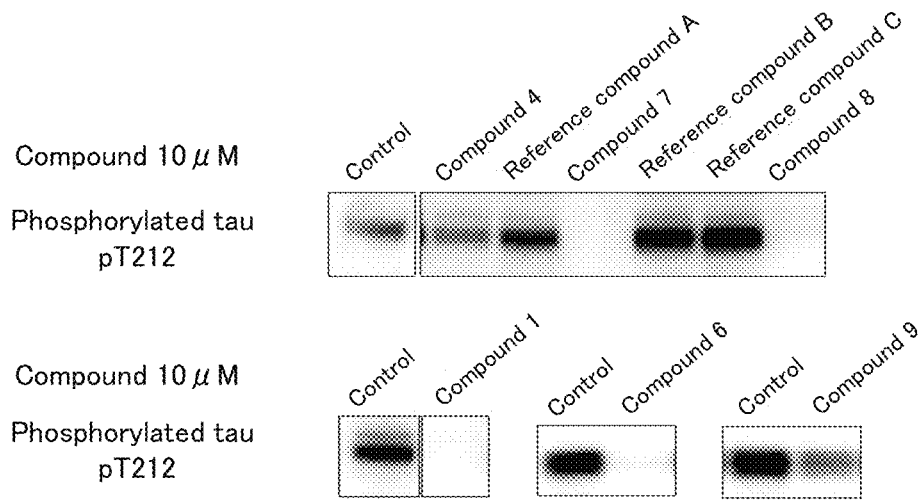
FIG. 2 shows an example of the results of performing western blotting on cultured cells in an evaluation system by using an antibody that specifically recognizes the phosphorylation of a threonine residue at position 212 of tau protein when the cultured cells have induced the expressions of both tau protein and DYRK1A protein in the presence of the compounds of 10 μM.

The compounds 1, 4, and 6 to 9 (10 μM) were added to the evaluation system, and the phosphorylation of the tau protein was detected with the antibody that specifically recognizes the phosphorylation of a threonine residue at position 212 of the tau protein. FIG. 2 shows an example of the results. FIG. 2 shows an example of the results of performing western blotting on the cultured cells by using the antibody that specifically recognizes the phosphorylation of a threonine residue at position 212 of the tau protein when the cultured cells have induced the expressions of both the tau protein and the DYRK1A protein in the presence of the compounds of 10 μM. The "control" represents the result of adding no compound. The reference compounds A to C did not have the inhibitory effect on the phosphorylation of the tau protein. As shown in FIG. 2, the compounds 1, 6, 7, and 8 had a significant inhibitory effect on the phosphorylation of the tau protein. Moreover, the compounds 4 and 9 also had the inhibitory effect on the phosphorylation of the tau protein.

Experimental Example 2: Evaluation of Intracerebral Transferability

The intracerebral transferability of the compound 1 was evaluated under the following conditions. The results showed that the cerebrospinal fluid concentration was 1.88 μM, while the plasma concentration was 13.5 μM. In other words, the intracerebral transferability of the compound 1 was confirmed.

[Evaluation Conditions of Intracerebral Transferability]

Experimental animal: 8-week-old male Wistar rat (about 300 g), caudal vein administration Administered vehicle: 20% PPG/8% tween 80/saline (2 mL/head)

Compound dosage: 2 mg/head

Figure 3:
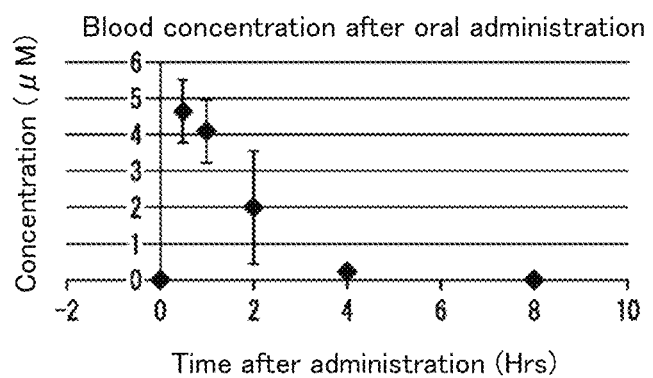
FIG. 3 is a graph showing an example of the results of evaluating oral absorbability of a compound 1.

Sampling time: 3 minutes after administration for plasma; 7 minutes after administration for cerebrospinal fluid Analytical sample: plasma of blood collected from inferior vena cava; cerebrospinal fluid Experimental Example 3: Evaluation of Oral Absorbability The oral absorbability of the compound 1 was evaluated under the following conditions. FIG. 3 shows an example of the results. As shown in FIG. 3, the oral absorbability of the compound 1 was confirmed.

[Evaluation Conditions of Oral Absorbability]

Experimental animal: 7-week-old male B6J mouse, oral administration

Administered vehicle: 5% gum arabic

Compound dosage: 100 mg/kg

Analytical sample: plasma of blood collected from inferior vena cava

Figure 4:
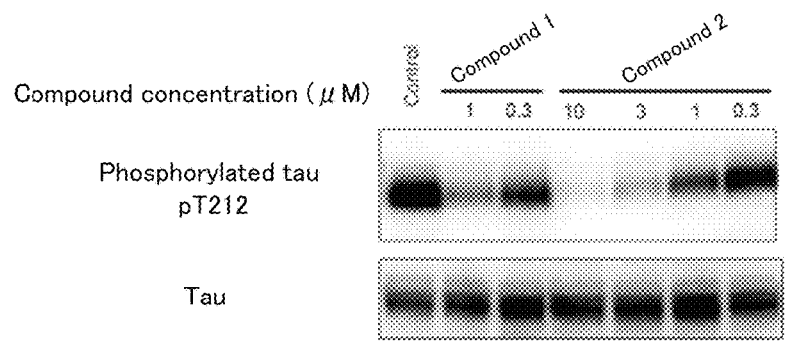
FIG. 4 shows an example of the results of performing western blotting on the cultured cells by using an antibody that specifically recognizes the phosphorylation of a threonine residue at position 212 of tau protein when the cultured cells have induced the expressions of both tau protein and DYRK1A protein in the presence of the compounds of 0.3 to 10 μM.

Experimental Example 4: Evaluation of Inhibitory Activity on Phosphorylation of Tau Protein The inhibitory activity of the compounds 1 and 2 on the phosphorylation of tau protein was evaluated in the same manner as the Experimental example 1. FIG. 4 shows an example of the results.

FIG. 4 shows an example of the results of performing western blotting on the cultured cells by using the antibody that specifically recognizes the phosphorylation of a threonine residue at position 212 of the tau protein when the cultured cells have induced the expressions of both the tau protein and the DYRK1A protein in the presence of the compounds at a concentration (0.3 to 10 μM) shown in FIG. 4. The "control" represents the result of adding no compound. As shown in FIG. 4, the compounds 1 and 2 had a significant inhibitory effect on the phosphorylation of the tau protein. The DYRK1A inhibitory capacity (IC50) in vitro was 49 nM for the compound 1 and 40 nM for the compound 2.

Figure 5:
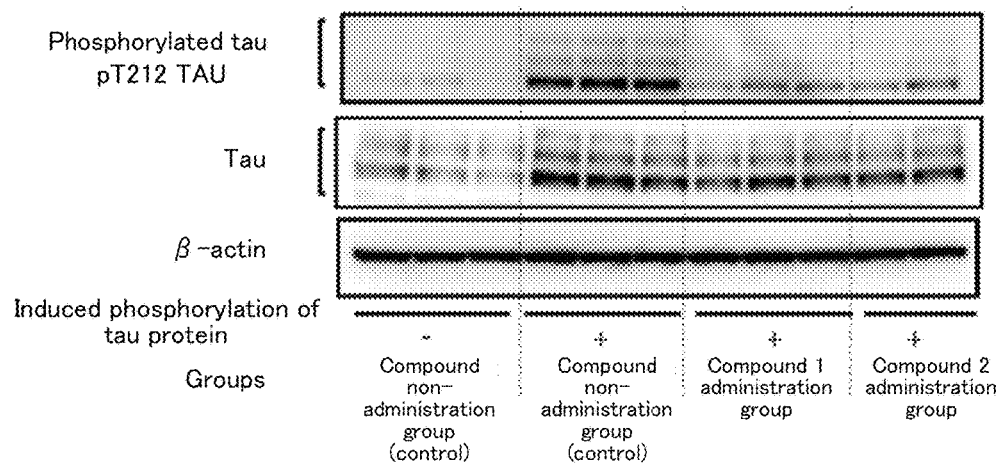
FIG. 5 shows an example of the results of performing western blotting to evaluate the degree of phosphorylation of a threonine residue at position 212 of tau protein by administering the compounds (100 mg/kg) before imposing stress and removing the brain tissue after imposing the stress, and to compare the degree of phosphorylation between the administration group of the compounds 1, 2 and the non-administration group of the compounds.

Experimental Example 5: Evaluation of Inhibitory Activity on Phosphorylation of Tau Protein in Brain The inhibitory activity of the compounds 1 and 2 on the phosphorylation of tau protein in the brain was evaluated. In the evaluation, a system was used which induced the phosphorylation of tau protein by imposing stress on mice (i.e., bathing the mice in ice-cold water for 5 minutes). FIG. 5 shows an example of the results.

FIG. 5 shows an example of the results of performing western blotting to evaluate the phosphorylation of the tau protein by administering the compounds (100 mg/kg) before imposing stress and removing the brain tissue after imposing the stress. As shown in FIG. 5, the results confirmed in vivo that the compounds 1 and 2 could inhibit the stress-induced phosphorylation of the tau protein.

Figure 6:
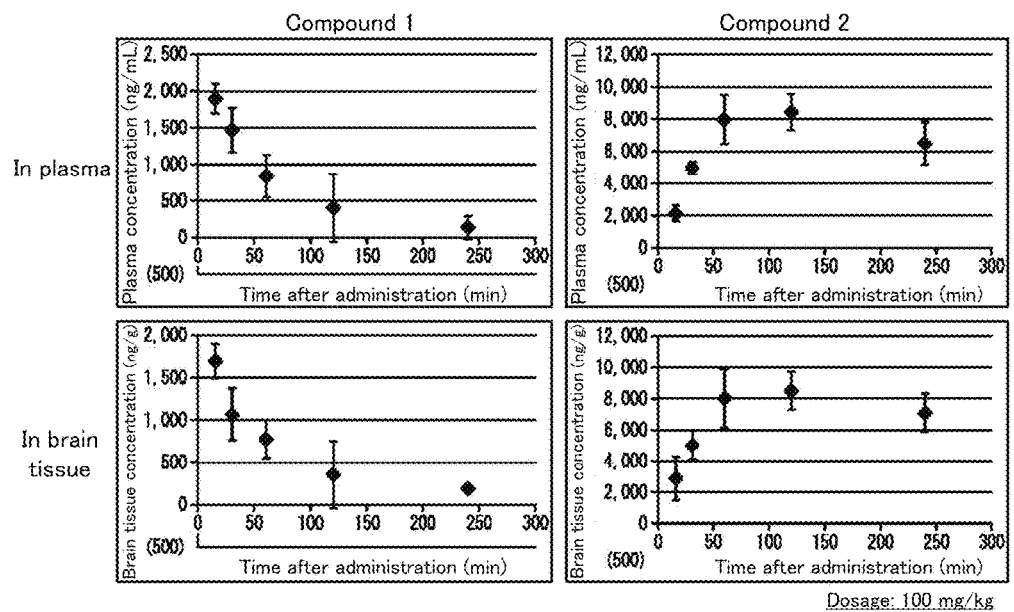
FIG. 6 shows an example of the results of measuring a plasma concentration and a brain tissue concentration after oral administration of the compounds 1 and 2.

Experimental Example 6: Evaluation of Oral Absorbability and Intracerebral Transferability The oral absorbability and the intracerebral transferability of the compounds 1 and 2 were evaluated under the following conditions. FIG. 6 and Table 1 show an example of the results.

[Evaluation Conditions of Intracerebral Transferability]
Experimental animal: 7-week-old male ICR mouse, oral administration
 Administered vehicle: 0.5% carboxymethylcellulose
 Compound dosage: 100 mg/kg
 Analytical sample: plasma of blood collected from inferior vena cava; brain tissue FIG. 6 and Table 1 show an example of the results of measuring a plasma concentration and a brain tissue concentration after oral administration of the compounds 1 and 2. As shown in FIG. 6 and Table 1, the results confirmed that the compounds 1 and 2 had both oral absorbability and intracerebral transferability.

TABLE 1

|  | Compound 1 | Compound 2 |
|---|---|---|
| Maximum blood concentration | 1900 ng/mL | 8400 ng/mL |
| Maximum brain tissue concentration | 1700 ng/g | 8500 ng/g |
| Time to maximum concentration in blood and in brain tissue | within 15 minutes | 2 hours |
| Half-life in blood and in brain tissue | within 60 minutes | 4 hours or more |
| Brain tissue/blood ratio (B/P:mL/g) | about 0.9 | about 1.0 |

Compound dosage: 100 mg/kg

Figure 7:
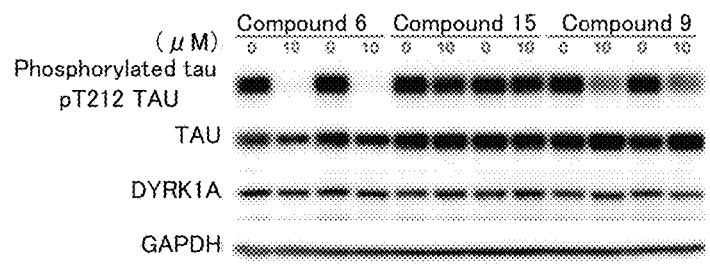
FIG. 7 shows an example of the results (compounds 6, 9, 15) of performing western blotting on cultured cells in an evaluation system by using an antibody that specifically recognizes the phosphorylation of a threonine residue at position 212 of tau protein when the cultured cells have induced the expressions of both tau protein and DYRK1A protein in the presence of the compounds of 10 μM.
Figure 8:
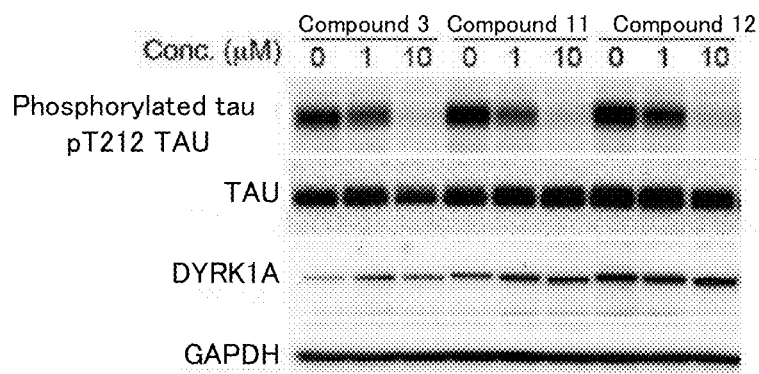
FIG. 8 shows an example of the results (compounds 3, 11, 12) of performing western blotting on cultured cells in an evaluation system by using an antibody that specifically recognizes the phosphorylation of a threonine residue at position 212 of tau protein when the cultured cells have induced the expressions of both tau protein and DYRK1A protein in the presence of the compounds of 10 μM.
Figure 9:
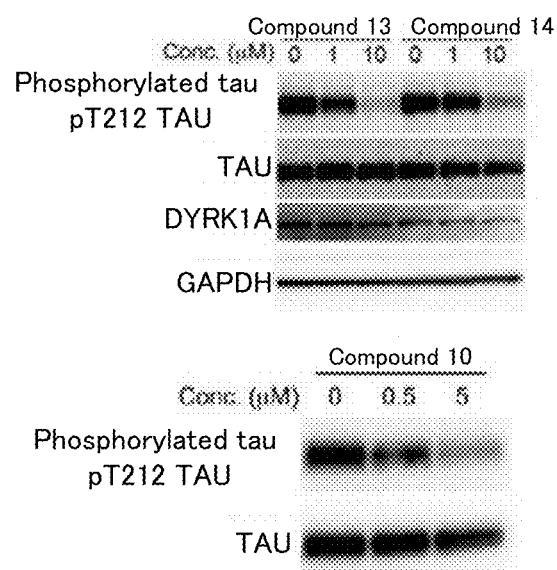
FIG. 9 shows an example of the results (compounds 10, 13, 14) of performing western blotting on cultured cells in an evaluation system by using an antibody that specifically recognizes the phosphorylation of a threonine residue at position 212 of tau protein when the cultured cells have induced the expressions of both tau protein and DYRK1A protein in the presence of the compounds of 10 μM.

Experimental Example 7: Evaluation of Inhibitory Activity on Phosphorylation of Tau Protein The inhibitory activity of the compounds 3, 6, and 9 to 15 on the phosphorylation of tau protein was evaluated in the same manner as the experimental example 1. FIGS. 7 to 9 show an example of the results. FIG. 7 shows an example of the results of the compounds 6, 15, and 9. FIG. 8 shows an example of the results of the compounds 3, 11, and 12. FIG. 9 shows an example of the results of the compounds 13, 14, and 10. As shown in FIGS. 7 to 9, the compounds 3, 6, and 9 to 15 had the inhibitory effect on the phosphorylation of the tau protein.

Figure 10:
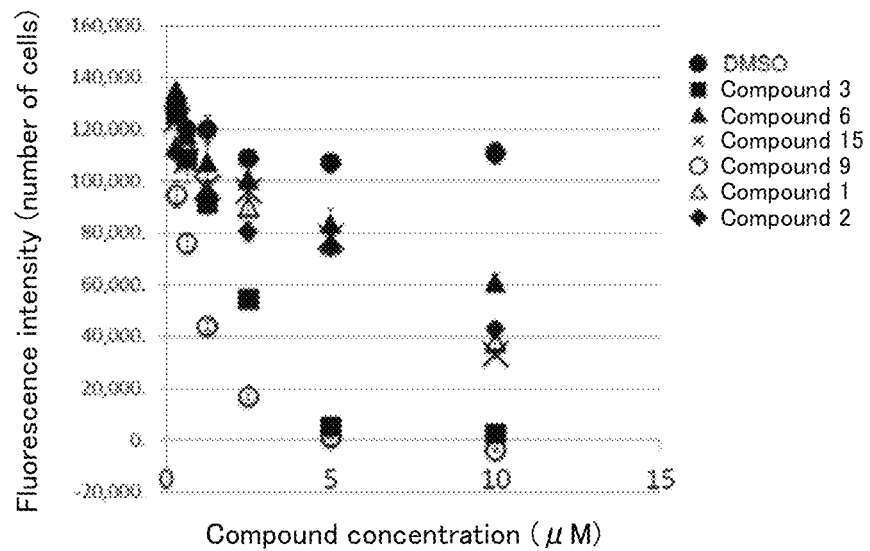
FIG. 10 shows an example of the results of evaluating the inhibitory effect of the compounds on the growth of Down's syndrome-derived acute megakaryoblastic leukemia cells CMK11-5. The number of cells was calculated by detecting the fluorescence intensity with Alamar Blue.
Figure 11:
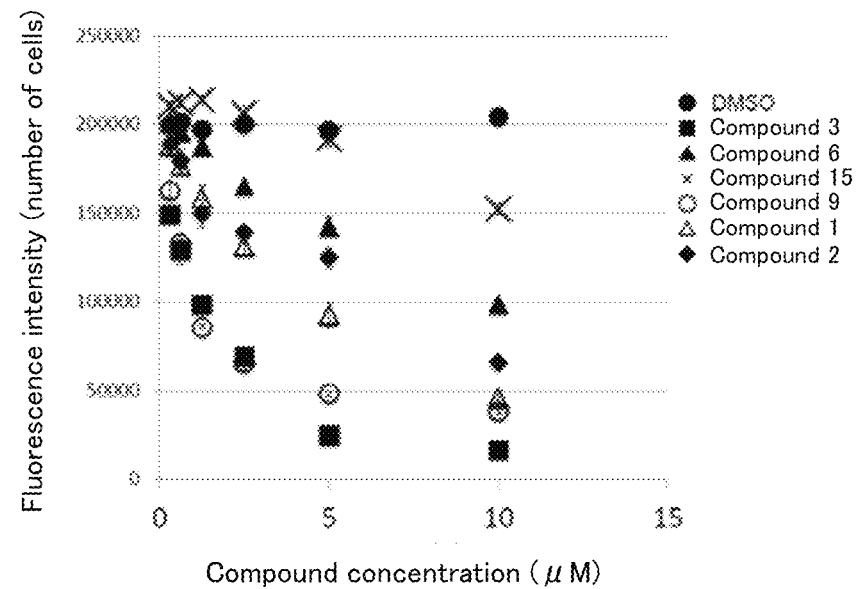
FIG. 11 shows an example of the results of evaluating the inhibitory effect of the compounds on the growth of Down's syndrome-derived acute megakaryoblastic leukemia cells J425. The number of cells was calculated by detecting the fluorescence intensity with Alamar Blue.
Figure 12:
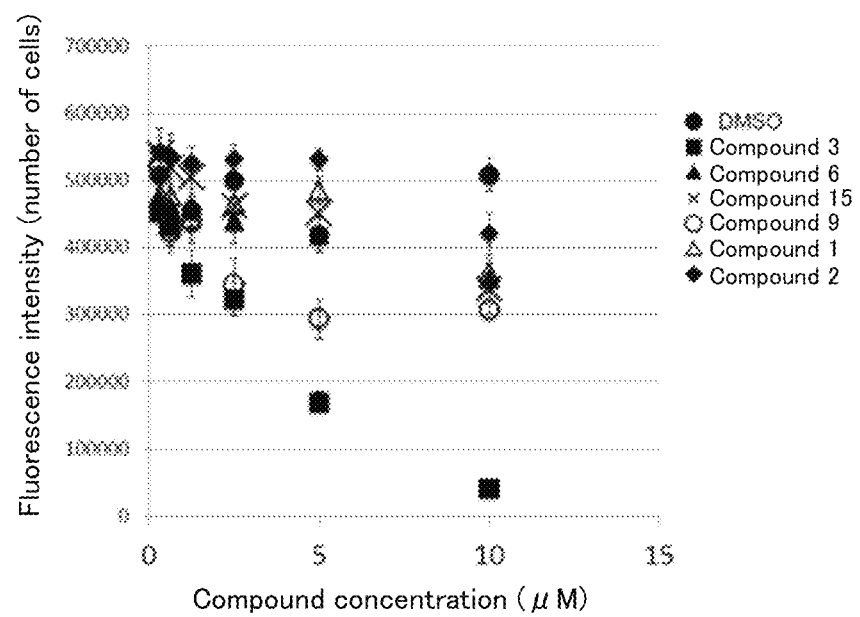
FIG. 12 shows an example of the results of evaluating the inhibitory effect of the compounds on the growth of Down's syndrome-derived acute megakaryoblastic leukemia cells KPAM1. The number of cells was calculated by detecting the fluorescence intensity with Alamar Blue.

Experimental Example 8: Evaluation of Inhibitory Effect on Growth of Cancer Cells The inhibitory effect of the compounds 1 to 3, 6, 9, and 15 on the growth of Down's syndrome-derived acute megakaryoblastic leukemia (AMKL) cells was evaluated. Specifically, the cells were seeded on a 24 Well plate, and the compounds at a predetermined concentration were added. After cultivation for 5 days, the number of cells was calculated by detecting the fluorescence intensity with Alamar Blue. The culture medium containing the compounds was replaced every day. FIGS. 10 to 12 show an example of the results. FIG. 10 shows an example of the results of the inhibitory effect on the growth of Down's syndrome-derived acute megakaryoblastic leukemia (AMKL) cells CMK11-5. As shown in FIG. 10, all the evaluated compounds had an excellent inhibitory effect on the growth of the cancer cells. FIG. 11 shows an example of the results of the inhibitory effect on the growth of Down's syndrome-derived acute megakaryoblastic leukemia (AMKL) cells J425. As shown in FIG. 11, particularly the compounds 1 to 3, 6, and 9 had an excellent inhibitory effect on the growth of the cancer cells. FIG. 12 shows an example of the results of the inhibitory effect on the growth of Down's syndrome-derived acute megakaryoblastic leukemia (AMKL) cells KPAM1. As shown in FIG. 12, particularly the compound 3 had an excellent inhibitory effect on the growth of the cancer cells.

Figure 13:
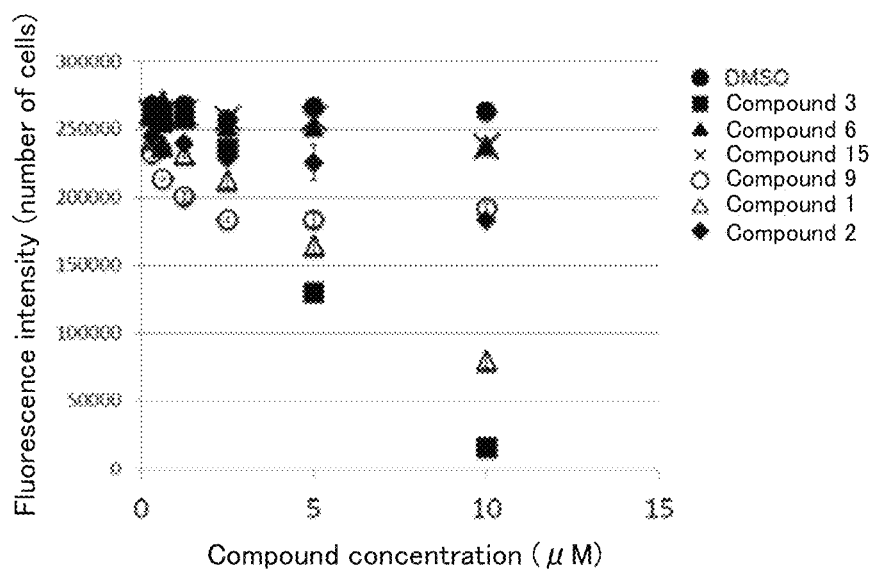
FIG. 13 shows an example of the results of evaluating the inhibitory effect of the compounds on the growth of retinoblastoma cell lines WERI. The number of cells was calculated by detecting the fluorescence intensity with Alamar Blue.

Experimental Example 9: Evaluation of Inhibitory Effect on Growth of Cancer Cells The inhibitory effect of the compounds 1 to 3, 6, 9, and 15 on the growth of retinoblastoma cell lines WERI was evaluated in the same manner as the experimental example 8. FIG. 13 shows an example of the results. As shown in FIG. 13, particularly the compounds 1 and 3 had the inhibitory effect on the growth of the cancer cells.

Figure 14:
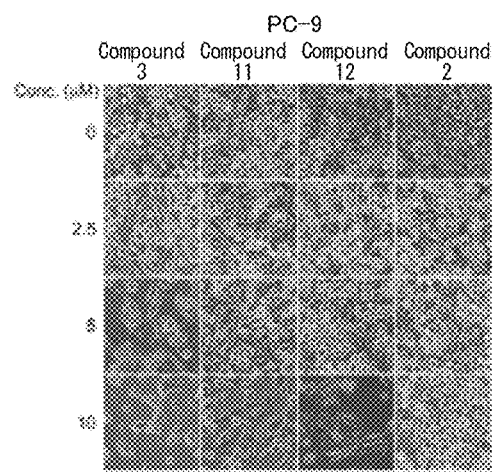
FIG. 14 shows an example of the results of microscopic observation of the inhibitory effect of the compounds 2, 3, 11, and 12 on the growth of human lung adenocarcinoma-derived cell lines (PC-9).
Figure 15:
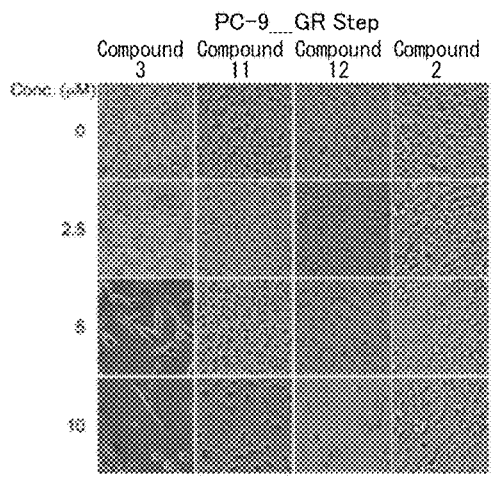
FIG. 15 shows an example of the results of microscopic observation of the inhibitory effect of the compounds 2, 3, 11, and 12 on the growth of human lung adenocarcinoma-derived cell lines (PC-9-GR-step).
Figure 16:
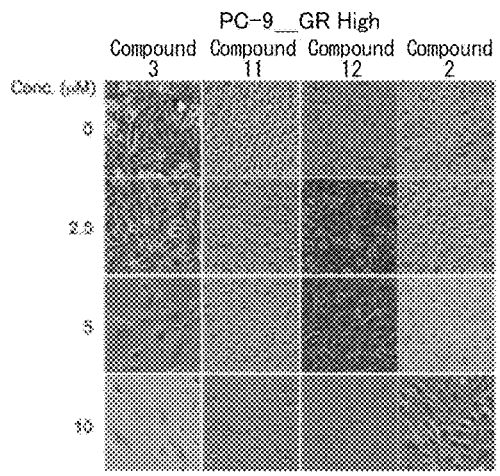
FIG. 16 shows an example of the results of microscopic observation of the inhibitory effect of the compounds 2, 3, 11, and 12 on the growth of human lung adenocarcinoma-derived cell lines (PC-9-GR-high).

Experimental Example 10: Evaluation of Inhibitory Effect on Growth of Cancer Cells The inhibitory effect of the compounds 2, 3, 11, and 12 on the growth of human lung adenocarcinoma-derived cell lines (PC-9) was evaluated in the same manner as the experimental example 8, and the resultant cultured cells were observed with a microscope. FIGS. 14 to 16 show the results. FIG. 14 shows the results of PC-9 lines. FIG. 15 shows the results of PC-9-GR-step lines that are EGFR inhibitor (gefitinib)-resistant sub-lines based on the PC-9 lines. FIG. 16 shows the results of PC-9-GR-high lines. As shown in FIGS. 14 to 16, particularly the compounds 3 and 12 had an excellent apoptosis-inducing activity on the cancer cells.

Figure 17:
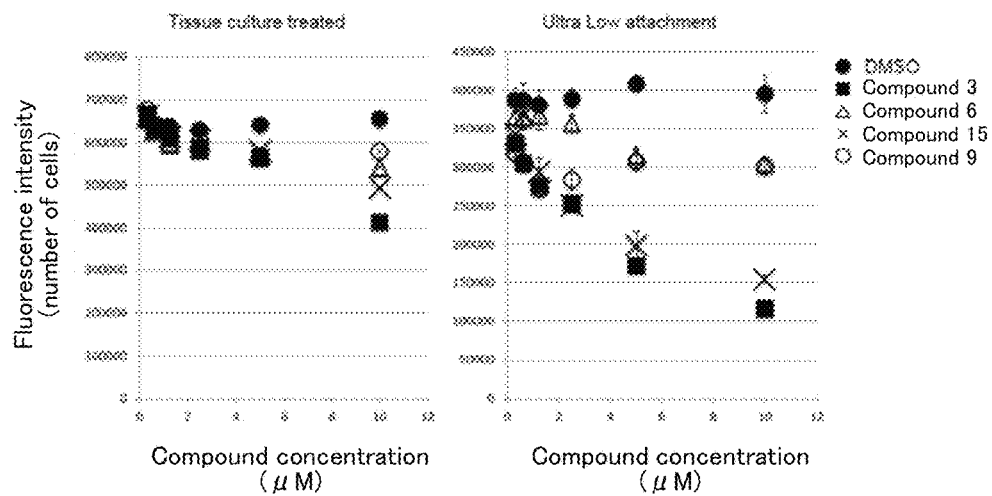
FIG. 17 shows an example of the results of evaluating the inhibitory effect of the compounds on the growth of cell lines (MDA-MB-453) of human breast cancer cells (triple-negative) in the case where the cells are cultured to allow them to adhere to each other and in the case where the cells are cultured to prevent them from adhering to each other. The number of cells was calculated by detecting the fluorescence intensity with Alamar Blue.
Figure 18:
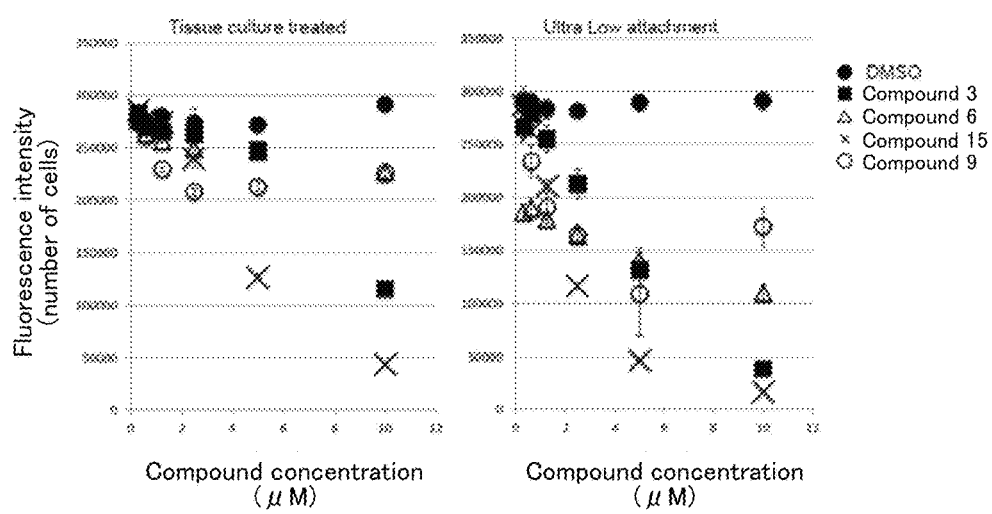
FIG. 18 shows an example of the results of evaluating the inhibitory effect of the compounds on the growth of cell lines (MDA-MB-468) of human breast cancer cells (triple-negative) in the case where the cells are cultured to allow them to adhere to each other and in the case where the cells are cultured to prevent them from adhering to each other. The number of cells was calculated by detecting the fluorescence intensity with Alamar Blue.

Experimental Example 11: Evaluation of Inhibitory Effect on Growth of Cancer Cells The inhibitory effect of the compounds 3, 6, 9, and 15 on the growth of two types of cell lines (MDA-MB-453 and MDA-MB-468) of human breast cancer cells (triple-negative) was evaluated in the same manner as the experimental example 8. In addition, the effect was also confirmed when the target cells were cultured to prevent them from adhering to each other. FIG. 17 shows the results of MDA-MB-453. FIG. 18 shows the results of MDA-MB-468. As shown in FIGS. 17 and 18, particularly the compounds 3 and 15 had the inhibitory effect on the anchorage-independent growth.

Experimental Example 12: Evaluation of Remedial Action on Memory and Learning Disabilities The remedial action of the compound 2 on memory and learning disabilities was evaluated. In the evaluation, amyloid-β peptide was administered into the cerebral ventricles of mice, and an evaluation system that induces memory and learning disabilities was used (Maurice et al., 1996). The tests were performed using 6-week-old male Swiss mice, which were divided into groups of 12 (n=12). Amyloid-β peptide (25-35, sequence: Gly-Ser-Asn-Lys-Gly-Ala-Ile-Ile-Gly-Leu-Met) or scrambled amyloid-β (25-35, sequence: Ala-Lys-Ile-Gly-Asn-Ser-Ile-Gly-Leu-Met-Gly), which was used as control peptide, was dissolved in distilled water, and each of the peptide solutions was incubated at 37° C. for 4 days.

The compound 2 for medication was dissolved in DMSO, and then diluted with 0.5% methylcellulose, thereby preparing a 10 mg/mL solution. The compound 2 solution or a vehicle was administered in a dosage of 100 mg/kg twice a day from the first day to the 12th day of the tests. Moreover, on the first day of the tests, each of the incubated peptide solutions was administered into the cerebral ventricles of the mice in an amount of 9 nmol per mouse one hour after the administration of the compound 2 or the vehicle.

Figure 19A:
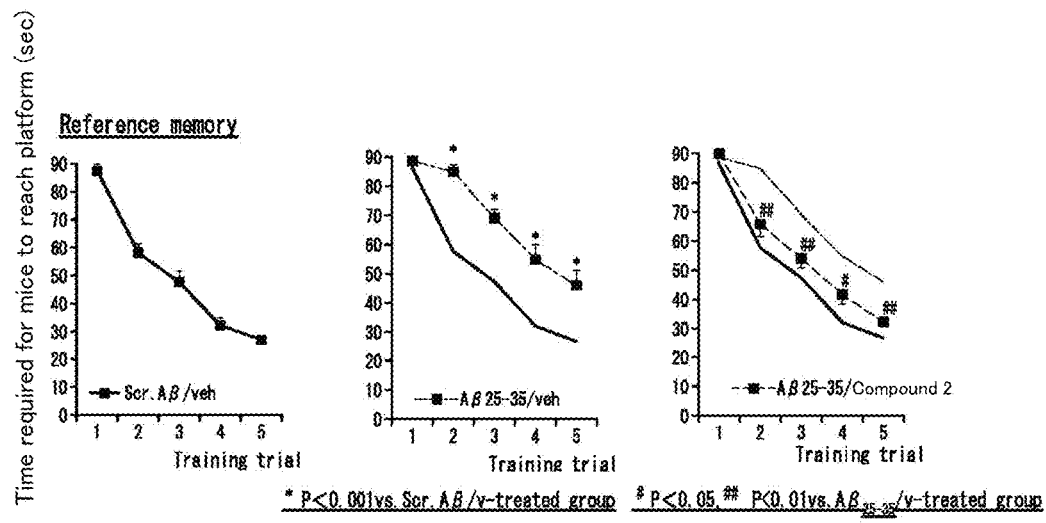
FIGS. 19A and 19B show the results of evaluating the remedial action of the compound 2 on memory and learning disabilities.
Figure 19B:
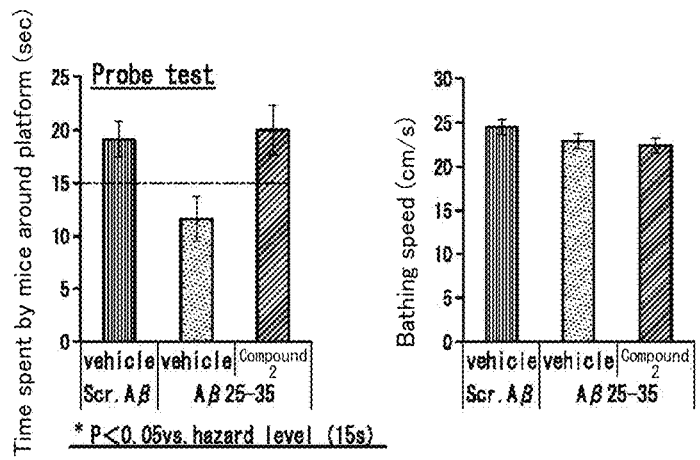

In order to evaluate a reference memory, water maze was performed three times a day using a circular pool (140 cm in diameter and 40 cm in height) and a platform (10 cm in diameter) between the 8th day and the 12th day of the tests. On the 13th day of the tests, a probe test was performed to record the behavior of the mice for 60 minutes using the circular pool in the absence of the platform. During the recording, the total time the mice spent in one-fourth of the area of the circle, including the place where the platform had been located until the previous day, was recorded. FIGS. 19A and 19B show an example of the results.

FIG. 19A shows the results of the reference memory between the 8th day (training trial 1) and the 12th day (training trial 5) of the tests. In the left graph, the scrambled amyloid-β (control peptide)/vehicle administration group is plotted. In the center graph, the amyloid-β/vehicle administration group is plotted along with the solid line indicating the results in the left graph. In the right graph, the amyloid-β/compound 2 administration group is plotted along with the solid line and the dashed line indicating the results in the center graph. Consequently, it took a longer time for the mice to reach the platform even after several days had passed in the amyloid-β/vehicle administration group of the center graph than in the scrambled amyloid-β/vehicle administration group of the left graph. In other words, the memory and learning abilities of the mice were reduced in the center graph compared to the left graph. On the other hand, it took a shorter time for the mice to reach the platform as days passed in the amyloid-β/compound 2 administration group of the right graph than in the amyloid-β/vehicle administration group of the center graph. In other words, the medication of the compound 2 improved the reduced memory and learning abilities due to the amyloid-β administration.

FIG. 19B shows the results of the probe test on the 13th day of the tests. Consequently, the time spent by the mice around the platform was shorter, i.e., the memory and learning abilities of the mice were reduced in the amyloid-β/vehicle administration group than in the scrambled amyloid-β (control peptide)/vehicle administration group. On the other hand, the time spent by the mice around the platform was longer in the amyloid-β/compound 2 administration group than in the amyloid-β/vehicle administration group, and was approximately the same value as that in the scrambled amyloid-β/vehicle administration group. In other words, the medication of the compound 2 improved the reduced memory and learning abilities due to the amyloid-β administration.

The results of the experimental examples confirmed in vivo that the compound 2 had the effect of improving the reduced memory and learning abilities due to the amyloid-β administration.

The invention claimed is:
1. A compound expressed by the following formula (I) or a prodrug of the compound or a pharmaceutically acceptable salt of the compound:

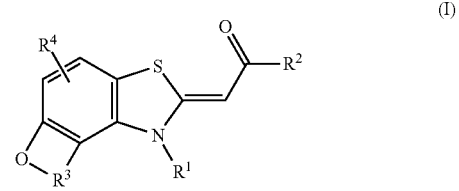

wherein, in formula (I),
R$^1$ and R$^2$ each independently represent a hydrogen atom or a C$_{1-6}$ hydrocarbon chain,
R$^3$ represents

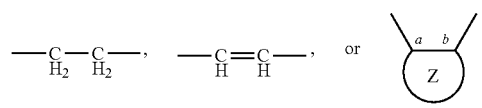

where Z and atoms marked with a and b form a ring selected from the group consisting of one benzene ring, one heteroaromatic ring, an aromatic ring in which one or more benzene rings are condensed, a heteroaromatic ring in which one or more heteroaromatic rings are condensed, a mixed condensed polycyclic ring in which one or more benzene rings are condensed with one or more heteroaromatic rings, and a cyclic aliphatic, and the ring may have at least one substituent that is a hydrogen atom, a halogen atom, or a $C_{1-6}$ alkyl group, and R⁴ represents a hydrogen atom, a halogen atom, or a $C_{1-6}$ alkyl group.

2. The compound according to claim 1, said compound being

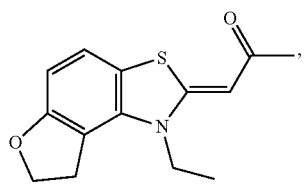

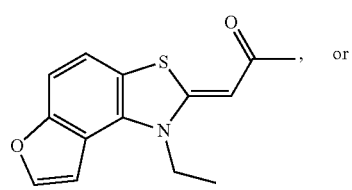, or

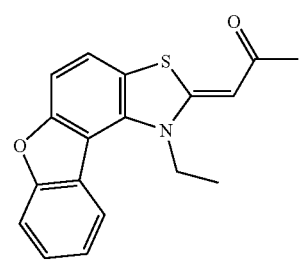

or a prodrug of the compound or a pharmaceutically acceptable salt of the compound.

3. The compound according to claim 1 expressed by the following formula (III) or a prodrug of the compound or a pharmaceutically acceptable salt of the compound:

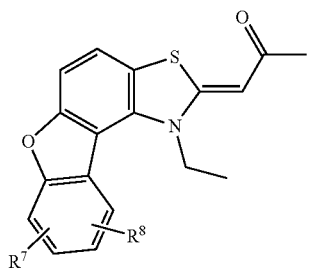

(III)

wherein, in formula (III), R⁷ and R⁸ each independently represent a hydrogen atom, a halogen atom, or a linear or branched $C_{1-6}$ alkyl group.

4. The compound according to claim 1, said compound being

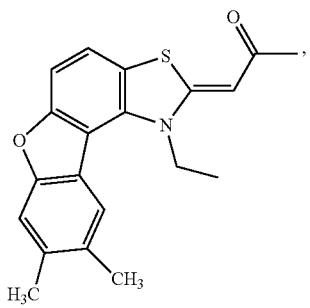

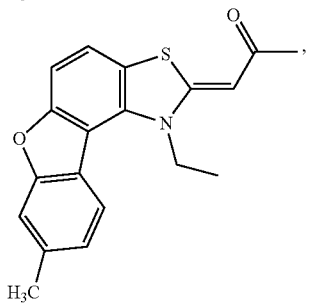

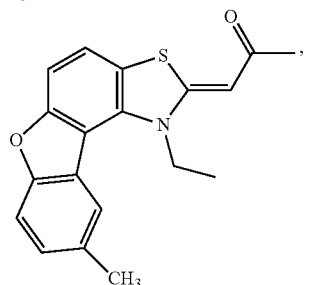

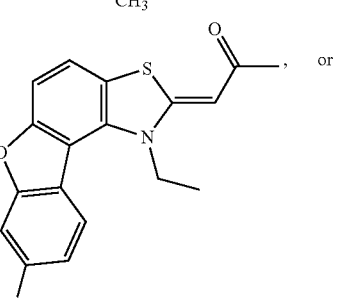, or

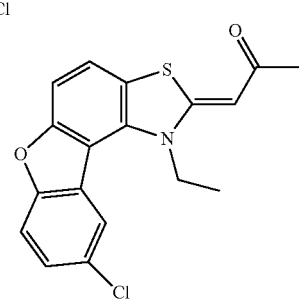

or a pharmaceutically acceptable salt of the compound.

5. A pharmaceutical composition containing the compound or the prodrug of the compound or the pharmaceutically acceptable salt of the compound according to claim 1 as an active ingredient.

6. A method for treating Down's syndrome, brain cancer, lung cancer, breast cancer, or Alzheimer's disease, said method comprising:

administering a compound expressed by the following formula (I) or a prodrug of the compound or a pharmaceutically acceptable salt of the compound to a subject in need thereof:

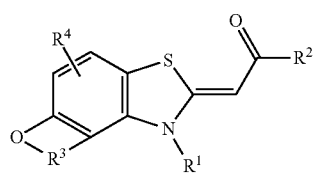

where, in the formula (I), $R^1$ and $R^2$ each independently represent a hydrogen atom or a $C_{1-6}$ hydrocarbon chain, $R^3$ represents

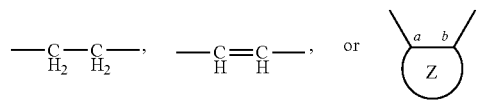

where Z and atoms marked with a and b form a ring selected from the group consisting of one benzene ring, one heteroaromatic ring, an aromatic ring in which one or more benzene rings are condensed, a heteroaromatic ring in which one or more heteroaromatic rings are condensed, a mixed condensed polycyclic ring in which one or more benzene rings are condensed with one or more heteroaromatic rings, and a cyclic aliphatic, and the ring may have at least one substituent that is a hydrogen atom, a halogen atom, or a $C_{1-6}$ alkyl group, and $R^4$ represents a hydrogen atom, a halogen atom, or a $C_{1-6}$ alkyl group.

7. The method according to claim 6, comprising:
administering a compound expressed by

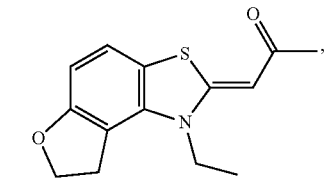

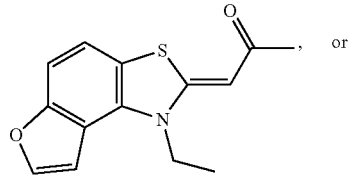

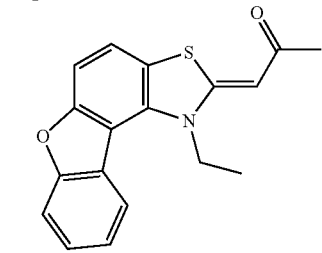

or a prodrug of the compound or a pharmaceutically acceptable salt of the compound to a subject in need thereof.

8. The method according to claim 6, comprising:
administering a compound expressed by the following formula (III) or a prodrug of the compound or a pharmaceutically acceptable salt of the compound to a subject in need thereof:

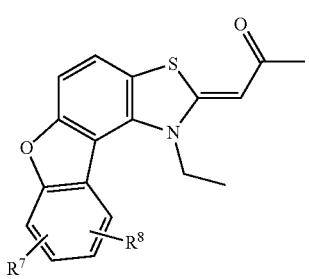

where, in the formula (III), $R^7$ and $R^8$ each independently represent a hydrogen atom, a halogen atom, or a linear or branched alkyl group.

9. The method according to claim 8, comprising:
administering a compound expressed by

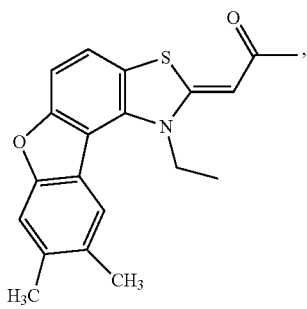

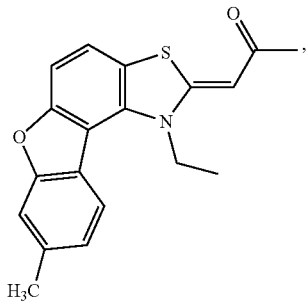

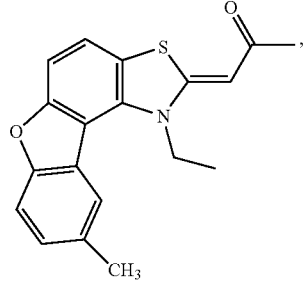

-continued
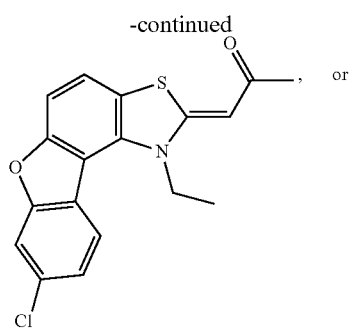
, or
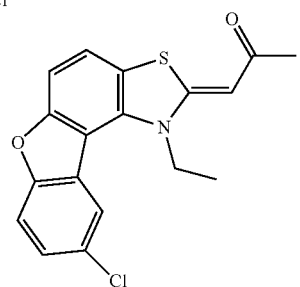
or a prodrug of the compound or a pharmaceutically acceptable salt of the compound to a subject in need thereof.
* * * * *